(12) United States Patent
Champtiaux et al.

(10) Patent No.: US 7,820,876 B2
(45) Date of Patent: Oct. 26, 2010

(54) MOUSE MUTANT FOR EXPRESSION OF THE ALPHA6 SUBUNIT OF THE NICOTINIC ACETYLCHOLINE RECEPTOR

(75) Inventors: Nicolas Champtiaux, Paris (FR); Jean-Pierre Changeux, Paris (FR); Alain Bessis, Paris (FR)

(73) Assignee: Institut Pasteur, Paris (FR)

( * ) Notice: Subject to any disclaimer, the term of this patent is extended or adjusted under 35 U.S.C. 154(b) by 689 days.

(21) Appl. No.: 10/377,614

(22) Filed: Mar. 4, 2003

(65) Prior Publication Data
US 2004/0006782 A1    Jan. 8, 2004

Related U.S. Application Data

(63) Continuation of application No. PCT/FR01/02741, filed on Sep. 4, 2001.

(30) Foreign Application Priority Data
Sep. 4, 2000    (FR)    .................. 00 11247

(51) Int. Cl.
*A01K 67/00* (2006.01)
*A01K 67/033* (2006.01)
*A01K 67/027* (2006.01)
(52) U.S. Cl. .............. 800/18; 800/8; 800/13; 800/14
(58) Field of Classification Search .............. 800/18
See application file for complete search history.

(56) References Cited

U.S. PATENT DOCUMENTS
6,252,132 B1 *  6/2001  Changeux et al. ............. 800/18

FOREIGN PATENT DOCUMENTS

| WO | WO 96 03504 | 2/1996 |
|---|---|---|
| WO | WO 96 41876 | 12/1996 |
| WO | WO 00/26362 | 5/2000 |
| WO | WO 00 26362 | 5/2000 |

OTHER PUBLICATIONS

Bradley et al. (1992) Modifying the mouse: Design and desire. Bio/Technology 10: 534-539.*
Campbell and Wilmut (1997) Totipotency and multipotentiality of cultured cells: Applications and progress. Theriogenology 47: 63-72.*
Doetschman, T. (1999) Interpretation of phenotype in genetically engineered mice. Laboratory Animal Science 49(2): 137-143.*
Donehower et al. (1995) Effects of genetic background on tumorigenesis in p53-deficient mice. Molecular Carcinogenesis 14: 16-22.*

(Continued)

*Primary Examiner*—Anne-Marie Falk
(74) *Attorney, Agent, or Firm*—Finnegan, Henderson, Farabow, Garrett & Dunner, LLP

(57) ABSTRACT

The invention concerns a non-human mammal carrying a mutation in the gene coding for the alpha6 subunit of the nicotinic acetylcholine receptor (nAChR), said mutation preventing expression of said nAChR alpha6 subunit in a functional form in the mammal.

Figure 1A:
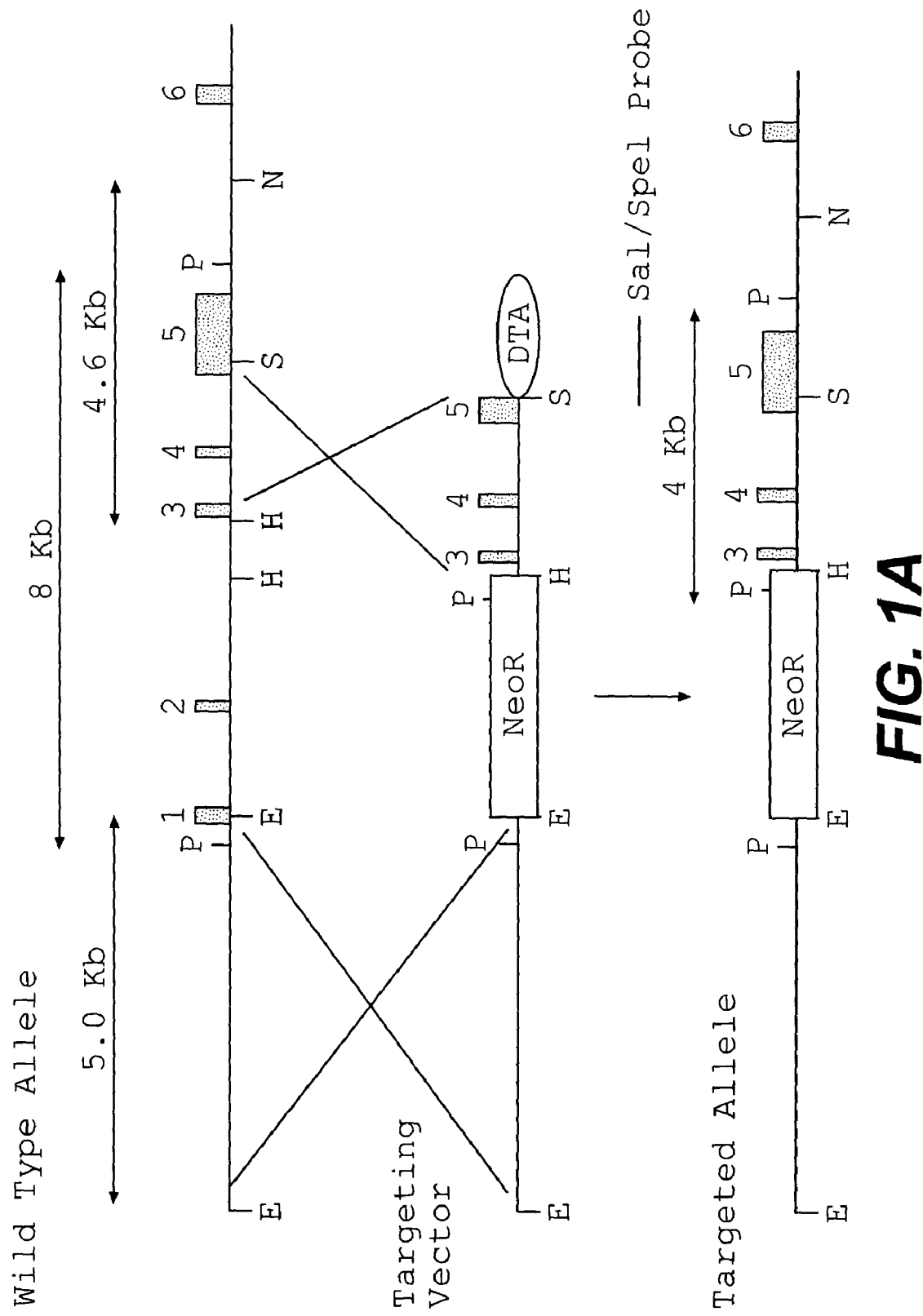

The invention also concerns synaptosome preparations obtained from said animals and cell cultures obtained by mutation of the alpha6 subunit as defined above.

11 Claims, 26 Drawing Sheets

OTHER PUBLICATIONS

Jacks et al. (1992) Effects of an Rb mutation in the mouse. Nature 359: 295-300.*

Jaenisch et al. (1988) Transgenic Animals. Science 240: 1468-1474.*

Kuehn et al. (1987) A potential animal model for Lesch-Nyhan syndrome through introduction of HPRT mutations into mice. Nature 326: 295-298.*

Moens et al. (1993) Defects in heart and lung development in compound heterozygotes for two different targeted mutations at the N-myc locus. Development 119: 485-499.*

Petridou et al. (2003) Heterogeneous inducible mammary-specific expression of JAB/SOCS1 in lactating transgenic mice is associated with no obvious phenotype, even at the cellular level. Transgenic Research 12: 693-706.*

Sigmund, CD (2000) Viewpoint: Are studies in genetically altered mice out of control? Arterioscler. Thromb. Vasc. Biol. 20: 1425-1429.*

Marubio et al. (Aug. 24, 1999) GenBank Accession No. AJ245706, Mus musculus mRNA for nicotinic acetylcholine receptor subunit alpha6.*

International Search Report in Corresponding PCT application No. PCT/FR01/02741.

Database E.B.I. Hinxton UK—Accession No. AZ273390, Jul. 30, 2000—Mouse BAC End Sequences from Library RPCI-23.

Database E.B.I. Hinxton UK—Accession No. AJ245706, 8/224/99—MUS musculus mRNA for nicotonic acetylcoline receptor subunit alpha 6.

Zoli et al.; Identification of four classes of brain nicotinic receptors using β2 mutant mice; Journal of Neuroscience 18(12) (1998) pp. 4461-4472.

LeNovere et al.; Involvement of α6 nicotinic receptor subunit in nicotine-elicited locomotion, demonstrated by in vivo antisense oligonucleotide infusion; NeuroReport 10 (1999) pp. 2497-2501.

Cordero-Erausquin, et al.; Nicotinic receptor function: new perspectives from knockout mice, TIPS (2000) pp. 211-217.

Stitzel, et al.; Potential role of the α4 and α6 nicotinic receptor subunits in regulating nicotine-induced seizures; J. Pharmacol. and Exper. Therap., vol 293(1) (2000) pp. 67-74.

Reuben et al., Nicotinic receptors modulating somatodendritic and terminal dopamine release differ pharmacologically; European Journal of Pharmacology 393 (2000) pp. 39-49.

Khillan et al.; Preparation of animals with a high degree of chimerism by one-step coculture of embryonic stem cells and preimplantation embryos; BioTechniques 22 (1997) pp. 544-549.

David I. Israel; A PCR-based method for high stringency screening of DNA libraries; Nucleic Acids Research vol. 21(11) (1993) pp. 2627-2631.

Kress, et al.; Nonpermissiveness for mouse embryonic stem (ES) cell derivation circumvented by a single backcross to 129/Sv strain; establishment of ES cell lines bearing the $OM^d$ conditional lethal mutation; Mammalian Genome 9 (1998) pp. 998-1001.

Marubio et al.; Reduced antinociception in mice lacking neuronal nicotinic receptor subunits; Nature vol. 398 (1999) pp. 805-810.

Organisation generale du systeme nerveus cetntral; Medecine et Science; No. 3, vol. 5 (1989) pp. 176-177 Summary only.

Champtiaux et al.; Inactivation genique de la sous-unite alpha 6 du recepteur nicotinique de l'acetylcholine. Etude des interactions entre systeme dopaminergique et systeme nicotinique dans l'establissement de la dependance a la nicotine; Abstract (2000).

La jonction synaptique: aspects pharmacologiques; Medecine et Science, No. 7, vol. 5, (1989) pp. 507-508.

Picciotto et al.: Abnormal avoidance learning in mice lacking functional high-affinity nicotine receptor in the brain; Nature 374:65-67 (1995).

Champtiaux et al.: Distribution and Pharmacology of α6-Containing Nicotinic Acetylcholine Receptors Analyzed with Mutant Mice; Journal of Neuroscience 22:1208-1217 (2002).

Champtiaux et al.: Subunit composition of functional nicotinic receptors in dopaminergic neurons investigated with knock-out mice; Journal of Neuroscience 23:7820-7829 (2003).

Pons et al.: Crucial Role of α4 and α6 Nicotinic Acetylcholine Receptor Subunits from Ventral Tegmental Area in Systemic Nicotine Self-Administration; Journal of Neuroscience 28:12318-12327 (2008).

* cited by examiner

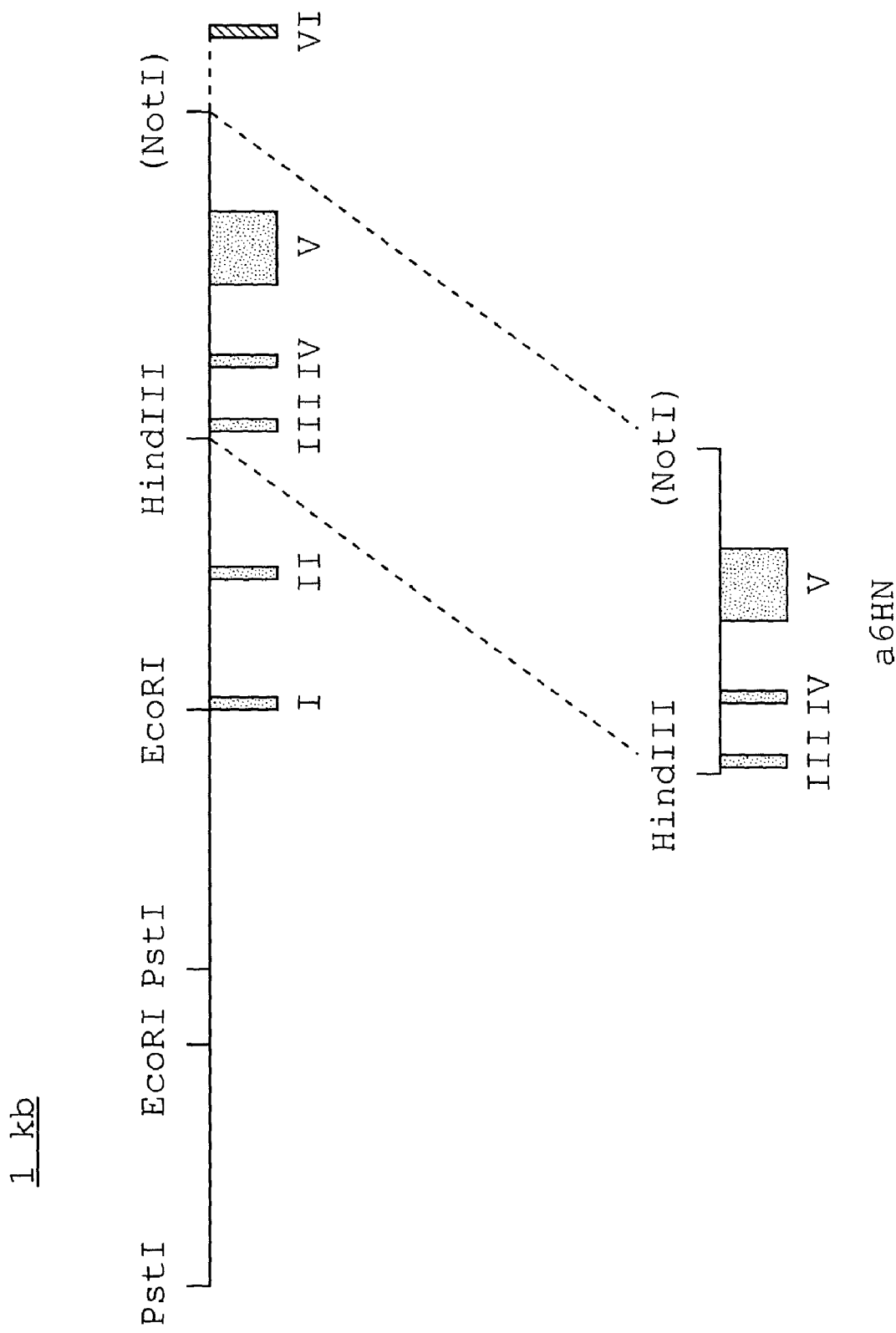

aGHN[1 to 4494]

```
aagctttatg ggccaaggtg gtgagaaaag attcacagag gaggtgaaat ccaaatgatc 60
tttgatcaat attttaagtc acatgtcatt tctaagtcaa cagagcagag gcaactggaa 120
acgttcggga tttctgttac agttaaatag ctttcatgca gtctccagtc ttcatgtctg 180
acttcattag cacggataac ttagatttgt ctattttag atataattct ctagttaaga 240
cttgtattag caagcacata gaagactgaa aaatattatt tcttccttcc aggatgaagt 300
caaccagatt atggagacca atctgtggct gcgtcacgta tgtgtccccc cctttgaatg 360
gcggcagaat gtatccactt agtgataaag ccacctgcat taactttttc gcaccccaac 420
ctatgataga taaagaatat ccttttcctt gctttctcct agtccttggg tcagctctgg 480
ttgcagttat attaatatag gcagcacatg ggcagagcct ggtgtctgac atggaaccct 540
ctggcctttc tcttttaagc tcccagttct ctttgtatca cttactgata ccaagnnnnn 600
nnnnnnnnnn nnnnnnnnnn nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnn nnnnnnnnnn 720
nnnnnnnnnn nnnnnnnnnn nnnnnnnnnn nnnnnnnnnn nnnnnnnnnn nnnnnnnnnn 780
nnnnnnnnnn nnnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnatctg gaaggactac agattgcgtt 1140
gggatccaac ggagtatgat ggcatcgaga cacttcgagt tccagcagac aacatctgga 1200
agcctgacat cgttctgtat aacnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnnnnnnn nnnnnnnnnn nnnnnnnnnn nnnnnnnnnn 1620
nnnnnnnnnn nnnnnnnnnn nnnnnnnnnn nnnnnnnnnn nnnnnnnnnn nnnnnnnnnn 1680
nnnnnnnnnn nnnnnnnnnn nnnnnnnnnn nnnnnnnnnn nnnnnnnnnn nnnnnnnnnn 1740
nnnnnnnnnn nnnnnnnnnn nnnnnnnnnn nnnnnnnnnn nnnnnnnnnn nnnnnnnnnn 1800
nnnnnnnnnn nnnnnnnnnn nnnnnnnnnn nnnnnnnnnn nnnnnnnnnn nnnnnnnnnn 1860
nnnnnnnnnn nnnnnnnnnn nnnnnnnnnn nnnnnnnnnn nnnnnnnnnn nnnnnnnnnn 1920
nnnnnnnnnn nnnnnnnnnn nnnnnnnnnn nnnnnnnnnn nnnnnnnnnn nnnnnnnnnn 1980
nnnnnnnnnn nnnnnnnnnn nnnnnnnnnn nnnnnnnnnn nnnnnnnnnn nnnnnnnnnn 2040
nnnnnnnnnn nnnnnnnnnn nnnnnnnnnn nnnnnnnnnn nnnnnnnnnn nnnnnnnnnn 2100
nnnnnnnnnn nnnnnnnnnn nnnnnnnnnn nnnnnnnnnn nnnnnnnnnn nnnnnnnnnn 2160
nnnnnnnnnn nnnnnnnnnn nnnnnnnnnn nnnnnnnnnn nnnnnnnnnn nnnnnnnnnn 2220
nnnnnnnnnn nnnnnnnnnn nnnnnnnnnn nnnnnnnnnn nnnnnnnnnn nnnnnnnnnn 2280
```

FIG. 3B (1)

```
nnnnnnaatg ctgtcggcga cttccaggtc gaaggcaaga ccaaagctct tctcaagtat 2340
gacggtgtga taacctggac cccaccagcc atctttaaga gctcctgccc aatggacatc 2400
accttcttcc cgtttgacca tcaaaactgc tccctgaagt ttggttcctg gacttatgac 2460
aaggcagaaa tcgaccttct catcattggc tctaaagtag acatgaacga cttttgggaa 2520
aacagtgaat gggaaattgt cgacgcctct ggctataagc atgacatcaa gtacaactgc 2580
tgtgaagaga tttacacgga cataacctac tccttctaca tcaggaggtt gcccatgttt 2640
tacaccatca acctcatcat cccctgcctc ttcatttcct tcctcacggt gctggttttt 2700
taccttccct ccgactgtgg cgagaaagtg actctttgca tctccgttct gctttctctc 2760
actgtctttt tgctggtgat tacagagacc atcccatcca catctctcgt gatcccactg 2820
gtgggtgagt atctactgtt caccatgatc tttgtcacgc tgtccattgt ggtgaccgtg 2880
ttcgtgctga acatacacta caggacccca gcaacgcata ccatgcccaa gtgggtgaag 2940
accatcttcc ttcaggcctt ccctcgatt ctgatgatga ggaaacctct ggacaagaca 3000
aaggaggcag gaggtgttaa ggaccccaaa agccatacca agaggcctgc caaggtcaaa 3060
tttactcatc gaggagaatc caaacttcta aaggaatgcc accactgcca aaaatcaagt 3120
gacatagcac ctggaaagag aagatcaagc cagcagcctg cacggtgggt ggcagagaat 3180
tcagagcact cgtccgatgt tgaagatgtc atcgagagtg ttcaattcat agcagaaaac 3240
atgaagagcc acaatgaaac aaacgaggta aaagtggagc ccttttctcc agccagctgc 3300
acccctagca ggcctacagg cactttagag actagtcaga gcgtcagtgg gagttacata 3360
tgtggaacag tcagggaccg tcacctaaga ccagctctat tatcatgaag ccttgtggga 3420
cctgggttca agtttaggga gctatagtga gaggatatat gtagtcctac aacaaatctt 3480
cagcctgcat ttacttacgg tgaggtctag ccacagtgca catgcaggac aagccttcct 3540
caaggaacaa gcctccaatg catcgaacac tgacaaagtg agggtgggaa gggagactgt 3600
agaaatcatt attaataaaa tcccaccggc gggcttgcta cctgctctaa tggtttgtgt 3660
tcccaaatga aacacacaca cacacacaca cacacacaca cagtctttgt 3720
gttttaatat gccgtataca gcacaatagc tgggccactg cctaccctcc atgctgttac 3780
tatacctccc gccaacaatc cccaagttat tacttactaa ttctatgtgc tatcttggtt 3840
gcccctagac ccagttgggc agcctctggg ccatgttttc cccggctatt tcaagtggtg 3900
gccatgtctc tctgtcctgc agtcttctca ggcctagcat ctcacctctt cctccacact 3960
ctcccggcat ggcagggtct cacttctcct cctcctcctc ctcctcctcc accacctcct 4020
ttctcctccc tccctcctcc ctcccctctt tcccctcccc ccttccttcc cagcctgaga 4080
actcctaaaa tcccacctct ccctgtcctt tccagctttg gctgttggca gctttattta 4140
ccaataagaa ccaactgcgg gcaggttccc agaaactaca ggcagacagt cccacgaaaa 4200
cagttttacg tggaccataa ttagcattca taatacgtgc agctacagag acacccaagg 4260
aaaagaagaa ctgtggtact gcctgaagcc ccagtggtga agatgcccc ttagcagtca 4320
gcagctccca tcacacttcc tctactagag ggggacccag acatgagtta aagacatctt 4380
gaagatgtgc tcagtatgca cacgtattcc gtgcctgtgt cccacactct aatgcctaga 4440
gcttggctcc tcctaccccca agcaagtgct caaggatagg gagatcgcgg ccgc    4494
```

FIG. 3B (2)

a6EH [1 to 4006]

```
gaattcagag agcttttatc atgctgaaca gccgggacca gggaaacctg cactccggtt   60
tatgtctgtg gctatgtgga ttcctggctc tctttaaagg tgagttatta cggcttatat  120
cctagaatac aattggtagt gtgcatttcc tcttctttct catcttgtct ggatccaaat  180
aattagagga ctttaattag ttaggcttaa cctaacagat atgatttgga aagtaaggta  240
gagaaaacat tgaagtacag tataatattc atacttcatc tctccaacta aaatatgctt  300
ttccaattag catacaaaat catctgcttt tgtagccatg tatgctacca atatgcttca  360
tttacttacg gtaatttgtt agctgggact tattagcctg cgagtcctac caatgtgtgt  420
aattgtcctc acttaggaaa cctgtcttat tgtctactaa gagtgagctt tcctgtctta  480
aaagttggct cagacctggc tggtgcacac acacacacac acacacacac acacacacac  540
acacacacga acaggcacac atgcacacat ctcggatgag gtttcagggg gtgctgatgg  600
tgagctccag agagaggaaa cagtagcaac agccaagaga gctcactatc ttctgaaaca  660
atgttttcat cctggttagt tacacaggag agaatgacag nnnnnnnnnn nnnnnnnnnn  720
nnnnnnnnnn nnnnnnnnnn nnnnnnnnnn nnnnnnnnnn nnnnnnnnnn nnnnnnnnnn  780
nnnnnnnnnn nnnnnnnnnn nnnnnnnnnn nnnnnnnnnn nnnnnnnnnn nnnnnnnnnn  840
nnnnnnnnnn nnnnnnnnnn nnnnnnnnnn nnnnnnnnnn nnnnnnnnnn nnnnnnnnnn  900
nnnnnnnnnn nnnnnnnnnn nnnnnnnnnn nnnnnnnnnn nnnnnnnnnn nnnnnnnnnn  960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnnnnnnn nnnnnnnnnn nnnnnnnnnn nnnnnnnnnn 1620
nnnnnnnnnn nnnnnnnnnn nnnnnnnnnn nnnnnnnnnn nnnnnnnnnn nnnnnnnnnn 1680
nnnnnnnnnn nnnnnnnnnn nnnnnnnnnn nnnnnnnnnn nnnnnnnnnn nnnnnnnnnn 1740
nnnnnnnnnn nnnnnnnnnn nnnnnnnnnn nnnnnnnnnn nnnnnnnnnn nnnnnnnnnn 1800
nnnnnnnnnn nnnnnnnnnn nnnnnnnnnn nnnnnnnnnn nnnnnnnnnn gcagtacagg 1860
ctgtgaatct gaagagcagc tcttccacag gctgtttgct cactacaacc gcttcatccg 1920
gccggtggag aatgtctccg atcccgtcac ggtgcatctt gaattggcaa tcacgcaact 1980
ggccaatgtg nnnnnnnnnn nnnnnnnnnn nnnnnnnnnn nnnnnnnnnn nnnnnnnnnn 2040
nnnnnnnnnn nnnnnnnnnn nnnnnnnnnn nnnnnnnnnn nnnnnnnnnn nnnnnnnnnn 2100
nnnnnnnnnn nnnnnnnnnn nnnnnnnnnn nnnnnnnnnn nnnnnnnnnn nnnnnnnnnn 2160
nnnnnnnnnn nnnnnnnnnn nnnnnnnnnn nnnnnnnnnn nnnnnnnnnn nnnnnnnnnn 2220
```

FIG. 4B(1)

```
nnnnnnnnnn nnnnnnnnnn nnnnnnnnnn nnnnnnnnnn nnnnnnnnnn nnnnnnnnnn 2280
nnnnnnnnnn nnnnnnnnnn nnnnnnnnnn nnnnnnnnnn nnnnnnnnnn nnnnnnnnnn 2340
nnnnnnnnnn nnnnnnnnnn nnnnnnnnnn nnnnnnnnnn nnnnnnnnnn nnnnnnnnnn 2400
nnnnnnnnnn nnnnnnnnnn nnnnnnnnnn nnnnnnnnnn nnnnnnnnnn nnnnnnnnnn 2460
nnnnnnnnnn nnnnnnnnnn nnnnnnnnnn nnnnnnnnnn nactccctgg gctgagcata 2520
tacaaaccat cacaccatgt ctgccagttg attgcagctt ttccagaaac tagtgcattt 2580
gaaaccatga ttcaaaattg ttcacctggg tgtcaactaa tattttcccg ataaagaggt 2640
ctaggctaat ggttccaaca acgtggtgtg gtactgtgtg tctctggcct cctcctccat 2700
tagggctcac tgagctcagt gtccattgaa atggtctgga gttgcatgaa gactatgatt 2760
tttccagagt aggtcctgac tcatgacatt ttctaacacc tccaaggttg tgtattcccc 2820
atgaatacac accatatgga gcctatccaa accatggaag tgtctcaagg gaggcaggcc 2880
tgttaagaat ggtactgata attagtgtca actccctgaa ctcacccagg ttttgaagac 2940
tatgacaggt ttaggccagt tacctctaag acctcacgga agtgaggcag cagagcctat 3000
ccagctttga ccaacagcta gtacatactt acccagcatc tgttagaccc tacagattca 3060
aggcgactca ataccagagg gccctaatca atagagggga atcactggga agctgtgcag 3120
gctccatttt cctaagtctt tttgttgact ttaccaatcc cagggcctgt gttggctcca 3180
catgacccac tggcagggag aagcttnnnn nnnnnnnnnn nnnnnnnnnn nnnnnnnnnn 3240
nnnnnnnnnn nnnnnnnnnn nnnnnnnnnn nnnnnnnnnn nnnnnnnnnn nnnnnnnnnn 3300
nnnnnnnnnn nnnnnnncct gcgtagaaac ctcaaccagg ctgggatcct tcactcacag 3360
ggacctcaga tgtcttggaa aatgaaattt tgaatcccct gctgactgct aagaacctac 3420
tattaatacc caagctattc tgctgtgacc tgtcacctgt cctgactctc cttatgtcac 3480
ttcagggact gcttggacag taactcttca aagaagcctc cttgactcgt atattaaata 3540
gatgtgtgca tacacgcagg aatcactcca cctctcttgt tatatcatga tgtgttttat 3600
gctggcgtac acatttatta ttagctctgt ctttccaacc acaacagcta agagcacatg 3660
aaggcaggag ctttcttcac tctgtaactt gagtggaact ctgtaacaca gtggtcactg 3720
ggtaagtagg aatatcccctt gtgactgaag ggcccgtgag ctgggaaagg gaatacagag 3780
ggagtgagta cctggtttca actggcaaac ttgcatgtga actaaactgc tgtttcagtt 3840
tggatcccag ggcaaatgca cacagtacat cccaggcttc tttgaggaaa ggccatgggg 3900
atagataaaa acagtgagta cctgtcgcca cctacaggac tctcccctct gtcgtccctg 3960
aacctctgcc ctcctccctg ttaccttttca tgcatctagg aagctt         4006
```

FIG. 4B(2)

5023 bp sequence

```
ctgcaggaat tcttaggcaa atggatggaa ctagaaaata tcatcctgag tgaggtaacc 60
caatcacaaa agaacataca tggtatgcac tcactgataa gtggatatta cccccaaagt 120
ttggaatatc caagatacaa ttcacagacc aaatgaagct caagaagaag gaagaacaaa 180
gtatggatac ttcagtcttt cttagaaggg ggaacaaaat actcatggga ggagatacag 240
agacaaagtg tggagcagag actgaaggaa aagccattca gagactgccc cagctgggga 300
tccatcccat atacagtcac caaacccaga cactattgtt gatgccaaca agtgcatgct 360
gacaggagtc tgacatagct gtctcctgag aggctctgcc agtgcctgac aaatatagag 420
gggatgctca cagccaacca ctggactgag cacagggtcc tcaatggagg agttagagaa 480
aggactgaag gaccagaaga ggtttgcagc cccataggag gaacaacaat atgaactagc 540
cagtatcccc agagctccca gggactaagc caccaaccaa agagtacata tgcaggaacc 600
catggctcca gctgcatatg tagcagagga tgtcacttct caatgggagg agaggcccct 660
ggtcctgaga aggctcaatg ccccagtgta ggggaatgcc aagacaggga agtgggagtg 720
tgtgggttgg tgagcagggg ggaggaggaa aggagtaggg ggtctttgga ggggaaacca 780
ggaaaggaga taacatttga aatgtaaatg aagaaaatat ctaattttt aagaaagaaa 840
aaagacaatt acagacttag ctgtgcctgt agccactgtt ctcctagagt tcagagcctg 900
cctgtctggg accagacacc tctggctgag gtttcttgcc tggcattatg tgcagggtcc 960
ggctccattt tctcacccag ccctgccttc cacagctctg tgcacaggag aggatccaag 1020
gagaagggaa gtggaggtgg tggcgacagt gacccagttc agaaaggact ctgaggcaca 1080
ttcaatctat aaagtattca tggctctaaa agccttccaa ggggatccaa agcatttgct 1140
gagctgcagn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnnnnnnn nnnnnnnnnn nnnnnnnnnn nnnnnnnnnn 1620
nnnnnnnnnn nnnnnnnnnn nnnnnnnnnn nnnnnnnnnn nnnnnnnnnn nnnnnnnnnn 1680
nnnnnnnnnn nnnnnnnnnn nnnnnnnnnn nnnnnnnnnn nnnnnnnnnn nnnnnnnnnn 1740
nnnnnnnnnn nnnnnnnnnn nnnnnnnnnn nnnnnnnnnn nnnnnnnnnn nnnnnnnnnn 1800
nnnnnnnnnn nnnnnnnnnn nnnnnnnnnn nnnnnnnnnn nnnnnnnnnn nnnnnnnnnn 1860
nnnnnnnnnn nnnnnnnnnn nnnnnnnnnn nnnnnnnnnn nnnnnnnnnn nnnnnnnnnn 1920
nnnnnnnnnn nnnnnnnnnn nnnnnnnnnn nnnnnnnnnn nnnnnnnnnn nnnnnnnnnn 1980
nnnnnnnnnn nnnnnnnnnn nnnnnnnnnn nnnnnnnnnn nnnnnnnnnn nnnnnnnnnn 2040
```

FIG. 5B(1)

nnnnnnnnnn nnnnnnnnnn nnnnnnnnnn nnnnnnnnnn nnnnnnnnnn nnnnnnnnnn 2100
nnnnnnnnnn nnnnnnnnnn nnnnnnnnnn nnnnnnnnnn nnnnnnnnnn nnnnnnnnnn 2160
nnnnnnnnnn nnnnnnnnnn nnnnnnnnnn nnnnnnnnnn nnnnnnnnnn nnnnnnnnnn 2220
nnnnnnnnnn nnnnnnnnnn nnnnnnnnnn nnnnnnnnnn nnnnnnnnnn nnnnnnnnnn 2280
nnnnnnnnnn nnnnnnnnnn nnnnnnnnnn nnnnnnnnnn nnnnnnnnnn nnnnnnnnnn 2340
nnnnnnnnnn nnnnnnnnnn nnnnnnnnnn nnnnnnnnnn nnnnnnnnnn nnnnnnnnnn 2400
nnnnnnnnnn nnnnnnnnnn nnnnnnnnnn nnnnnnnnnn nnnnnnnnnn nnnnnnnnnn 2460
nnnnnnnnnn nnnnnnnnnn nnnnnnnnnn nnnnnnnnnn nnnnnnnnnn nnnnnnnnnn 2520
nnnnnnnnnn nnnnnnnnnn nnnnnnnnnn nnnnnnnnnn nnnnnnnnnn nnnnnnnnnn 2580
nnnnnnnnnn nnnnnnnnnn nnnnnnnnnn nnnnnnnnnn nnnnnnnnnn nnnnnnnnnn 2640
nnnnnnnnnn nnnnnnnnnn nnnnnnnnnn nnnnnnnnnn nnnnnnnnnn nnnnnnnnnn 2700
nnnnnnnnnn nnnnnnnnnn nnnnnnnnnn nnnnnnnnnn nnnnnnnnnn nnnnnnnnnn 2760
nnnnnnnnnn nnnnnnnnnn nnnnnnnnnn nnnnnnnnnn nnnnnnnnnn nnnnnnnnnn 2820
nnnnnnnnnn nnnnnnnnnn nnnnnnnnnn nnnnnnnnnn nnnnnnnnnn nnnnnnnnnn 2880
nnnnnnnnnn nnnnnnnnnn nnnnnnnnnn nnnnnnnnnn nnnnnnnnnn nnnnnnnnnn 2940
nnnnnnnnnn nnnnnnnnnn nnnnnnnnnn nnnnnnnnnn nnnnnnnnnn nnnnnnnnnn 3000
nnnnnnnnnn nnnnnnnnnn nnnnnnnnnn nnnnnnnnnn nnnnnnnnnn nnnnnnnnnn 3060
nnnnnnnnnn nnnnnnnnnn nnnnnnnnnn nnnnnnnnnn nnnnnnnnnn nnnnnnnnnn 3120
nnnnnnnnnn nnnnnnnnnn nnnnnnnnnn nnnnnnnnnn nnnnnnnnnn nnnnnnnnnn 3180
nnnnnnnnnn nnnnnnnnnn nnnnnnnnnn nnnnnnnnnn nnnnnnnnnn nnnnnnnnnn 3240
nnnnnnnnnn nnnnnnnnnn nnnnnnnnnn nnnnnnnnnn nnnnnnnnnn nnnnnnnnnn 3300
nnnnnnnnnn nnnnnnnnnn nnnnnnnnnn nnnnnnnnnn nnnnnnnnnn nnnnnnnnnn 3360
nnnnnnnnnn nnnnnnnnnn nnnnnnnnnn nnnnnnnnnn nnnnnnnnnn nnnnnnnnnn 3420
nnnnnnnnnn nnnnnnnnnn nnnnnnnnnn nnnnnnnnnn nnnnnnnnnn nnnnnnnnnn 3480
nnnnnnnnnn nnnnnnnnnn nnnnnnnnnn nnnnnnnnnn nnnnnnnnnn nnnnnnnnnn 3540
nnnnnnnnnn nnnnnnnnnn nnnnnnnnnn nnnnnnnnnn nnnnnnnnnn nnnnnnnnnn 3600
nnnnnnnnnn nnnnnnnnnn nnnnnnnnnn nnnnnnnnnn nnnnnnnnnn nnnnnnnnnn 3660
nnnnnnnnnn nnnnnnnnnn nnnnnnnnnn nnnnnnnnnn nnnnnnnnnn nnnnnnnnnn 3720
nnnnnnnnnn nnnnnnnnnn nnnnnnnnnn nnnnnnnnnn nnnnnnnnnn nnnnnnnnnn 3780
nnnnnnnnnn nnnnnnnnnn nnnnnnnnnn nnnnnnnnnn nnnnnnnnnn nnnnnnnnnn 3840
nnnnnnnnnn nnnnnnnnnn nnnnnnnnnn nnnnnnnnnn nnnnnnnnnn nnnnnnnnnn 3900
nnnnnnnnnn nnnnnnnnnn nnnnnnnnnn nnnnnnnnnn nnnnnnnnnn nnnnnnnnnn 3960
nnnnnnnnnn nnnnnnnnnn nnnnnnnnnn nnnnnnnnnn nnnnnnnnnn nnnnnnnnnn 4020
nnnnnnnnnn nnnnnnnnnn nnnnnnnnnn nnnnnnnnnn nnnnnnnnnn nnnnnnnnnn 4080
nnnnnnnnnn nnnnnnnnnn nnnnnnnnnn nnnnnnnnnn nnnnnnnnnn nnnnnnnnnn 4140

FIG. 5B(2)

```
nnnnnnnnnn nnnnnnnnnn nnnnnnnnnn nnnnnnnnnn nnnnnnnnnn nnnnnnnnnn 4200
nnnnnnnnnn nnnnnnnnnn nnnnnnnnnn nnnnnnnnnn nnnnnnnnnn nnnnnnnnnn 4260
nnnnnnnnnn nnnnnnnnnn nnnnnnnnnn nnnnnnnnnn nnnnnnnnnn naactaggaa 4320
tatttcagac agatgcctaa ctgctaaggc tcagagaaac agcaaattaa gtggatatcc 4380
tttatggatg actgtgattt tcttttccta taatggaagc caagtaaata agatgctatt 4440
atcccactaa aagcagcggt tctcaacctc tgggtctcca ccccttgagg tcaaatgaca 4500
cttttaccga gggtcatcta agacattgga aaacacagat atttacatta tgactcacaa 4560
ccgtagaaaa attacactta tgaagtagca acgaactaat tttatccttg aggaataggg 4620
ggggtcacca caacatgcag atctgtatta aagggttgca gcattaggaa ggtttagaac 4680
cactgcccta agagtaggca agactgcagg tctctcatgg gacttgcctg tttgcctagt 4740
gtctcagcct gcctctcttc ttccctgcac agaggtctag ggtgacagga catgtgacag 4800
ccagccgagt gaagcagcag ggttggcttc ccttgcccct cacatctgtt tcagcctggg 4860
atgcagggag cagttgcatg atgtcccgtg ttttcacttc acagaagatc tgtgtgagct 4920
tccaggagct tcccgggggct ttcaatatct gattctggca gctgacagac agctgtgtct 4980
tccacagccc tccgtgtaga aatcggaatt cgatatcaag ctt         5023
```

FIG. 5B(3)

a6PP [1 to 4500]
4500pb

```
ctgcagaagc agcattaaga ctgtgctcta aatccaactc ctactttcct tggaagagac  60
acaagaaaaa gaggcaaggt gacagggcac agacaaagca ctgtagctac agatgcagag 120
atctgaatta ggaaactcta agccaaggca cacctggaat catcaatagc tggaaaagac 180
aagaaagatt ttctgtcaga gcctacagga aagtctggct ttgctaacac ctgcatttg 240
ggccattagc ctcagagctc tgaaatgata atatttgtt gtatttaccc accaaatttg 300
tggtgattta ttatgaggtc sstaggaaat aaataggact tggtatagtt tttttttttt 360
ttttcatttc caatcacaaa gcaagaatta ctgcaatgga attaaatttt atttcacaga 420
attgctggtt ctagtacaat ggtaccgatg ctgaaattgt ttctacatca ggagacttac 480
agtttaggca catttatttg tatgttgaag accccagata attactttga aaaagagaa 540
gtcaagaggc tggaatggag ttccagaatc cccagaatct tgtcttggaa accatttcca 600
ctacaggatg tccttcactg aagttgctga gtggtgccca tgcaggacta atgaatccac 660
tgaaagctgt gtggcttaac tggagannnn nnnnnnnnnn nnnnnnnnnn nnnnnnnnnn 720
nnnnnnnnnn nnnnnnnnnn nnnnnnnnnn nnnnnnnnnn nnnnnnnnnn nnnnnnnnnn 780
nnnnnnnnnn nnnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnnnnnnn nnnnnnnnnn nnnnnnnnnn nnnnnnnnnn 1620
nnnnnnnnnn nnnnnnnnnn nnnnnnnnnn nnnnnnnnnn nnnnnnnnnn nnnnnnnnnn 1680
nnnnnnnnnn nnnnnnnnnn nnnnnnnnnn nnnnnnnnnn nnnnnnnnnn nnnnnnnnnn 1740
nnnnnnnnnn nnnnnnnnnn nnnnnnnnnn nnnnnnnnnn nnnnnnnnnn nnnnnnnnnn 1800
nnnnnnnnnn nnnnnnnnnn nnnnnnnnnn nnnnnnnnnn nnnnnnnnnn nnnnnnnnnn 1860
nnnnnnnnnn nnnnnnnnnn nnnnnnnnnn nnnnnnnnnn nnnnnnnnnn nnnnnnnnnn 1920
nnnnnnnnnn nnnnnnnnnn nnnnnnnnnn nnnnnnnnnn nnnnnnnnnn nnnnnnnnnn 1980
nnnnnnnnnn nnnnnnnnnn nnnnnnnnnn nnnnnnnnnn nnnnnnnnnn nnnnnnnnnn 2040
nnnnnnnnnn nnnnnnnnnn nnnnnnnnnn nnnnnnnnnn nnnnnnnnnn nnnnnnnnnn 2100
nnnnnnnnnn nnnnnnnnnn nnnnnnnnnn nnnnnnnnnn nnnnnnnnnn nnnnnnnnnn 2160
nnnnnnnnnn nnnnnnnnnn nnnnnnnnnn nnnnnnnnnn nnnnnnnnnn nnnnnnnnnn 2220
```

FIG. 6B(1)

```
nnnnnnnnnn nnnnnnnnnn nnnnnnnnnn nnnnnnnnnn nnnnnnnnnn nnnnnnnnnn 2280
nnnnnnnnnn nnnnnnnnnn nnnnnnnnnn nnnnnnnnnn nnnnnnnnnn nnnnnnnnnn 2340
nnnnnnnnnn nnnnnnnnnn nnnnnnnnnn nnnnnnnnnn nnnnnnnnnn nnnnnnnnnn 2400
nnnnnnnnnn nnnnnnnnnn nnnnnnnnnn nnnnnnnnnn nnnnnnnnnn nnnnnnnnnn 2460
nnnnnnnnnn nnnnnnnnnn nnnnnnnnnn nnnnnnnnnn nnnnnnnnnn nnnnnnnnnn 2520
nnnnnnnnnn nnnnnnnnnn nnnnnnnnnn nnnnnnnnnn nnnnnnnnnn nnnnnnnnnn 2580
nnnnnnnnnn nnnnnnnnnn nnnnnnnnnn nnnnnnnnnn nnnnnnnnnn nnnnnnnnnn 2640
nnnnnnnnnn nnnnnnnnnn nnnnnnnnnn nnnnnnnnnn nnnnnnnnnn nnnnnnnnnn 2700
nnnnnnnnnn nnnnnnnnnn nnnnnnnnnn nnnnnnnnnn nnnnnnnnnn nnnnnnnnnn 2760
nnnnnnnnnn nnnnnnnnnn nnnnnnnnnn nnnnnnnnnn nnnnnnnnnn nnnnnnnnnn 2820
nnnnnnnnnn nnnnnnnnnn nnnnnnnnnn nnnnnnnnnn nnnnnnnnnn nnnnnnnnnn 2880
nnnnnnnnnn nnnnnnnnnn nnnnnnnnnn nnnnnnnnnn nnnnnnnnnn nnnnnnnnnn 2940
nnnnnnnnnn nnnnnnnnnn nnnnnnnnnn nnnnnnnnnn nnnnnnnnnn nnnnnnnnnn 3000
nnnnnnnnnn nnnnnnnnnn nnnnnnnnnn nnnnnnnnnn nnnnnnnnnn nnnnnnnnnn 3060
nnnnnnnnnn nnnnnnnnnn nnnnnnnnnn nnnnnnnnnn nnnnnnnnnn nnnnnnnnnn 3120
nnnnnnnnnn nnnnnnnnnn nnnnnnnnnn nnnnnnnnnn nnnnnnnnnn nnnnnnnnnn 3180
nnnnnnnnnn nnnnnnnnnn nnnnnnnnnn nnnnnnnnnn nnnnnnnnnn nnnnnnnnnn 3240
nnnnnnnnnn nnnnnnnnnn nnnnnnnnnn nnnnnnnnnn nnnnnnnnnn nnnnnnnnnn 3300
nnnnnnnnnn nnnnnnnnnn nnnnnnnnnn nnnnnnnnnn nnnnnnnnnn nnnnnnngaa 3360
ttcttaggca aatggatgga actagaaaat atcatcctga gtgaggtaac ccaatcacaa 3420
aagaacatac atggtatgca ctcactgata agtggatatt accccaaag tttggaatat 3480
ccaagataca attcacagac caaatgaagc tcaagaagaa ggaagaacaa agtatggata 3540
cttcagtctt tcttagaagg gggaacaaaa tactcatggg aggagataca gagacaaagt 3600
gtggagcaga gactgaagga aaagccattc agagactgcc ccagctgggg atccatccca 3660
tatacagtca ccaaacccag acactattgt tgatgccaac aagtgcatgc tgacaggagt 3720
ctgacatagc tgtctcctga gaggctctgc cagtgcctga caaatataga ggggatgctc 3780
acagccaacc actggactga gcacagggtc tcaatggag gagttagaga aaggactgaa 3840
ggaccagaag aggtttgcag ccccatagga ggaacaacaa tatgaactag ccagtatccc 3900
cagagctccc agggactaag ccaccaacca aagagtacat atgcaggaac ccatggctcc 3960
agctgcatat gtagcagagg atgtcacttc tcaatgggag gagaggccct tggtcctgag 4020
aaggctcaat gccccagtgt aggggaatgc caagacaggg aagtgggagt gtgtgggttg 4080
gtgagcaggg gggaggagga aaggagtagg gggtctttgg aggggaaacc aggaaaggag 4140
ataacatttg aaatgtaaat gaagaaaata tctaattttt taagaaagaa aaaagacaat 4200
tacagactta gctgtgcctg tagccactgt tctcctagag ttcagagcct gcctgtctgg 4260
gaccagacac ctctggctga ggtttcttgc ctggcattat gtgcagggtc cggctccatt 4320
ttctcaccca gccctgcctt ccacagctct gtgcacagga gaggatccaa ggagaaggga 4380
agtggaggtg gtggcgacag tgacccagtt cagaaaggac tctgaggcac attcaatcta 4440
taaagtattc atggctctaa aagccttcca aggggatcca agcatttgc tgagctgcag 4500
```

FIG. 6B(2)

ctgcagaagc agcattaaga ctgtgctcta atccaactc ctactttcct tggaagagac 60
acaagaaaaa gaggcaaggt gacagggcac agacaaagca ctgtagctac agatgcagag 120
atctgaatta ggaaactcta agccaaggca cacctggaat catcaatagc tggaaaagac 180
aagaaagatt ttctgtcaga gcctacagga aagtctggct ttgctaacac ctgcattttg 240
ggccattagc ctcagagctc tgaaatgata atattttgtt gtatttaccc accaaatttg 300
tggtgattta ttatgaggtc sstaggaaat aaataggact tggtatagtt tttttttttt 360
ttttcatttc caatcacaaa gcaagaatta ctgcaatgga attaaatttt atttcacaga 420
attgctggtt ctagtacaat ggtaccgatg ctgaaattgt ttctacatca ggagacttac 480
agtttaggca catttatttg tatgttgaag accccagata attactttga aaaaagagaa 540
gtcaagaggc tggaatggag ttccagaatc cccagaatct tgtcttggaa accatttcca 600
ctacaggatg tccttcactg aagttgctga gtggtgccca tgcaggacta atgaatccac 660
tgaaagctgt gtggcttaac tggagannnn nnnnnnnnnn nnnnnnnnnn nnnnnnnnnn 720
nnnnnnnnnn nnnnnnnnnn nnnnnnnnnn nnnnnnnnnn nnnnnnnnnn nnnnnnnnnn 780
nnnnnnnnnn nnnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnnnnnnn nnnnnnnnnn nnnnnnnnnn nnnnnnnnnn 1620
nnnnnnnnnn nnnnnnnnnn nnnnnnnnnn nnnnnnnnnn nnnnnnnnnn nnnnnnnnnn 1680
nnnnnnnnnn nnnnnnnnnn nnnnnnnnnn nnnnnnnnnn nnnnnnnnnn nnnnnnnnnn 1740
nnnnnnnnnn nnnnnnnnnn nnnnnnnnnn nnnnnnnnnn nnnnnnnnnn nnnnnnnnnn 1800
nnnnnnnnnn nnnnnnnnnn nnnnnnnnnn nnnnnnnnnn nnnnnnnnnn nnnnnnnnnn 1860
nnnnnnnnnn nnnnnnnnnn nnnnnnnnnn nnnnnnnnnn nnnnnnnnnn nnnnnnnnnn 1920
nnnnnnnnnn nnnnnnnnnn nnnnnnnnnn nnnnnnnnnn nnnnnnnnnn nnnnnnnnnn 1980
nnnnnnnnnn nnnnnnnnnn nnnnnnnnnn nnnnnnnnnn nnnnnnnnnn nnnnnnnnnn 2040
nnnnnnnnnn nnnnnnnnnn nnnnnnnnnn nnnnnnnnnn nnnnnnnnnn nnnnnnnnnn 2100
nnnnnnnnnn nnnnnnnnnn nnnnnnnnnn nnnnnnnnnn nnnnnnnnnn nnnnnnnnnn 2160
nnnnnnnnnn nnnnnnnnnn nnnnnnnnnn nnnnnnnnnn nnnnnnnnnn nnnnnnnnnn 2220

FIG. 9(1)

```
nnnnnnnnnn nnnnnnnnnn nnnnnnnnnn nnnnnnnnnn nnnnnnnnnn nnnnnnnnnn 2280
nnnnnnnnnn nnnnnnnnnn nnnnnnnnnn nnnnnnnnnn nnnnnnnnnn nnnnnnnnnn 2340
nnnnnnnnnn nnnnnnnnnn nnnnnnnnnn nnnnnnnnnn nnnnnnnnnn nnnnnnnnnn 2400
nnnnnnnnnn nnnnnnnnnn nnnnnnnnnn nnnnnnnnnn nnnnnnnnnn nnnnnnnnnn 2460
nnnnnnnnnn nnnnnnnnnn nnnnnnnnnn nnnnnnnnnn nnnnnnnnnn nnnnnnnnnn 2520
nnnnnnnnnn nnnnnnnnnn nnnnnnnnnn nnnnnnnnnn nnnnnnnnnn nnnnnnnnnn 2580
nnnnnnnnnn nnnnnnnnnn nnnnnnnnnn nnnnnnnnnn nnnnnnnnnn nnnnnnnnnn 2640
nnnnnnnnnn nnnnnnnnnn nnnnnnnnnn nnnnnnnnnn nnnnnnnnnn nnnnnnnnnn 2700
nnnnnnnnnn nnnnnnnnnn nnnnnnnnnn nnnnnnnnnn nnnnnnnnnn nnnnnnnnnn 2760
nnnnnnnnnn nnnnnnnnnn nnnnnnnnnn nnnnnnnnnn nnnnnnnnnn nnnnnnnnnn 2820
nnnnnnnnnn nnnnnnnnnn nnnnnnnnnn nnnnnnnnnn nnnnnnnnnn nnnnnnnnnn 2880
nnnnnnnnnn nnnnnnnnnn nnnnnnnnnn nnnnnnnnnn nnnnnnnnnn nnnnnnnnnn 2940
nnnnnnnnnn nnnnnnnnnn nnnnnnnnnn nnnnnnnnnn nnnnnnnnnn nnnnnnnnnn 3000
nnnnnnnnnn nnnnnnnnnn nnnnnnnnnn nnnnnnnnnn nnnnnnnnnn nnnnnnnnnn 3060
nnnnnnnnnn nnnnnnnnnn nnnnnnnnnn nnnnnnnnnn nnnnnnnnnn nnnnnnnnnn 3120
nnnnnnnnnn nnnnnnnnnn nnnnnnnnnn nnnnnnnnnn nnnnnnnnnn nnnnnnnnnn 3180
nnnnnnnnnn nnnnnnnnnn nnnnnnnnnn nnnnnnnnnn nnnnnnnnnn nnnnnnnnnn 3240
nnnnnnnnnn nnnnnnnnnn nnnnnnnnnn nnnnnnnnnn nnnnnnnnnn nnnnnnnnnn 3300
nnnnnnnnnn nnnnnnnnnn nnnnnnnnnn nnnnnnnnnn nnnnnnnnnn nnnnnngaa 3360
ttcttaggca aatggatgga actagaaaat atcatcctga gtgaggtaac ccaatcacaa 3420
aagaacatac atggtatgca ctcactgata agtggatatt accccccaaag tttggaatat 3480
ccaagataca attcacagac caaatgaagc tcaagaagaa ggaagaacaa agtatggata 3540
cttcagtctt tcttagaagg gggaacaaaa tactcatggg aggagataca gagacaaagt 3600
gtggagcaga gactgaagga aaagccattc agagactgcc ccagctgggg atccatccca 3660
tatacagtca ccaaacccag acactattgt tgatgccaac aagtgcatgc tgacaggagt 3720
ctgacatagc tgtctcctga gaggctctgc cagtgcctga caaatataga ggggatgctc 3780
acagccaacc actggactga gcacagggtc ctcaatggag gagttagaga aaggactgaa 3840
ggaccagaag aggtttgcag ccccatagga ggaacaacaa tatgaactag ccagtatccc 3900
cagagctccc agggactaag ccaccaacca aagagtacat atgcaggaac ccatggctcc 3960
agctgcatat gtagcagagg atgtcacttc tcaatgggag gagaggccct tggtcctgag 4020
aaggctcaat gccccagtgt aggggaatgc caagacaggg aagtgggagt gtgtgggttg 4080
gtgagcaggg gggaggagga aaggagtagg gggtctttgg aggggaaacc aggaaaggag 4140
ataacatttg aaatgtaaat gaagaaaata tctaattttt taagaaagaa aaaagacaat 4200
tacagactta gctgtgcctg tagccactgt tctcctagag ttcagagcct gcctgtctgg 4260
gaccagacac ctctggctga ggtttcttgc ctggcattat gtgcagggtc cggctccatt 4320
ttctcaccca gccctgcctt ccacagctct gtgcacagga gaggatccaa ggagaaggga 4380
agtggaggtg gtggcgacag tgacccagtt cagaaaggac tctgaggcac attcaatcta 4440
taaagtattc atggctctaa aagccttcca aggggatcca aagcatttgc tgagctgcag 4500
```

FIG. 9(2)

```
nnnnnnnnnn nnnnnnnnnn nnnnnnnnnn nnnnnnnnnn nnnnnnnnnn nnnnnnnnnn 4560
nnnnnnnnnn nnnnnnnnnn nnnnnnnnnn nnnnnnnnnn nnnnnnnnnn nnnnnnnnnn 4620
nnnnnnnnnn nnnnnnnnnn nnnnnnnnnn nnnnnnnnnn nnnnnnnnnn nnnnnnnnnn 4680
nnnnnnnnnn nnnnnnnnnn nnnnnnnnnn nnnnnnnnnn nnnnnnnnnn nnnnnnnnnn 4740
nnnnnnnnnn nnnnnnnnnn nnnnnnnnnn nnnnnnnnnn nnnnnnnnnn nnnnnnnnnn 4800
nnnnnnnnnn nnnnnnnnnn nnnnnnnnnn nnnnnnnnnn nnnnnnnnnn nnnnnnnnnn 4860
nnnnnnnnnn nnnnnnnnnn nnnnnnnnnn nnnnnnnnnn nnnnnnnnnn nnnnnnnnnn 4920
nnnnnnnnnn nnnnnnnnnn nnnnnnnnnn nnnnnnnnnn nnnnnnnnnn nnnnnnnnnn 4980
nnnnnnnnnn nnnnnnnnnn nnnnnnnnnn nnnnnnnnnn nnnnnnnnnn nnnnnnnnnn 5040
nnnnnnnnnn nnnnnnnnnn nnnnnnnnnn nnnnnnnnnn nnnnnnnnnn nnnnnnnnnn 5100
nnnnnnnnnn nnnnnnnnnn nnnnnnnnnn nnnnnnnnnn nnnnnnnnnn nnnnnnnnnn 5160
nnnnnnnnnn nnnnnnnnnn nnnnnnnnnn nnnnnnnnnn nnnnnnnnnn nnnnnnnnnn 5220
nnnnnnnnnn nnnnnnnnnn nnnnnnnnnn nnnnnnnnnn nnnnnnnnnn nnnnnnnnnn 5280
nnnnnnnnnn nnnnnnnnnn nnnnnnnnnn nnnnnnnnnn nnnnnnnnnn nnnnnnnnnn 5340
nnnnnnnnnn nnnnnnaagc ttnnnnnnnn nnnnnnnnnn nnnnnnnnnn nnnnnnnnnn 5400
nnnnnnnnnn nnnnnnnnnn nnnnnnnnnn nnnnnnnnnn nnnnnnnnnn nnnnnnnnnn 5460
nnnnnnnnnn nnnnnnnnnn nnnnnnnnnn nnnnnnnnnn nnnnnnnnnn nnnnnnnnnn 5520
nnnnnnnnnn nnnnnnnnnn nnnnnnnnnn nnnnnnnnnn nnnnnnnnnn nnnnnnnnnn 5580
nnnnnnnnnn nnnnnnnnnn nnnnnnnnnn nnnnnnnnnn nnnnnnnnnn nnnnnnnnnn 5640
nnnnnnnnnn nnnnnnnnnn nnnnnnnnnn nnnnnnnnnn nnnnnnnnnn nnnnnnnnnn 5700
nnnnnnnnnn nnnnnnnnnn nnnnnnnnnn nnnnnnnnnn nnnnnnnnnn nnnnnnnnnn 5760
nnnnnnnnnn nnnnnnnnnn nnnnnnnnnn nnnnnnnnnn nnnnnnnnnn nnnnnnnnnn 5820
nnnnnnnnnn nnnnnnnnnn nnnnnnnnnn nnngcatgcn nnnnnnnnnn nnnnnnnnnn 5880
nnnnnnnnnn nnnnnnnnnn nnnnnnnnnn nnnnnnnnnn nnnnnnnnnn nnnnnnnnnn 5940
nnnnnnnnnn nnnnnnnnnn nnnnnnnnnn nnnnnnnnnn nnnnnnnnnn nnnnnnnnnn 6000
nnnnnnnnnn nnnnnnnnnn nnnnnnnnnn nnnnnnnnnn nnnnnnnnnn nnnnnnnnnn 6060
nnnnnnnnnn nnnnnnnnnn nnnnnnnnnn nnnnnnnnnn nnnnnnnnnn nnnnnnnnnn 6120
nnnnnnnnnn nnnnnnnnnn nnnnnnnnnn nnnnnnnnnn nnnnnnnnnn nnnnnnnnnn 6180
nnnnnnnnnn nnnnnnnnnn nnnnnnnnnn nnnnnnnnnn nnnnnnnnnn nnnnnnnnnn 6240
nnnnnnnnnn nnnnnnnnnn nnnnnnnnnn nnnnnnnnnn nnnnnnnnnn nnnnnnnnnn 6300
nnnnnnnnnn nnnnnnnnnn ccatggnnnn nnnnnnnnnn nnnnnnnnnn nnnnnnnnnn 6360
nnnnnnnnnn nnnnnnnnnn nnnnnnnnnn nnnnnnnnnn nnnnnnnnnn nnnnnnnnnn 6420
nnnnnnnnnn nnnnnnnnnn nnnnnnnnnn nnnnnnnnnn nnnnnnnnnn nnnnnnnnnn 6480
nnnnnnnnnn nnnnnnnnnn nnnnnnnnnn nnnnnnnnnn nnnnnnnnnn nnnnnnnnnn 6540
nnnnnnnnnn nnnnnnnnnn nnnnnnnnnn nnnnnnnnnn nnnnnnnnnn nnnnnnnnnn 6600
nnnnnnnnnn nnnnnnnnnn nnnnnnnnnn nnnnnnnnnn nnnnnnnnnn nnnnnnnnnn 6660
nnnnnnnnnn nnnnnnnnnn nnnnnnnnnn nnnnnnnnnn nnnnnnnnnn nnnnnnnnnn 6720
nnnnnnnnnn nnnnnnnnnn nnnnnnnnnn nnnnnnnnnn nnnnnnnnnn nnnnnnnnnn 6780
```

FIG. 9(3)

```
nnnnnnnnnn nnnnnnnnnn nnnnnnnnnn nnnnnnnnnn nnnnnnnnnn nnnnnnnnnn 6840
nnnnnnnnnn nnnnnnnnnn nnnnnnnnnn nnnnnnnnnn nnnnnnnnnn nnnnnnnnnn 6900
nnnnnnnnnn nnnnnnnnnn nnnnnnnnnn nnnnnnnnnn nnnnnnnnnn nnnnnnnnnn 6960
nnnnnnnnnn nnnnnnnnnn nnnnnnnnnn nnnnnnnnnn nnnnnnnnnn nnnnnnnnnn 7020
nnnnnnnnnn nnnnnnnnnn nnnnnnnnnn nnnnnnnnnn nnnnnnnnnn nnnnnnnnnn 7080
nnnnnnnnnn nnnnnnnnnn nnnnnnnnnn nnnnnnnnnn nnnnnnnnnn nnnnnnnnnn 7140
nnnnnnnnnn nnnnnnnnnn nnnnnnnnnn nnnnnnnnnn nnnnnnnnnn nnnnnnnnnn 7200
nnnnnnnnnn nnnnnnnnnn nnnnnnnnnn nnnnnnnnnn nnnnnnnnnn nnnnnnnnnn 7260
nnnnnnnnnn nnnnnnnnnn nnnnnnnnnn nnnnnnnnnn nnnnnnnnnn nnnnnnnnnn 7320
nnnnnnnnnn nnnnnnnnnn nnnnnnnnnn nnnnnnnnnn nnnnnnnnnn nnnnnnnnnn 7380
nnnnnnnnnn nnnnnnnnnn nnnnnnnnnn nnnnnnnnnn nnnnnnnnnn nnnnnnnnnn 7440
nnnnnnnnnn nnnnnnnnnn nnnnnnnnnn nnnnnnnnnn nnnnnnnnnn nnnnnnnnnn 7500
nnnnnnnnnn nnnnnnnnnn nnnnnnnnnn nnnnnnnnnn nnnnnnnnnn nnnnnnnnnn 7560
nnnnnnnnnn nnnnnnnnnn nnnnnnnnnn nnnnnnnnnn nnnnnnnnnn nnnnnnnnnn 7620
nnnnnnnnnn nnnnnnnnnn nnnnnnnnnn nnnnnnnnnn nnaactagga atatttcaga 7680
cagatgccta actgctaagg ctcagagaaa cagcaaatta agtggatatc ctttatggat 7740
gactgtgatt ttcttttcct ataatggaag ccaagtaaat aagatgctat tatcccacta 7800
aaagcagcgg ttctcaacct ctgggtctcc accccttgag gtcaaatgac acttttaccg 7860
agggtcatct aagacattgg aaaacacaga tatttacatt atgactcaca accgtagaaa 7920
aattacactt atgaagtagc aacgaactaa ttttatcctt gaggaatagg gggggtcacc 7980
acaacatgca gatctgtatt aaagggttgc agcattagga aggtttagaa ccactgccct 8040
aagagtaggc aagactgcag gtctctcatg ggacttgcct gtttgcctag tgtctcagcc 8100
tgcctctctt cttccctgca cagaggtcta gggtgacagg acatgtgaca gccagccgag 8160
tgaagcagca gggttggctt cccttgccct tcacatctgt ttcagcctgg gatgcaggga 8220
gcagttgcat gatgtcccgt gttttcactt cacagaagat ctgtgtgagc ttccaggagc 8280
ttcccggggc tttcaatatc tgattctggc agctgacaga cagctgtgtc ttccacagcc 8340
ctccgtgtag aaatcggaat tcagagagct tttatcatgc tgaacagccg ggaccaggga 8400
aacctgcact ccggtttatg tctgtggcta tgtggattcc tggctctctt taaaggtgag 8460
ttattacggc ttatatccta gaatacaatt ggtagtgtgc atttcctctt ctttctcatc 8520
ttgtctggat ccaaataatt agaggacttt aattagttag cttaaccta acagatatga 8580
tttggaaagt aaggtagaga aaacattgaa gtacagtata atattcatac ttcatctctc 8640
caactaaaat atgcttttcc aattagcata caaaatcatc tgcttttgta gccatgtatg 8700
ctaccaatat gcttcattta cttacggtaa tttgttagct gggacttatt agcctgcgag 8760
tcctaccaat gtgtgtaatt gtcctcactt aggaaacctg tcttattgtc tactaagagt 8820
gagctttcct gtcttaaaag ttggctcaga cctggctggt gcacacacac acacacacac 8880
acacacacac acacacacac acgaacag gcacacatgc acacatctcg gatgaggttt 8940
cagggggtgc tgatggtgag ctccagagag aggaaacagt agcaacagcc aagagagctc 9000
actatcttct gaaacaatgt tttcatcctg gttagttaca caggnnnnnn nnnnnnnnnn 9060
```

FIG. 9(4)

nnnnnnnnnn nnnnnnnnnn nnnnnnnnnn nnnnnnnnnn nnnnnnnnnn nnnnnnnnnn 9120
nnnnnnnnnn nnnnnnnnnn nnnnnnnnnn nnnnnatgca tnnnnnnnnn nnnnnnnnnn 9180
nnnnnnnnnn nnnnnnnnnn nnnnnnnnnn nnnnnnnnnn nnnnnnnnnn nnnnnnnnnn 9240
nnnnnnnnnn nnnnnnnnnn nnnnnnnnnn nnnnnnnnnn nnnnnnnnnn nnnnnnnnnn 9300
nnnnnnnnnn nnnnnnnnnn nnnnnnnnnn nnnnnnnnnn nnnnnnnnnn nnnnnnnnnn 10020
nnnnnnnnnn nnnnnnnnnn nnnnnnnnnn nnnnnnnnnn nnnnnnnnnn nnnnnnnnnn 10080
nnnnnnnnnn nnnnnnnnnn nnnnnnnnnn nnnnnnnnnn nnnnnnnnnn nnnnnnnnnn 10140
nnnnnnnnnn nnnnnnnnnn nnnnnnnnnn nnnnnnnnnn nnnnnnnnnn nnnnnnnnnn 10200
nnnnnngcag tacaggctgt gaatctgaag agcagctctt ccacaggctg tttgctcact 10260
acaaccgctt catccggccg gtggagaatg tctccgatcc cgtcacggtg catcttgaat 10320
tggcaatcac gcaactggcc aatgtgnnnn nnnnnnnnnn nnnnnnnnnn nnnnnnnnnn 10380
nnnnnnnnnn nnnnnnnnnn nnnnnnnnnn nnnnnnnnnn nnnnnnnnnn nnnnnnnnnn 10440
nnnnnnnnnn nnnnnnnnnn nnnnnnnnnn nnnnnnnnnn nnnnnnnnnn nnnnnnnnnn 10500
nnnnnnnnnn nnnnnnnnnn nnnnnnnnnn nnnnnnnnnn nnnnnnnnnn nnnnnnnnnn 10560
nnnnnnnnnn nnnnnnnnnn nnnnnnnnnn nnnnnnnnnn nnnnnntcta gannnnnnnn 10620
nnnnnnnnnn nnnnnnnnnn nnnnnnnnnn nnnnnnnnnn nnnnnnnnnn nnnnnnnnnn 10680
nnnnnnnnnn nnnnnnnnnn nnnnnnnnnn nnnnnnnnnn nnnnnnnnnn nnnnnnnnnn 10740
nnnnnnnnnn nnnnnnnnnn nnnnnnnnnn nnnnnnnnnn nnnnnnnnnn nnnnnnnnnn 10800
nnnnnnnnnn nnnnnnnnnn nnnnnnnnnn nnnnnnnnnn nnnnnnnnnn nnnnnnnact 10860
ccctgggctg agcatataca aaccatcaca ccatgtctgc cagttgattg cagcttttcc 10920
agaaactagt gcatttgaaa ccatgattca aaattgttca cctgggtgtc aactaatatt 10980
ttcccgataa agaggtctag gctaatggtt ccaacaacgt ggtgtggtac tgtgtgtctc 11040
tggcctcctc ctccattagg gctcactgag ctcagtgtcc attgaaatgg tctggagttg 11100
catgaagact atgattttc cagagtaggt cctgactcat gacatttct aacacctcca 11160
aggttgtgta ttccccatga atacacacca tatggagcct atccaaacca tggaagtgtc 11220
tcaagggagg caggcctgtt aagaatggta ctgataatta gtgtcaactc cctgaactca 11280
cccaggtttt gaagactatg acaggtttag gccagttacc tctaagacct cacggaagtg 11340
aggcagcaga gcctatccag ctttgaccaa cagctagtac atacttaccc agcatctgtt 11400
agaccctaca gattcaaggc gactcaatac cagagggccc taatcaatag aggggaatca 11460
ctgggaagct gtgcaggctc catttccta agtctttttg ttgactttac caatcccagg 11520
gcctgtgttg gctccacatg acccactggc agggagaagc tnnnnnnnnn nnnnnnnnnn 11580
nnnnnnnnnn nnnnnnnnnn nnnnnnnnnn nnnnnnnnnn nnnnnnnnnn nnnnnnnnnn 11640
nnnnnnnnnn nnnnnnnnnn nnnnnnnnnn nnncctgcgt agaaacctca accaggctgg 11700
gatccttca ctcacagggac ctcagatgtc ttggaaaatg aaatttgaa tcccctgctg 11760
actgctaag aacctactatt aatacccaag ctattctgct gtgacctgtc acctgtcctg 11820
actctcctt atgtcacttca gggactgctt ggacagtaac tcttcaaaga agcctccttg 11880
actcgtata ttaaatagatg tgtgcataca cgcaggaatc actccacctc tcttgttata 11940
tcatgatgt gttttatgctg gcgtacacat ttattattag ctctgtcttt ccaaccacaa 12000

FIG. 9(5)

```
cagctaaga gcacatgaagg caggagcttt cttcactctg taacttgagt ggaactctgt 12060
aacacagtg gtcactgggta agtaggaata tcccttgtga ctgaagggcc cgtgagctgg 12120
gaaagggaa tacagagggag tgagtacctg gtttcaactg gcaaacttgc atgtgaacta 12180
aactgctgt ttcagtttgga tcccagggca aatgcacaca gtacatccca ggcttctttg 12240
aggaaaggc catggggatag ataaaaacag tgagtacctg tcgccaccta caggactctc 12300
ccctctgtc gtccctgaacc tctgccctcc tccctgttac ctttcatgca tctaggaagc 12360
tttatgggc caaggtggtga gaaaagattc acagaggagg tgaaatccaa atgatcttg 12420
atcaatatt ttaagtcacat gtcatttcta agtcaacaga gcagaggcaa ctggaaacgt 12480
tcgggattt ctgttacagtt aaatagcttt catgcagtct ccagtcttca tgtctgactt 12540
cattagcac ggataacttag atttgtctat ttttagatat aattctctag ttaagacttg 12600
tattagcaa gcacatagaag actgaaaaat attatttctt ccttccagga tgaagtcaac 12660
cagattatg gagaccaatct gtggctgcgt cacgtatgtg tccccccctt tgaatggcgg 12720
cagaatgta tccacttagtg ataaagccac ctgcattaac tttttcgcac cccaacctat 12780
gatagataa agaatatcctt ttccttgctt tctcctagtc cttgggtcag ctctggttgc 12840
agttatatt aatataggcag cacatgggca gagcctggtg tctgacatgg aaccctctgg 12900
cctttctct tttaagctccc agttctcttt gtatcactta ctgataccaa gnnnnnnnnn 12960
nnnnnnnnnn nnnnnnnnnn nnnnnnnnnn nnnnnnnnnn nnnnnnnnnn nnnnnnnnnn 13020
nnnnnnnnnn nnnnnnnnnn nnnnnnnnnn nnnnnnnnnn nnnnnnnnnn nnnnnnnnnn 13080
nnnnnnnnnn nnnnnnnnnn nnnnnnnnnn nnnnnnnnnn nnnnnnnnnn nnnnnnnnnn 13140
nnnnnnnnnn nnnnnnnnnn nnnnnnnnnn nnnnnnnnnn nnnnnnnnnn nnnnnnnnnn 13200
nnnnnnnnnn nnnnnnnnnn nnnnnnnnnn nnnnnnnnnn nnnnnnnnnn nnnnnnnnnn 13260
nnnnnnnnnn nnnnnnnnnn nnnnnnnnnn nnnnnnnnnn nnnnnnnnnn nnnnnnnnnn 13320
nnnnnnnnnn nnnnnnnnnn nnnnnnnnnn nnnnnnnnnn nnnnnnnnnn nnnnnnnnnn 13380
nnnnnnnnnn nnnnnnnnnn nnnnnnnnnn nnnnnnnnnn nnnnnnnnnn nnnnnnnnnn 13440
nnnnnnnnnn nnnnnnnnnn nnnnnnnnnn natctggaag gactacagat tgcgttggga 13500
tccaacggag tatgatggca tcgagacact tcgagttcca gcagacaaca tctggaagcc 13560
tgacatcgtt ctgtataacn nnnnnnnnnn gcatnnnnnn nnnnnnnnnn nnnnnnnnnn 13620
nnnnnnnnnn nnnnnnnnnn nnnnnnnnnn nnnnnnnnnn nnnnnnnnnn nnnnnnnnnn 13680
nnnnnnnnnn nnnnnnnnnn nnnnnnnnnn nnnnnnnnnn nnnnnnnnnn nnnnnnnnnn 13740
nnnnnnnnnn nnnnnnnnnn nnnnnnnnnn nnnnnnnnnn nnnnnnnnnn nnnnnnnnnn 13800
nnnnnnnnnn nnnnnnnnnn nnnnnnnnnn nnnnnnnnnn nnnnnnnnnn nnnnnnnnnn 13860
nnnnnnnnnn nnnnnnnnnn nnnnnnnnnn nnnnnnnnnn nnnnnnnnnn nnnnnnnnnn 13920
nnnnnnnnnn nnnnnnnnnn nnnnnnnnnn nnnnnnnnnn nnnnnnnnnn nnnnnnnnnn 13980
nnnnnnnnnn nnnnnnnnnn nnnnnnnnnn nnnnnnnnnn nnnnnnnnnn nnnnnnnnnn 14040
nnnnnnnnnn nnnnnnnnnn nnnnnnnnnn nnnnnnnnnn nnnnnnnnnn nnnnnnnnnn 14100
nnnnnnnnnn nnnnnnnnnn nnnnnnnnnn nnnnnnnnnn nnnnnnnnnn nnnnnnnnnn 14160
nnnnnnnnnn nnnnnnnnnn nnnnnnnnnn nnnnnnnnnn nnnnnnnnnn nnnnnnnnnn 14220
nnnnnnnnnn nnnnnnggat ccnnnnnnnn nnnnnnnnnn nnnnnnnnnn nnnnnnnnnn 14280
nnnnnnnnnn nnnnnnnnnn nnnnnnnnnn nnnnnnnnnn nnnnnnnnnn nnnnnnnnnn 14340
```

FIG. 9(6)

```
nnnnnnnnnn nnnnnnnnnn nnnnnnnnnn nnnnnnnnnn nnnnnnnnnn nnnnnnnnnn 14400
nnnnnnnnnn nnnnnnnnnn nnnnnnnnnn nnnnnnnnnn nnnnnnnnnn nnnnnnnnnn 14460
nnnnnnnnnn nnnnnnnnnn nnnnnnnnnn nnnnnnnnnn nnnnnnnnnn nnnnnnnnnn 14520
nnnnnnnnnn nnnnnnnnnn nnnnnnnnnn nnnnnnnnnn nnnnnnnnnn nnnnnnnnnn 14580
nnnnnnnnnn nnnnnnnnnn nnnnnnnnnn nnnnnnnnnn nnnnnnnnnn nnnnnnnnnn 14640
nnaatgctgt cggcgacttc caggtcgaag gcaagaccaa agctcttctc aagtatgacg 14700
gtgtgataac ctggacccca ccagccatct ttaagagctc ctgcccaatg acatcacct 14760
tcttcccgtt tgaccatcaa aactgctccc tgaagtttgg ttcctggact tatgacaagg 14820
cagaaatcga ccttctcatc attggctcta agtagacat gaacgactt tggaaaaca 14880
gtgaatggga aattgtcgac gcctctggct ataagcatga catcaagtac aactgctgtg 14940
aagagattta cacggacata acctactcct tctacatcag gaggttgccc atgttttaca 15000
ccatcaacct catcatcccc tgcctcttca tttccttcct cacggtgctg gttttttacc 15060
ttccctccga ctgtggcgag aaagtgactc tttgcatctc cgttctgctt tctctcactg 15120
tcttttgct ggtgattaca gagaccatcc catccacatc tctcgtgatc ccactggtgg 15180
gtgagtatct actgttcacc atgatctttg tcacgctgtc cattgtggtg accgtgttcg 15240
tgctgaacat acactacagg accccagcaa cgcataccat gcccaagtgg gtgaagacca 15300
tcttccttca ggccttcccc tcgattctga tgatgaggaa acctctggac aagacaaagg 15360
aggcaggagg tgttaaggac cccaaaagcc ataccaagag gcctgccaag gtcaaattta 15420
ctcatcgagg agaatccaaa cttctaaagg aatgccacca ctgccaaaaa tcaagtgaca 15480
tagcacctgg aaagagaaga tcaagccagc agcctgcacg gtgggtggca gagaattcag 15540
agcactcgtc cgatgttgaa gatgtcatcg agagtgttca attcatagca gaaaacatga 15600
agagccacaa tgaaacaaac gaggtaaaag tggagccctt ttctccagcc agctgcaccc 15660
ctagcaggcc tacaggcact ttagagacta gtcagagcgt cagtgggagt tacatatgtg 15720
gaacagtcag ggaccgtcac ctaagaccag ctctattatc atgaagcctt gtgggacctg 15780
ggttcaagtt tagggagcta tagtgagagg atatatgtag tcctacaaca aatcttcagc 15840
ctgcatttac ttacggtgag gtctagccac agtgcacatg caggacaagc cttcctcaag 15900
gaacaagcct ccaatgcatc gaacactgac aaagtgaggg tgggaaggga gactgtagaa 15960
atcattatta ataaaatccc accggcgggc ttgctacctg ctctaatggt ttgtgttccc 16020
aaatgaaaca cacacacaca cacacacaca cacacacaca cacacacagt ctttgtgttt 16080
taatatgccg tatacagcac aatagctggg ccactgccta ccctccatgc tgttactata 16140
cctcccgcca acaatcccca agttattact tactaattct atgtgctatc ttggttgccc 16200
ctagacccag ttgggcagcc tctgggccat gttttccccg gctatttcaa gtggtggcca 16260
tgtctctctg tcctgcagtc ttctcaggcc tagcatctca cctcttcctc cacactctcc 16320
cggcatggca gggtctcact tctcctcctc ctcctcctcc tcctccacca cctcctttct 16380
cctccctccc tcctccctcc cctctttccc ctcccccctt ccttcccagc ctgagaactc 16440
ctaaaatccc acctctccct gtccttttcca gctttggctg ttggcagctt tatttaccaa 16500
taagaaccaa ctgcgggcag gttcccagaa actacaggca gacagtccca cgaaaacagt 16560
tttacgtgga ccataattag cattcataat acgtgcagct acagagacac ccaaggaaaa 16620
gaagaactgt ggtactgcct gaagccccag tggtgaaaga tgccccttag cagtcagcag 16680
```

FIG. 9(7)

```
ctcccatcac acttcctcta ctagaggggg acccagacat gagttaaaga catcttgaag    16740
atgtgctcag tatgcacacg tattccgtgc ctgtgtccca cactctaatg cctagagctt    16800
ggctcctcct accccaagca agtgctcaag gatagggaga tcaccacttg actgaggttt    16860
cccgccaggt gtctggagat gcttcatact atagctccta acatctgtaa ctcataggga    16920
aagaatatca gaaccaccac cacccccaa aaaacacact gagagacact gagaatgcct    16980
gtcataacat gtcacaggag agcaatggcc agtgagctca cctcctggct ggcatctttt    17040
agaatgtacg gcaatacgtt acgttgattt atcannnnnn nnnnnnnnnn nnnnnnnnnn    17100
nnnnnnnnnn nnnnnnnnnn nnnnnnnnnn nnnnnnnnnn nnnnnnnnnn nnnnnnnnnn    17160
nnnnnnnnnn nnnnnnnnnn nnnnnnnnnn nnnnnnnnnn nnnnnnnnnn nnnnnnnnnn    17220
nnnnnnnnnn nnnnnnnnct ctcacttgct tcacactcag attccccca aacagccagg    17280
cacacgtgac aagagcttga ctctcaagca gatatattgt gtagagcgaa gaaaggaccc    17340
ttatcacagg caaagggtca caaaagtctt tgatacagtt catagcccag tgatgtacat    17400
ctgctctccc ttagaccatg agtcctacat aggacatgca ggcagtcagg caggcaaaca    17460
taatagcaat aattgggttt tttgaaagga ttggagaaaa tgctttggag aaaaaaaaaa    17520
gtattcataa aacatagcat gttttcttat agtcttggtt tttaaagcta gccttgatcc    17580
tttgtttgca tttcaggtag aagacgactg gaaatacatg gctatggtgg tggacagagt    17640
cttcctttgg gtatttataa ttgtctgtgt gtttggaact gtggggctat ttctgcagcc    17700
actgcttggg aacacaggaa actcttaatt ggtattgtcc ctccgagctc atcaagct      17758
```

FIG. 9(8)

MOUSE MUTANT FOR EXPRESSION OF THE ALPHA6 SUBUNIT OF THE NICOTINIC ACETYLCHOLINE RECEPTOR

CROSS REFERENCE TO RELATED APPLICATIONS

This application is a continuation of International Application No. PCT/FR01/02741, filed Sep. 4, 2001, and claims priority of French Application No. 0011247, filed Sep. 4, 2000, the content of which is incorporated herein by reference.

The present application relates to non-human mammals mutant for expression of the alpha6 subunit of the nicotinic acetylcholine receptor, hereinafter abbreviated to "nAChR", and to the use of said mammals for identifying or screening for molecules that can interact with said receptor.

Little is currently known about the role of nicotinic acetylcholine receptors in the central nervous system. Such receptors (Marubio, L. M., et al. Reduced antinociception in mice lacking neuronal nicotinic receptor subunits. Nature, 1999. 398: p. 805-810) are involved in nociception, memory, locomotion control, nicotine dependence, and certain neurodegenerative disorders such as Parkinson's disease or Alzheimer's disease (Newhouse, P., et al. Nicotinic system involvement in Alzheimer's and Parkinson's diseases. Implications for therapeutics. Drugs Aging, 1997. 11 (3): p 206-228), but the mechanisms of that involvement have not been identified.

Regarding nicotine dependence, recent work has shown the importance of the beta2 subunit of nAChR as regards nicotine dependence properties in rodents (Picciotto, M. et al. Acetylcholine receptors containing beta2-subunit are involved in the reinforcing properties of nicotine. Nature, 1998 391: p. 173-177). In that prior work, mice lacking the beta2 subunit were incapable of maintaining auto-administration behaviour when cocaine was replaced by nicotine. That study also underlined the absence of an electrophysiological response of the mesencephalic dopaminergic neurons of mutant mice in response to nicotine. Furthermore, microdialysis experiments carried out on mutant mice showed that the release of dopamine was affected in the nucleus accumbens (corresponding to the ventral portion of the striatum) after systemic administration of nicotine. Those observations contributed to highlighting the parallel that may exist between nicotine and other addictive drugs, such as heroin or cocaine,. in which the dependence effects are linked to an increase in the basal level of dopamine in the nucleus accumbens.

However, the extended cellular expression profile of the beta2 subunit did not allow an accurate definition of the regions of the brain contributing to initiation of nicotine dependence, and the nature of the alpha subunits associated with the beta2 subunit in that process were not identified.

Of the eight alpha subunits of nAChR already identified in the brain of rodents, certain, in particular the alpha4 subunit, have been used to examine their properties.

In the present application, the inventors have chosen to concentrate on a particular subunit, the alpha6 subunit of neuronal nicotinic acetylcholine receptors, this subunit possibly being associated with the beta2 subunit and having an expression profile restricted to catecholaminergic neurons (Le Novere, N. et al. Neuronal nicotinic receptor alpha6 subunit mRNA is selectively concentrated in catecholaminergic nuclei of the rat brain, European Journal of Neuroscience, 1996, 8(11): p. 2428-39). In a highly advantageous manner in the present application, the inventors have selected this subunit for its expression profile that is principally localized to the substantia nigra, the ventral tegmental area and the locus coeruleus.

Studies (Le Novere, N. et al. Involvement of alpha6 nicotinic receptor subunit in nicotine-elicited locomotion, demonstrated by in vivo antisense oligonucleotides infusion. NeuroReport, 1999. 10: p. 2497-2501) have shown that antisense oligonucleotides can demonstrate the importance of the alpha6 subunit in the hyperlocomotive effect of nicotine in the usual environment, an effect which would be mediated by the mesencephalic dopaminergic system. Those elements have led certain authors to hypothesize that the alpha6 subunit could play a role in regulating the release of dopamine by nicotinic agonists (Reuben M. B. S. et al. Nicotinic receptors modulating somatodendritic and terminal dopamine release differ pharmacologically. Eur. J. Pharmacol, 2000, 393(1-3): p. 39-49). However, those authors have observed that the result obtained on the potential and efficacy of the test agonist associated with dopamine release does not resemble that which was obtained with recombinant nictonic cholinoreceptors containing the alpha6 subunit.

The invention provides means that allow in vivo observation or observation in an in vitro system that can approach the existing in vivo conditions, to identify or screen for molecules that can interact in a ligand/receptor type reaction with nicotinic acetylcholine receptors and in particular with those comprising the alpha6 subunit of said receptors.

Thus, the invention concerns non-human mammals, in particular rodents and more particularly mice, which are mutant for the gene coding for the nAChR alpha6 subunit, said mammals being depleted in functional alpha6 subunit. In the remainder of the description, these animals will be termed "knockout" to qualify the mutation that they have in the gene coding for the alpha6 subunit of nAChR receptors. These mammals can constitute animal models for identifying substances, in particular substances having pharmacological properties, which interact with said alpha6 subunit in the nAChR receptors. These receptors comprising the alpha6 subunit can be of type 2α6, 2β2, β3 (Le Novere N. et al. European Journal of Neuroscience, 1996, 8(11), p 2428-39).

In particular, by dint of these animals or products, in particular cell cultures which can be derived therefrom, the invention provides a model that allows to determine the selectivity of substances of interest towards nAChR receptors present in certain neuronal populations and, in particular in the catecholaminergic neurons.

Given substances can be tested on animals expressing the nAChR alpha6 subunit normally and the same test can be carried out on animals in accordance with the invention that are mutant for this subunit expressed in the functional form, to allow the respective effects observed to be compared, in particular any interaction of the test substance with nicotinic transmission and dopaminergic transmission mediated by the alpha6 subunit of nAChR receptors.

The means of the invention are particularly suitable to screening and in particular to pharmacological screening of substances that may behave as ligands for the nAChR receptors, via their interaction with the nicotine binding site of the alpha6 subunit, and in particular capable of a nicotinic type agonist or antagonist activity. Particularly advantageously, the identified substances bind to nAChRs via the alpha6 subunit and have a restricted specificity for dopaminergic neurons. This specificity can be detected because of expression of the nAChR alpha6 subunit, restricted to those dopaminergic neurons.

As an example, it has been observed that Parkinson's disease is characterized by a selective degeneration of dopaminergic neurons of the substantia nigra.

The capacity of the identified substances to behave as ligands for the nAChR alpha6 subunit defines, within the context of the invention, substances having an activity comparable to that of acetylcholine, or to that of agonists such as nicotine, at least as regards the capacity of acetylcholine or nicotine to bind to nAChR receptors comprising the alpha6 subunit. Examples of substances having such properties are nicotine, cytisine, epibatidin, and their derivatives obtained by chemical modification.

Examples of antagonist substances binding to said nAChR alpha6 subunit are DhβE, hexamethotium, alpha-bungarotoxin and n-bungarotoxin. Examples are mentioned in the publication by Spang J. et al. (Chem Biol, 2000 7(7): p 545-555) and Sharples C. et al. (J Neurosci, 2000, 20(8): p 2783-91).

Available results on the neuroprotective effect of nicotine in Parkinson's disease (Newhouse P. et al. Drugs Aging, 1997, 11(3): p 206-228) open the doors to new possibilities for different therapies with nicotinic agents. The design of nicotinic substances, which may have therapeutic properties and may be used in the design of a drug, which may have a selectivity for receptors containing the alpha6 subunit, could be of advantage in particular as regards avoiding undesirable side effects such as the cardiovascular risks associated with exposure to nicotine.

Thus, the invention provides a non-human mammal carrying a mutation in the gene coding for the alpha6 subunit of the nicotinic acetylcholine receptor (nAChR), said mutation preventing expression in the mammal of said nAChR alpha6 subunit in a functional form.

The expression "functional form" as used in the context of the invention means the form of the alpha6 subunit (α6) of nAChR which allows recognition and interaction between this subunit and agonists or antagonists of receptors in which it is present, and more particularly which allows binding to acetylcholine. The functional form of the alpha6 subunit is thus that in which said subunit comprises a functional binding site for agonist or antagonist molecules.

The functional nature of the binding site can be verified by the fact that acetylcholine, present or administered under conditions allowing its interaction with nAChr receptors comprising the alpha6 subunit, modifies the amount of dopamine release compared with the amount of dopamine which can be released when the alpha6 subunit is absent or non-functional. In other words, the absence of the alpha6 subunit or its presence in a non functional form alters the amplitude and the pharmacology of the response of nAChR receptors to nicotine. The examples describe the tests that can be used in this regard.

The remainder of the text will also refer to the "functional form" of the gene to translate the capacity of the gene to express an alpha6 subunit in the functional form. The non-human mammals of the invention are thus those which have undergone genetical inactivation of the gene coding for the alpha6 subunit of nAChR.

In a first implementation of the invention, the non-human mammal is characterized in that the gene coding for the nAChR alpha6 subunit is mutated by deletion of all or a portion of its exons.

A binding site for the nAChR alpha6 subunit recognized by nicotine and by other agonists and antagonists of this receptor is coded by exons 2, 3 and 4 of the gene coding for said alpha6 subunit.

Further, deletion of exons 1 and 2 by their destruction prevents correct translation of mRNA (because ATG and splicing sites are destroyed) even in the gene transcription hypothesis. In fact, the absence of exons 1 and 2 prevents gene transcription.

Thus, the invention particularly pertains to a non-human mammal, characterized in that the gene coding for the nAChR alpha6 subunit is mutated by deletion of at least a portion of exon 1 and/or at least a portion of exon 2, which, in the nAChR alpha6 subunit expressed in the mammal, is sufficient to prevent binding of said nAChR alpha6 subunit with its agonists and/or antagonists.

Preferably, the non-human mammal of the invention is mutated by essentially complete deletion of exons 1 and 2.

In particular, the invention pertains to a non-human mammal, in particular a rodent and especially a mouse, characterized in that the mutation of the gene coding for the nAChR alpha6 subunit is homozygous in nature.

The mutation is, for example, such that the mammal has phenotype ($\alpha6^{-/-}$) and no longer expresses the nAChR alpha6 subunit, the two alleles of the gene being mutated in similar manner.

In a further implementation, the invention concerns a non-human mammal characterized in that the mutation for the gene coding for the nAChR alpha6 subunit is homozygous, said mammal having a ($\alpha6^{\Delta1-2/\Delta1-2}$) phenotype.

Phenotype ($\alpha6^{\Delta1-2/\Delta1-2}$) corresponds to expression of a gene coding for the alpha6 subunit, said gene being truncated at exons 1 and 2, so that said subunit is effectively expressed and in particular comprises the transmembrane portion of the native alpha6 subunit; the expressed receptor is not functional for binding agonists which is normally dependent on correct transcription and translation of exons 1 and 2.

Figure 1B:
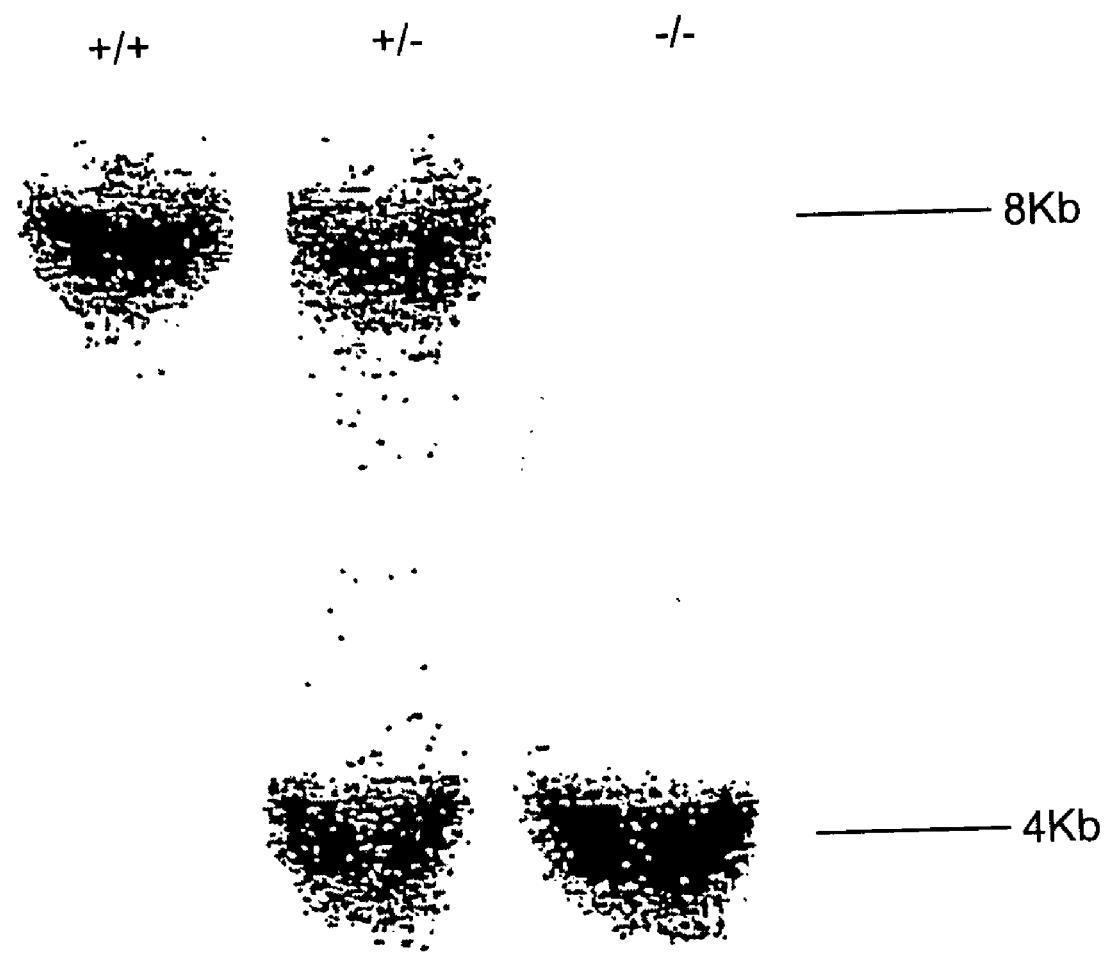

Said non-human mammals can be obtained by the known technique of the skilled, of homologous recombination of the wild type gene coding for the nAChR alpha6 subunit, with a construct of the type of the target construct of FIG. 1. The homozygous nature of the mutation can result from crossing two animals with one mutated gene allele, the homozygous descendants then being selected. Alternatively, the homozygous nature of the mutation can be obtained directly from ES cells by increasing the concentration of neomycin used for selection and retaining only those clones that have undergone homologous double recombination.

The non-human mammals of the invention can be obtained so that non functional expression of the nAChR alpha6 subunit or the absence of expression of this alpha6 subunit is constitutive, the animal being mutated for the functional gene or incapable of expressing its transcription product.

Alternatively, the invention concerns non-human mammals, characterized in that the mutation of the gene coding for the nAChR alpha6 subunit is of the inducible or conditional type.

The inducible or conditional nature of the mutation can be useful in particular because the animal which is mutated by induction for expression of the gene for the nAChR alpha6 subunit in the functional form is not in a position to undergo behavioral adaptations, for example by compensation, and thus of modifying its behaviour towards agonists or antagonists, and in general towards any substance that can interact normally with the native nAChR alpha6 subunit.

Mammals in accordance with the invention in which the mutation in question is inducible can be obtained by specific recombination techniques allowing recombination intended to establish deletion or mutation of a gene to be carried out under the control of certain agents, in particular tetracycline or RU486 (Kellendonk C. et al. J. Mol. Biol. 1999, 285(1): p 175-82), for example in certain neuronal cell populations.

Inducible gene inactivation lies in using an inducible promoter (for example the TRE/rtta system (Gossen M. et al. Science, 1995, 268: p 1766-9)) which controls expression of an enzyme, Cre-recombinase. In that system, transgenic animals are generated that express both the synthetic activator rtta under the control of a specific promoter in certain tissues, and Cre-recombinase under the control of the inducible promoter TRE. In the presence of tetracycline, the rtta activator binds to the TRE promoter and induces expression of Cre-recombinase only in the cells in which rtta is expressed. In parallel, homologous recombination produces animals in which the gene coding for the alpha6 subunit is flanked by two LoxP sites. These sites are the target for Cre-recombinase which causes excision of the entire DNA fragment located between two LoxP sites. By crossing these animals, descendants are obtained in which excision of the alpha6 gene can be induced simply by adding tetracycline to the drinking water.

The LoxP sites in question can alternatively be inserted into the gene to frame a fragment of the gene, deletion of which is sufficient to inactivate the gene or lead to expression of a non-functional alpha6 subunit.

Other equivalent systems can be used.

The non-human mammals of the invention, in particular rodents and especially mice, can be obtained by crossing animals carrying the genetic constructions necessary for producing the desired mutation of the gene coding for the nAChR alpha6 subunit and in a manner so as to render said mutation homozygous. The invention also concerns animals descended from said animals.

The invention also concerns knockout non-human mammals in which the gene for the nAChR alpha6 subunit is heterozygously mutated. Because of this heterozygous mutation, said animals have, a reduced sensitivity to ligands for the alpha6 subunit and are thus of interest in confirming that an observed reduction in an agonist or antagonist effect towards the alpha6 subunit with a substance can be attributed to the mutation.

Different constructs have been produced to render preparation of the animals of the invention possible. These constructs are described in detail in the following examples and in particular, the invention concerns a non-human mammal and in particular a mouse, characterized in that its gene coding for the nAChR alpha6 subunit is mutated by homologous recombination with the sequence designated a6KO contained in the *E. coli* strain deposited at the CNCM with accession number 1-2550 on Aug. 29, 2000.

The invention also concerns cell populations and in particular cell cultures as obtained from a non-human mammal as described above.

Within the context of the invention, these cell populations are neuronal populations and in particular cell populations that normally express the alpha6 subunit of nAChR receptor, such as catecholaminergic neurons. Examples of advantageous cell populations are mesencephalic neuronal cells.

The invention also concerns preparations of striatal synaptosomes.

The invention also concerns the use of a non-human mammal, a synaptosome preparation or a cell culture as defined as above for the study of the effects of given substances on nicotinic receptors.

One particularly advantageous use of the invention in this context is for the study of the effects of addictive drugs on the nicotinic receptors of acetylcholine, said drugs possibly already being known and identified as such in general or being known without their properties having been identified, or being novel as regards their structure and functions.

In particular, the use of animals of the invention or synaptosome preparations or derived cell cultures allows, for example by measuring the amount of dopamine release, the effect of agonists for the nicotinic acetylcholine receptors (nAChR) in particular the alpha6 subunit of these receptors, to be determined.

Particularly advantageously, the animals, synaptosome preparations, or cell cultures of the invention can be used in screening protocols, in particular pharmacological protocols, for nAChR agonist or antagonist substances.

The specificity of a test substance towards a nAChR receptor can be characterized by observation, for a substance, of a high activity (i.e., an activity of the order of that obtained with nicotine, or higher) on a mouse or other wild type mammal and the absence of activity on a mouse or other mammal in accordance with the invention.

More specifically, the knockout animals of the invention or the cell cultures or the synaptosome preparations allow identification, from agonists or antagonists for the nicotinic acetylcholine receptors, of those which can have a restricted effect to catecholaminergic neurons, in particular restricted to dopaminergic neurons.

The test substances are known substances, for example known for their agonist or antagonist properties as regards receptors and in particular as regards nAChR receptors. They can also be novel substances which the invention can be used to identify certain properties thereof, in particular certain pharmacological characteristics as regards the nAChR receptors.

The invention concerns a method for screening substances that are capable of interacting with the nAChR alpha6 subunit, comprising:
  bringing the selected substance into contact with a non-human mammal of the invention, under conditions that allow interaction between said substance and the nicotinic acetylcholine receptors;
  detecting the ligand/receptor type interaction.

Thus, the invention provides a method for screening substances that can interact with the nAChR alpha6 subunit, selected from substances interacting with nAChR receptors, comprising:
  bringing the selected substance into contact with a non-human mammal of the invention, under conditions that allow interaction between said substance and the nicotinic acetylcholine receptors;
  detecting the amount of dopamine released in the striatum.

The invention also concerns a method for screening substances that can interact with the nAChR alpha6 subunit, selected from substances interacting with nAChR receptors, comprising:
  bringing the selected substance into contact with a cell culture in accordance with the invention, under conditions that allow interaction between said substance and the nicotinic acetylcholine receptors;
  detecting the amount of dopamine released.

The invention also concerns a method for screening substances that can interact with the nAChR alpha6 subunit, selected from substances interacting with nAChR receptors, comprising:
  bringing the selected substance into contact with a synaptosome preparation in accordance with the invention, under conditions that allow interaction between said substance and the nicotinic acetylcholine receptors;
  detecting the amount of dopamine released.

Examples of other methods for detecting the interaction of the screened substances with the nAChR alpha6 subunit are those which employ a double hybrid system such as those described in International patent application WO-99/42612.

The variation in the detected dopamine level can be evaluated by comparison of the basal level of dopamine released in an animal expressing the nAChR alpha6 subunit normally, or released in a synaptosome preparation carried out from such an animal, or in a cell culture expressing this subunit, with the level of dopamine released when the animal, preparation or culture in question is brought into contact with the test substance under conditions that allow its interaction with the alpha6 subunit.

In a further mode of the invention, the screening methods employ substances the capacity of which to bind to nAChRs has not previously been studied.

In a further implementation, the cell cultures of the invention are used to study or identify, from agonist or antagonist substances for the nicotinic acetylcholine receptors, those which have a neuroprotective effect.

Thus, the invention provides a method for screening substances that can interact with the nAChR alpha6 subunit, selected from substances interacting with nAChRs, comprising:
    bringing the selected substance into contact with a cell culture in accordance with the invention, under conditions that allow interaction between said substance and the nicotinic acetylcholine receptors;
    apply a stress to said cell culture;
    observing the neuroprotective effect of said substance on said culture as regards said stress.

Stressing a cell culture has been described, for example in the publication by Akaike A et al., (Brain Res 1994, 644(2): p 181-7). The effect of said stress may be cell death. In this case, observation of the neuroprotective effect may consist of comparing the cell death caused by this stress on a culture expressing the alpha6 subunit with that caused by said stress on the cell culture of the invention, said cell cultures having previously been brought into contact with the screened substance.

The method of the invention as defined, which can be implemented for the uses described above in accordance with the invention, allows substances having an affinity for the alpha6 subunit to be identified, and which interact with nicotinic transmission and dopaminergic transmission in a manner that is selective by binding to receptors comprising the alpha6 subunit via said subunit. This method is of particular advantage when studying the interaction of addictive drugs with the alpha6 subunit of nAChR and in particular when studying their selectivity towards identified neuronal populations.

The possible variation in the amount of dopamine released in the striatum of an animal of the invention can be detected using known techniques, in particular the techniques described in the examples below.

As an example, after implementing the method of the invention, the variation, in particular increase, will be detected in the level of dopamine released compared with the base dopamine level detected in an animal expressing the nAChR alpha6 subunit normally.

When the mutation in the alpha6 subunit is conditional or inducible, the desired basal level of released dopamine can be detected prior to inducing the mutation and subsequently compared with the dopamine level in the same animal in which the mutation has been induced.

In that case, the level of released dopamine is measured by microdialysis (Marshall D. et al. J. Neurochem, 1997, 68(4): p 1511-9) In a preferred implementation of the method of the invention, the test substances are substances for which the selective affinity for nicotinic acetylcholine receptors restricted to dopaminergic neurons is to be determined.

In a preferred implementation of the method of the invention, the test substances are substances having an affinity for nAChR receptors comprising an alpha6 subunit for which the selectivity towards this subunit is sought, the method comprising:
    a) bringing the selected substance into contact with a non-human mammal as hereinbefore defined, under conditions that allow interaction between said substance and the nicotinic acetylcholine receptors;
    b) detecting the dopamine released in the striatum;
    c) comparing the amount of dopamine released in the striatum in step b) with the amount of dopamine released detected in the striatum of the non-human mammal expressing the nAChR alpha6 subunit.

In a further implementation, this method comprises:
    a) bringing the selected substance into contact with a synaptosome preparation as defined in the invention, under conditions that allow interaction between said substance and the nicotinic acetylcholine receptors;
    b) detecting the amount of dopamine released;
    c) comparing the amount of dopamine released detected in step b) with the amount of dopamine released in a synaptosome preparation from a non-human mammal expressing the nAChR alpha6 subunit.

In a further implementation, this method comprises:
    a) bringing the selected substance into contact with a cell culture as defined in the invention, under conditions that allow interaction between said substance and the nicotinic acetylcholine receptors;
    b) detecting the amount of dopamine released;
    c) comparing the amount of dopamine released detected in step b) with the amount of dopamine released in a cell culture expressing the nAChR alpha6 subunit.

Steps b) and c) of said methods can be replaced by any step allowing detection of the ligand/receptor interaction.

In a particular implementation of the screening methods of the invention, the non-human mammals, synaptosome preparations or cell cultures are controls for the interaction of the selected substances with the alpha6 subunit of nAChR receptors and these methods comprise a step in which the effect of the test substance on the alpha6 subunit is determined on an animal that is wild type for expression of said alpha6 subunit or on a preparation of synaptosomes of such an animal or on a cell culture expressing said subunit normally.

The invention also concerns the substances identified at the end of a screening method in accordance with the invention, and their use in the preparation of compositions, in particular for therapeutic purposes.

The invention also concerns vectors, and in particular plasmids comprising all or a portion of a gene coding for the alpha6 subunit of nAChR receptors, in particular vectors carrying a mutated gene for the alpha6 subunit, said vectors possibly constituting means for preparing constructions intended to produce the animals of the invention.

To this end, particularly advantageous plasmids are those selected from the following plasmids deposited at the CNCM (Collection National de Culture de Microorganismes, Paris, France):
    a6HN: CNCM N° 1-2500 deposited on Jun. 22, 2000;
    a6EH: CNCM N° 1-2501 deposited on Jun. 22, 2000;
    a6EE: CNCM N° 1-2502 deposited on Jun. 22, 2000;
    a6PP: CNCM N° 1-2503 deposited on Jun. 22, 2000;
    a6KO: CNCM N° 1-2550 deposited on Aug. 29, 2000;

or the bacterial artificial chromosome (BAC) designated a6BAC deposited at the CNCM with accession number I-2504 on Jun. 22, 2000.

The invention also concerns a sequence of nucleotides contained in one of the plasmids identified above or in the bacterial artificial chromosome also identified above.

A preferred sequence of nucleotides in accordance with the invention is characterized in that it comprises all or a portion of the concatenations shown in FIGS. 2, 3, 4, 5 or 6 and in particular the sequenced concatenations shown in these figures.

The invention also concerns fragments of said sequences and in particular the exons identified in the gene coding for the nAChR alpha6 subunit.

Further, the invention concerns recombinant cells comprising a nucleotide sequence as identified above or a vector containing it. Particularly advantageous recombinant cells are neuronal cells and in particular dopaminergic neurons or cells derived from the mesencephalic region of the brain of animals in accordance with the invention.

Other characteristics and properties of the invention will become apparent from the following examples.

KEY TO FIGURES

FIG. 1. Screening of the gene for the nAChR alpha6 subunit.
  a) Genomic structure of the gene for the alpha6 subunit, including exons 1 to 6, and the structure of the transfer vector. Restriction sites: E, EcoRI; H, HindIII; S, SlaI; P, PstI; N, NotI. The NotI site shown in parentheses is in the phage used to construct the vector; it is absent from the wild type allele. The 5 kb EcoRI-EcoRI and 4.6 kb HindIII-NotI fragments used to construct the homologous arms are shown above the wild type allele (WT). The recombination vector was used to produce replacement mutation; and it contains a neomycin resistance gene (Neo$^r$) as a positive selection marker and a diphtheria toxin gene (DTA) as a negative selection marker. After homologous recombination, a 4 kb deletion including exons 1 and 2 had been formed. The DNA fragments, digested with PstI, detected by the SalI-SpeI probe, are shown by the dotted lines.
  b) Southern blot analysis identifying homozygous knockout (−/−), heterozygous (+/−) and wild type (+/+) alpha6 type animals.

Figure 2:
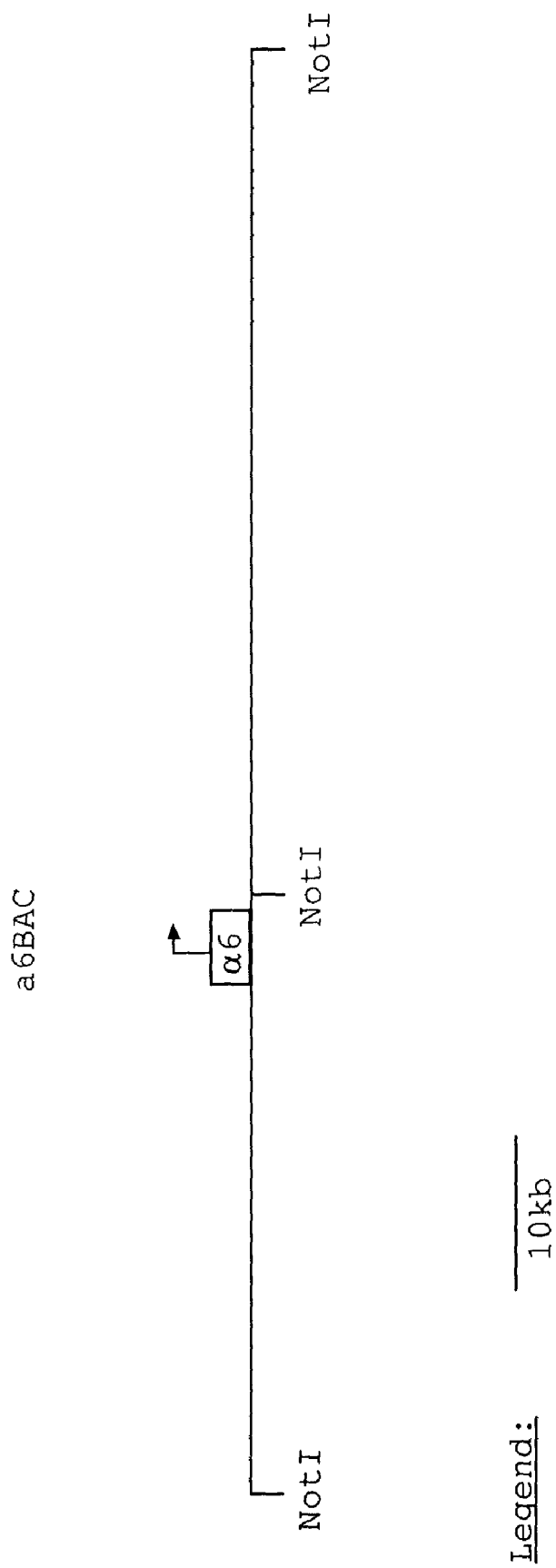

FIG. 2:
A: Restriction map of the bacterial artificial chromosome designated a6BAC (CNCM I-2504, deposited Jun. 22, 2000). The bac contains about 130 kb of insert deriving from a mouse line 129sv DNA library. This insert (α6) corresponds to the locus of the nicotinic acetylcholine receptor (nAChR) alpha6 subunit from exon I to exon VI.
B: Sequence for 13 kb insert, oriented in the direction of transcription.

FIG. 3:
A: Restriction map for plasmid a6HN (CNCM I-2500, deposited on 22 Jun. 2000).
Plasmid a6HN is constituted by a KS-Bluescript vector and a 4.6 kb insert cloned into the HindIII, NotI sites, deriving from the gene for the alpha6 subunit of the mouse nicotinic acetylcholine receptor (DNA deriving from ES cells from the SV/D3 strain). This fragment contains exons 3 to 5 of the alpha6 subunit. (Direction of transcription: HindIII to NotI).

B: Sequence for 4.6 kb insert. Exons 3, 4 and 5 are in capital letters. "n" represents non sequenced bases.

Figure 4A:
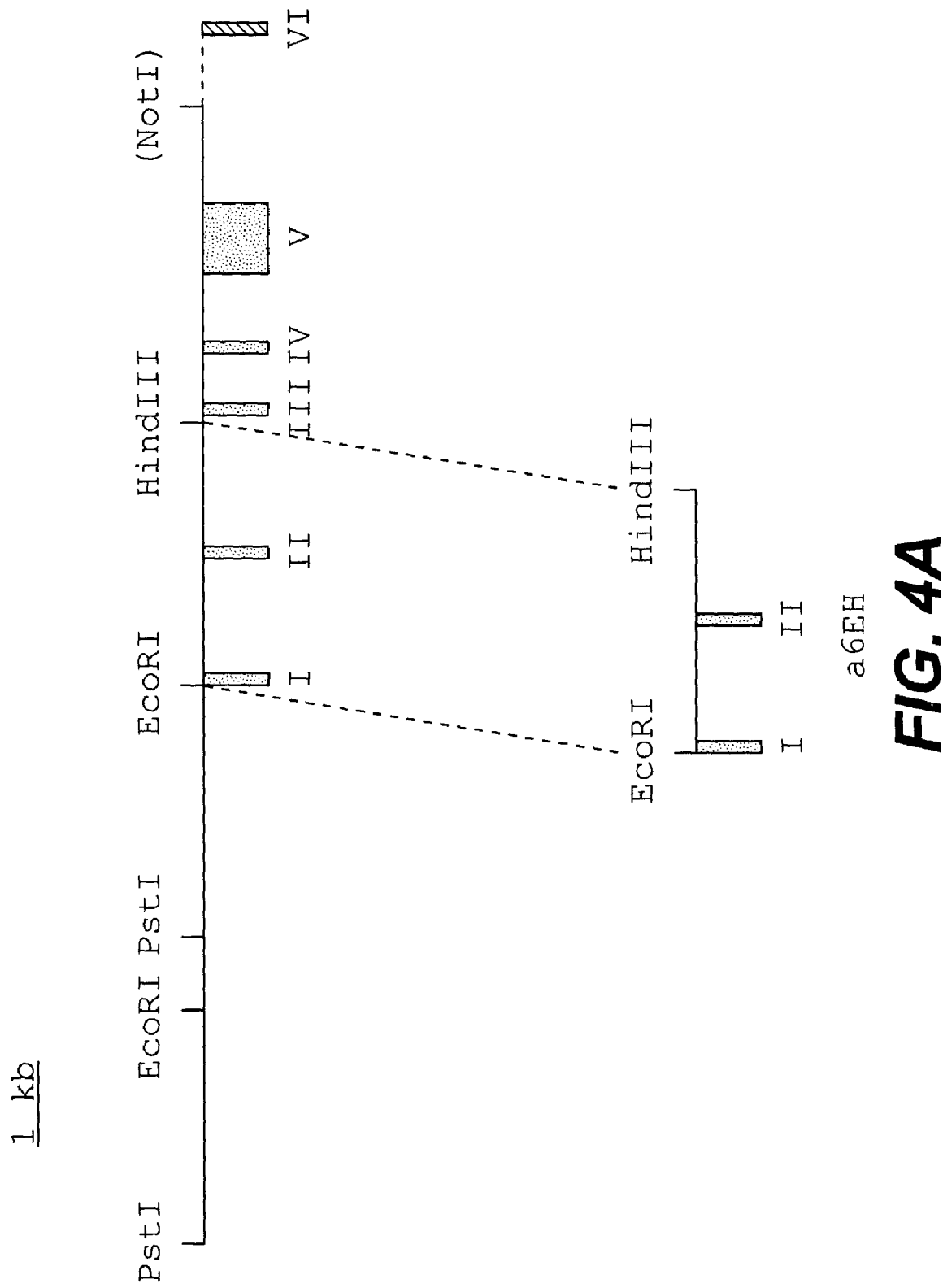

FIG. 4:
A: Restriction map for a6EH plasmid (CNCM I-2501, deposited on Jun. 22, 2000).
The a6EH plasmid is constituted by a vector, SK, and a 4 kb insert, cloned into the EcoRI-HindIII sites. This inert is an EcoRI-HindIII fragment of the gene for the alpha6 subunit of the mouse nicotinic acetylcholine receptor (DNA deriving from ES cells from the 129 SV/D3 strain). It contains the first two exons of the alpha6 subunit (Direction of transcription: EcoRI to HindIII).
B: Sequence for 4 kb insert. Exons 1 and 2 are in capital letters. "n" represents non sequenced bases.

Figure 5A:
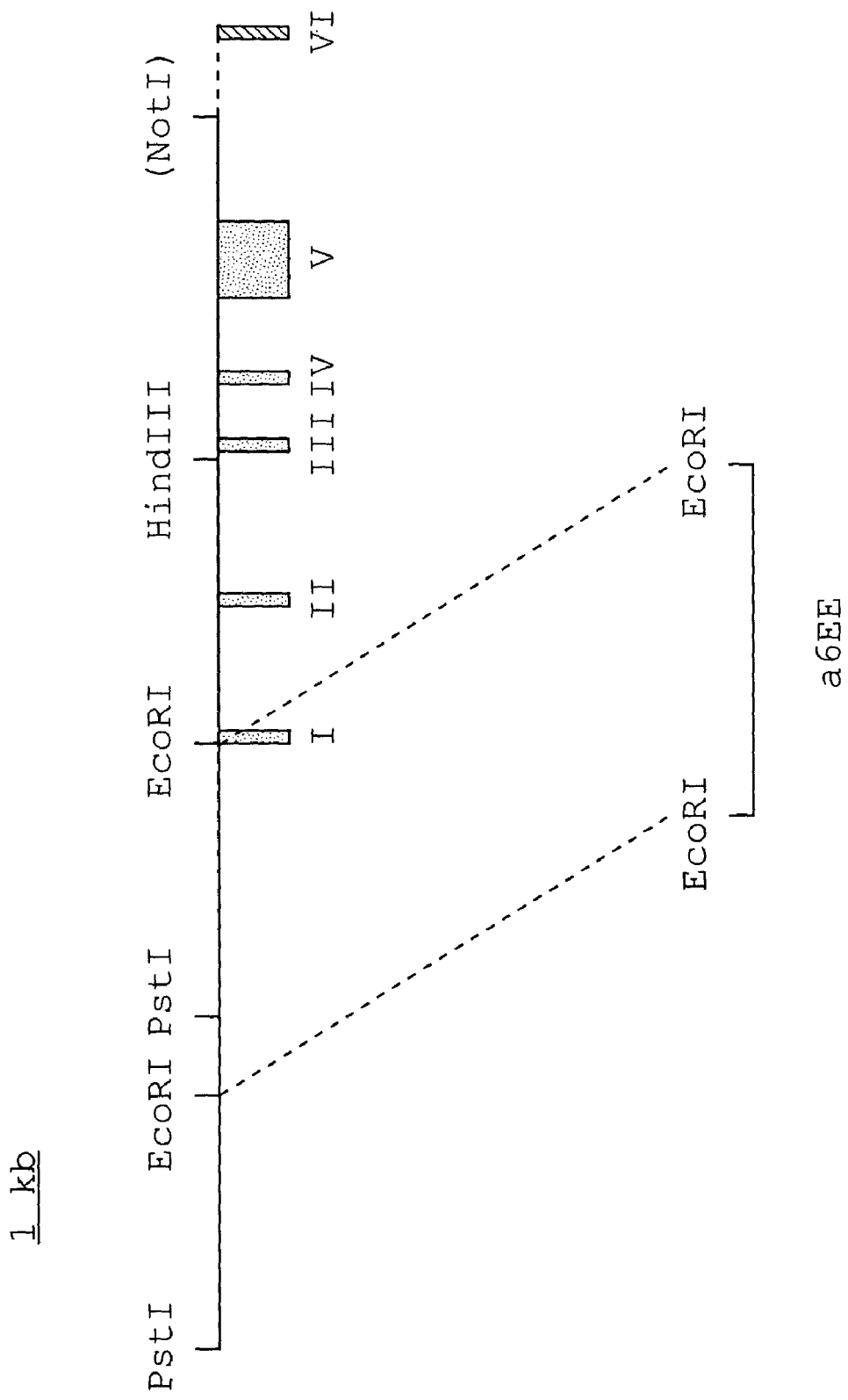

FIG. 5:
A: Restriction map for plasmid a6EE (CNCM 1-2502, deposited on Jun. 22, 2000).
Plasmid a6EE is constituted by a SK-Bluescript vector and a 5 kb insert cloned into the EcoRI site. This insert is an EcoRI-EcoRI fragment of the alpha6 subunit of the mouse nicotinic acetylcholine receptor (DNA deriving from ES cells from the 129 SV/D3 strain). It contains 5 kb of non-coding sequence immediately upstream of the ATG of alpha6. These 5 kb of promoter are oriented in the SacI-KpnI direction of the SK.
B: Sequence for 5 kb fragment of promoter for the nAChR alpha6 subunit. The restriction sites are in capital letters. The sequence (EcoRI-EcoRI) is oriented from 5' to 3' in the direction of transcription. "n" represents non sequenced bases.

Figure 6A:
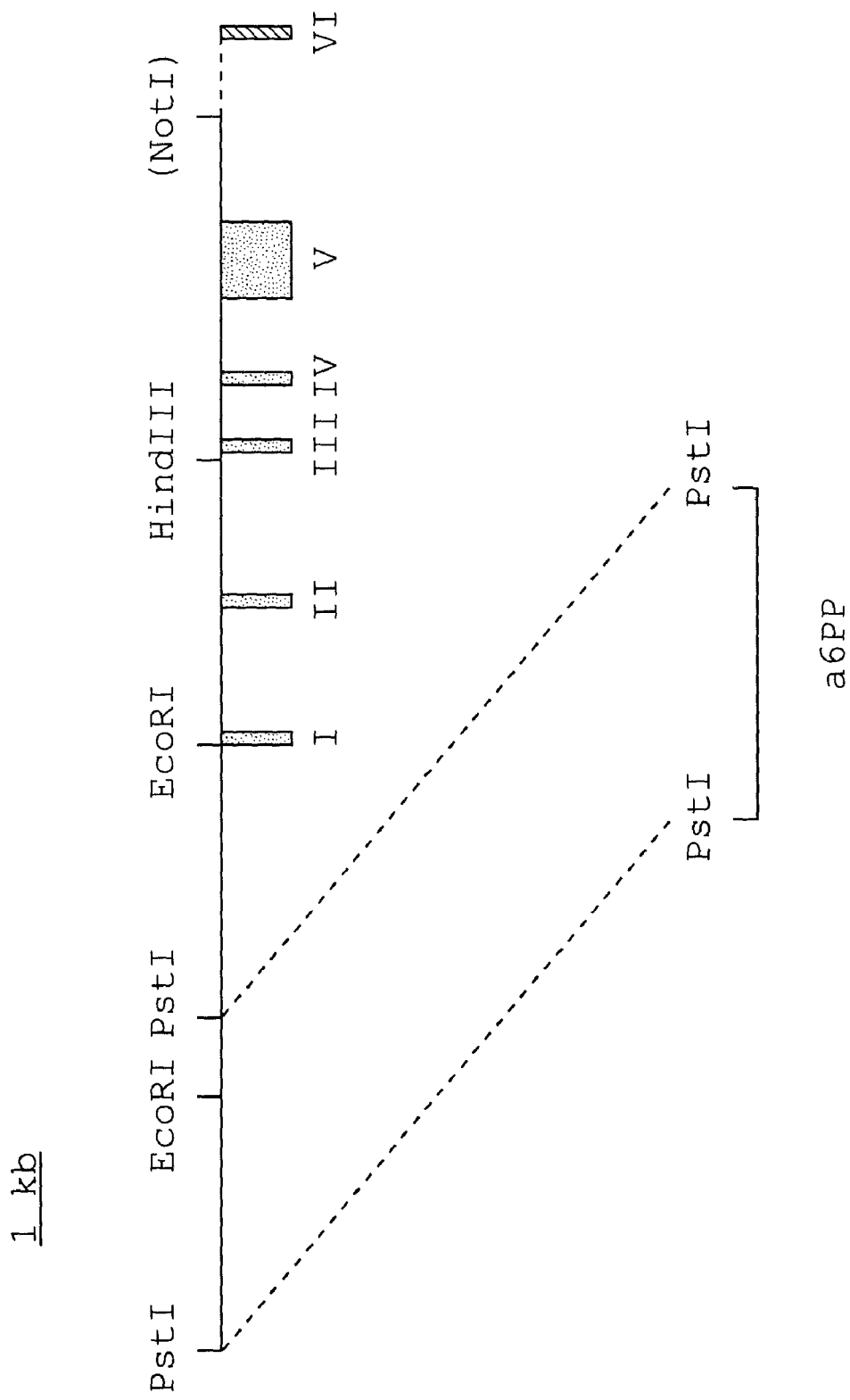

FIG. 6:
A: Restriction map for plasmid a6PP (CNCM I-2503, deposited on Jun. 22, 2000).
Plasmid a6PP is constituted by inserting a 4.5 kb PstI-PstI fragment for the alpha6 subunit of the mouse nicotinic acetylcholine receptor (DNA deriving from ES cells from the 129 SV/D3 strain) into the PstI site of the SK-Bluescript vector. This 4.5 kb sequence belongs to the a6 promoter region. The 3' end of this fragment is 3.9 kb in the 5' direction from the ATG of the α6 gene.
B: Sequence for 4.5 kb insert, oriented in the direction of transcription. "n" represents non sequenced bases.

Figure 7:
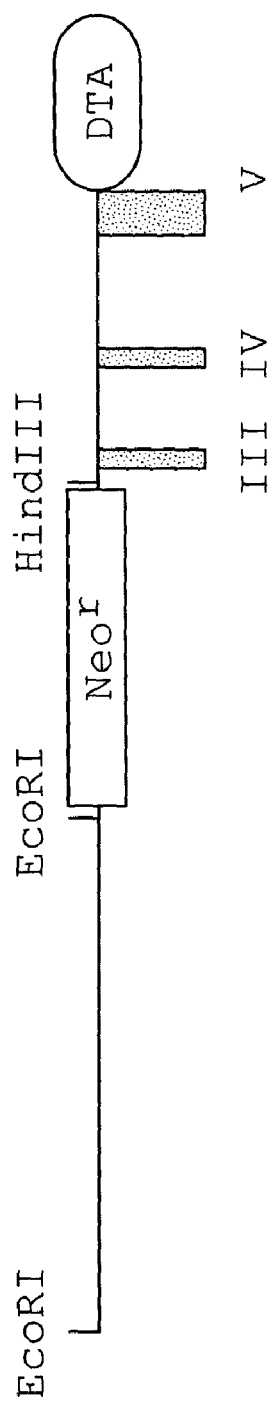

FIG. 7:
A: Restriction map for plasmid a6KO (CNCM I-2550, deposited on Aug. 29, 2000) contained in *E. coli* bacteria from the DH5α strain. The plasmid is used for homologous recombination into the locus of the alpha6 subunit of the mouse nicotinic receptor. This plasmid is constituted by a SK-Bluescript vector and a 12 kb insert. This insert contains two homologous arms belonging to the mouse alpha6 gene sequence (4 kb and 5 kb) flanking a neomycin resistance cassette (3.3 kb) (Neo$^r$). A diphtheria toxin expression cassette (DTA) is also included (1.4 kb).

Figure 8:
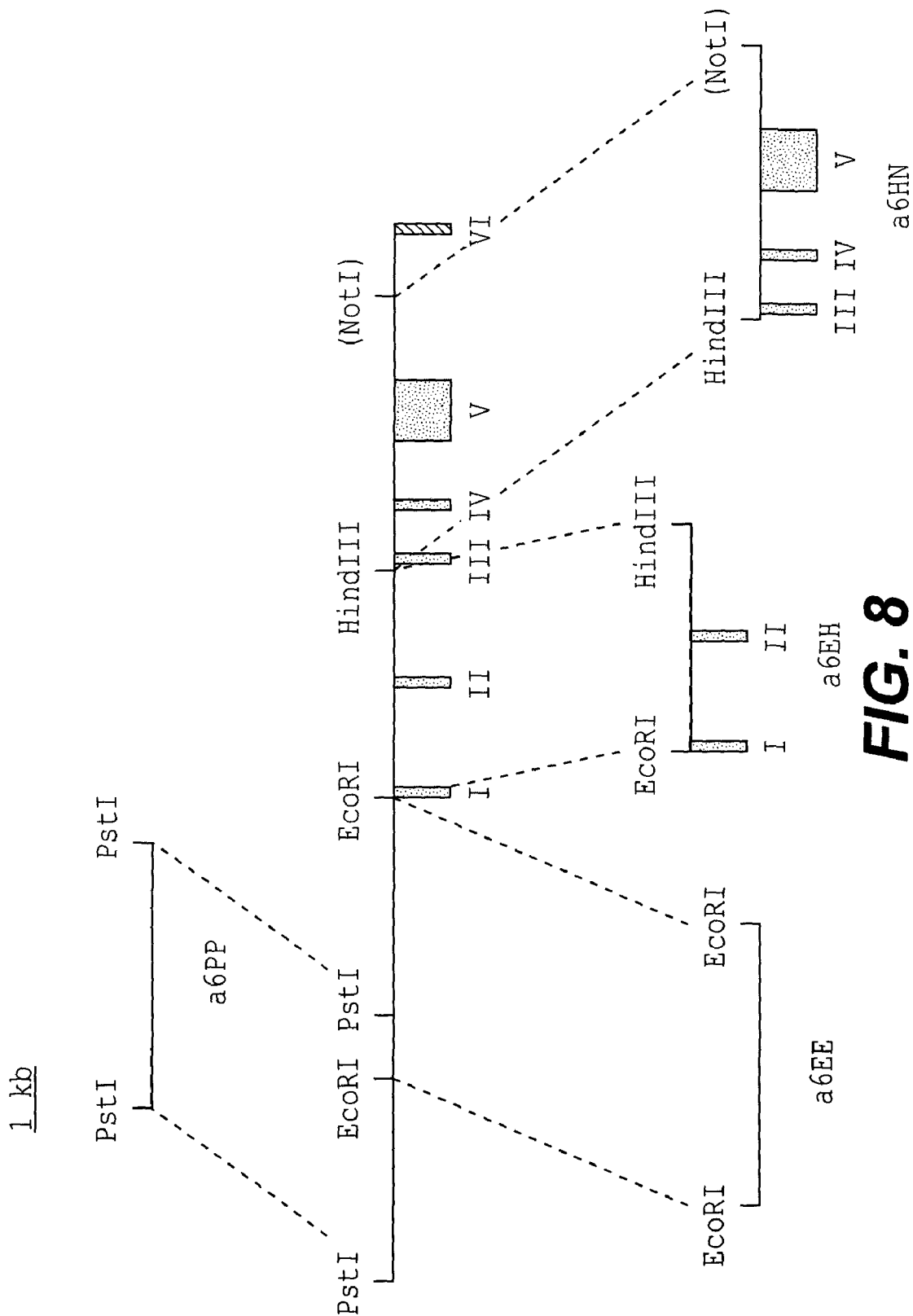

FIG. 8: Localisation of the different restriction fragments a6PP, a6EE, a6EH, a6HN.

FIG. 9: Sequence of alpha6 locus of the nAChR receptor alpha6 subunit. The exons are in capital letters.

FIG. 10: In situ hybridization using an oligonucleotide probe located in exon 6 of the a6 subunit. Note the expression in the substantia nigra and the ventral tegmental area (SN/VTA) and in the locus coeruleus (LC). In knockout animals, the signal disappears completely.

FIG. 11: Quantification of autoradiographs obtained from in situ hybridization against subunits α3, α4, α5, α7, β2 and β4 of the nicotinic receptor. Cx=cortex; Th=thalamus; MHb=medial habenula; IPN=interpeduncular nucleus; Hp=hippocampus.

FIG. 12: Labelling of retinogenicular projections using fluorescent cholera toxin. Coronal sections representing left (a, c) and right (b, d) geniculate nuclei of Wt (a, b) and a6−/− (c, d) animals. Both eyes were injected with choleric toxin coupled with 2 different fluorophores (red for left eye, green for right eye). Note the absence of superimposition of labels, characteristic of normal segregation (scale: 350 µm).

FIG. 13: Autoradiograph of binding of αCtxMII to brain sections from Wt and mutant animals. Note the presence of binding sites in 3 major anatomic systems: the visual system (dorsolateral geniculate nucleus (dlGN), ventrolateral geniculate nucleus (VLGN), superior colliculus (SC), olivary pretectal nucleus (OPN), optic tract (opt)), the mesolimbic dopaminergic system (substantia nigra (SN), ventral tegmental area (VTA), nucleus accumbens (Nacc), striatum (Str)) and the interpeduncular habenulo system (interpeduncular nucleus (IPN) and medial habenula (MHb)).

FIG. 14: Displacement of binding of epibatidin by αCtxMII on striatum membrane preparations.

FIG. 15: Release of dopamine induced by application of 3 µM nicotine to striatal synaptosomes in the absence (a) or presence (b) of 100 nM of αCtxMII. Dose-response curve for dopamine release in response to nicotine in α6−/− (c) or α4−/− (d) animals. The maximum response was normalized to 1. Note the loss of affinity of an order of magnitude in the α4−/− animals.

EXAMPLES

Materials and Methods

Preparation of "knockout" mice (mice mutated for the gene coding for the nAChR alpha6 subunit, expression in the functional form of the alpha6 subunit of nAChR receptor being altered).

The majority of protocols used to prepare the knockout mice are described in Laboratory protocols for conditional gene targeting . . . , Torres R. and Kühn R. Oxford University Press (1997).

1.1. Construction of Recombination Vector

A strategy based on PCR (Israel, D. A PCR based method for high stringency screening of DNA libraries. Nucleic Acids Res., 1993, 21(11): p 2627-31) was used to screen a mouse genomic DNA library prepared from embryonic stem cells (ES cells) from the 129 SV/D3 line. Other commercially available mice (Janvier, Charles River) could be used. However, it is preferable to use the same line from which the ES cells used for homologous recombination are derived. Oligonucleotides were selected from the cDNA sequence of the rat alpha6 subunit.

```
Forward primer:
5'ACTGCTGTGAAGAGATTTACACA3'

Reverse primer:
5'AAGATGGTCTTCACCCACTTG3'
```

This screening allowed a phage containing approximately 17 kb of the alpha6 subunit of the nicotine acetylcholine receptor (α6 nAChR) to be isolated.

Restriction mapping and partial sequencing enabled the position of the first five exons to be determined. The sixth exon was outside the cloned sequence (see FIG. 1). A recombination vector of the replacement type was then constructed to introduce a 4 kb deletion into the locus for the alpha6 subunit to remove exons 1 and 2. To prepare the recombination vector, the 4.6 kb HindIII-NotI fragment and the 5 kb EcoRI-EcoRI fragment were sub-cloned into KS-Bluescript plasmids to generate plasmids a6HN and a6EE (KS) respectively. To supply new restriction sites, the SpeI-XhoI fragment of the a6EE plasmid was then sub-cloned into a modified bluescript vector in which the polylinker had been replaced by SacI-SfiI-ApaI-SpeI-XhoI-XbaI-NotI to constitute the plasmid a6EE(NS). During this time, a Neo$^r$ expression cassette was introduced into the XhoI-HindIII sites of a6HN. The XhoI-NotI fragment of the resulting plasmid was then sub-cloned into the SalI-NotI sites of a6EE(NS). Finally, a diphtheria toxin expression cassette was introduced into the SalI (of exon 5 in the alpha6 subunit)-NotI site of this plasmid, reducing the homologous length of the right arm to 2.5 kb.

1.2. Transfection $10^7$ pluripotent embryonic stem cells (ES cells) derived from the 129sv/Pas mouse line (Kress et al., Non-permissiveness for mouse embryonic stem (ES) cell derivation circumvented by a single backcross to 129/Sv strain: establishment of ES cell lines bearing the Omd conditional lethal mutation, Mamm Genome, 1998, 9(12): p 998-1001) were electroporated with 20 µg of DNA of recombination vector linearized with ScaI using a Bio-Rad electroporation apparatus (250 V, 500 µF). After 8 days selection in a medium containing G418 antibiotic (Gibco-BRL) (400 µg/ml), 200 antibiotic-resistant colonies were removed and dissociated in trypsin for plating onto 96-well plates. After 2 days growth, each clone was dissociated in trypsin and plated onto two wells of a 48-well plate. The contents of one of the wells were used for freezing while the contents of the other were plated onto a 24 well plate to prepare the genomic DNA.

1.3. Screening of Recombinant ES Cell Clones by Genomic Southern a) Preparation of DNA Wells in confluence in the 96-well plate were washed with PBS and incubated at 37° C. for 12 hours with 500 µl of cellular lysis buffer (100 mM tris-HCl pH 8: 5 mM EDTA; 0.2% SDS; 200 mM NaCl, 100 µg/ml proteinase K). The genomic DNA was then recovered by precipitation from ethanol and re-suspended in 150 µl of water.

b) Digestion and Transfer

50 µl of this genomic DNA preparation was used for digestion with 50 units of PstI for 6 hours at 37° C. The digestion product was then charged onto 0.8% agarose gel and underwent TAE electrophoresis at 40 V for 20 hours. The digested DNA was transferred onto a nylon membrane (Hybon-N+, Amersham) by Southern transfer in a 20×SSC buffer. The DNA was fixed on the membrane by exposure to UV light for 5 minutes.

c) Labelling the Probe 25 ng of the 800 bp SalI-SpeI fragment of the alpha6 gene was labeled using a random priming kit from Amersham (RPN 1607). This label was localized at the 3' end with respect to the right homologous arm outside the screening construction.

d) Hybridization and Washing

Transferred membranes were pre-hybridized for 30 minutes in 40 ml of hybridization buffer (0.5 M $NaHPO_4$ (pH 7.6), 7% SDS, 0.1 mg/ml salmon sperm DNA) at 65° C. Hybridization was carried out in 10 ml of the same buffer containing $10^6$ cpm/ml of denatured probe (3 min at 100° C.) for 15-20 hours at 65° C. The membranes were then washed twice with 0.1SSC; 0.1% SDS and exposed in a Phosphorimager cassette (Molecular Dynamics) for 24 hours before revealing.

This probe (SalI-SpeI fragment) and this restriction enzyme (PstI) allowed two bands to be detected in the recombinant clones: an 8 kb band corresponding to the wild type allele and a 4 kb band corresponding to the mutated allele.

The three recombinant ES cell clones obtained were multiplied and kept frozen in small aliquots in liquid nitrogen before use in aggregation.

1.4. Preparation of Chimeras

Chimeras were obtained using a modification of the aggregation protocol as described by Khillan J. and Y. Bao, Preparation of animals with a high degree of chimerism by one-step co-culture of embryonic stem cells and preimplantation embryos. Biotechniques 1997, 22(3), p 544-9). Culturing overnight in a standard cell culture incubator produced small quantities of recombinant ES cells to be aggregated with wild type preimplantation embryos. The aggregates that developed in the form of blastocytes were then reimplanted in surrogate mothers in a state of pseudopregnancy to prepare the chimeric animals.

a) Preparation of ES Cells

Two days prior to aggregation, a cryotube containing $5 \times 10^6$ ES cells was used to seed a 50 mm dish containing culture medium. The following day, the cells were dissociated and deposited in different concentrations on a 6-well plate (more particularly, dilutions of 1/3, 1/6, 1/12 and 1/24 were deposited on the initial 50 mm plate to use in the three forthcoming aggregation days).

The day of aggregation, the ES cells underwent mild dissociation (4 min in trypsin) to generate small aggregates of ES cells (4-20). The trypsin was inhibited by adding serum-containing medium. After mild dissociation using a 10 ml pipette, the cells were spread on a gelatinized tissue culture plate and placed in an incubator for 20 minutes. This step allowed selective removal of nutritive fibroblasts and large aggregates of ES cells which sedimented more rapidly. The supernatant containing the ES cells was harvested and kept on ice while the embryos were prepared.

b) Embryo Preparation

Five days prior to aggregation, 3 week old female mice (CD1 or C57BI6) were superovulated by injecting 5 units of PMS followed 46 hours later by an injection of 5 units of HCG (Intervet) then mated with two-month old male mice from the corresponding line, i.e., CD1 or C57BI6. The day of aggregation (2.5 days pc), 9 superovulated mice were sacrificed to recover their embryos in the morula stage and which were preserved in M2 medium (Sigma).

The zona pellucida was then removed by incubation in Tyrode's solution (Sigma): this step was carried out at ambient temperature under a microscope. Once the zona pellucida had disappeared, the embryos were transferred into drops of M2 medium to limit their exposure to the Tyrode's solution.

c) Preparation of Aggregation Plates 6 drops (5 µl) of aggregation medium (50% M16+50% standard ES cell medium) were placed on an untreated 35 mm culture plate. These drops were then covered with mineral oil to prevent evaporation. Using the end of dissection tweezers, 6-8 small depressions (aggregation wells) were prepared in each drop.

Each well had received a small aggregates (clumps) of ES cells (4-8 cells for C57BI6 embryos and 8-12 cells for CD1 embryos) and a morula. Care was taken to maximize contact between the cells and the embryo to allow aggregation. The plate was then placed in an incubator overnight.

d) Reimplantation of Aggregates

The day after aggregation, 90% of the aggregates had developed into blastocytes. These blastocytes were then reimplanted into the uterus of female B6D2 mice (2.5 pc) in a pseudopregnant condition.

1.5. Preparation of Homozygous Knockout Mice

For each strain (C57BI6 or CD1), a germinal line transmitter was obtained and crossed with B6D2/F1 or CD1 mice (respectively) for selection by colour of the skin of the resulting newborns. Agouti-coloured newborns were then analysed by genomic Southern. The mutation had been transmitted to C57BI/6J mice by crossing for the subsequent experiments.

2) Release of Dopamine from Superfused Striatal Synaptosomes

2.1. Preparation of Synaptosomes

The striata from two mice were rapidly dissected onto ice (total moist weight=60 mg) and placed in 10 vol of 0.32 M sucrose/5 mM HEPES pH 7.5 cooled on ice. The striata were then homogenized in a glass/Teflon homogenizer (15 hits at 900 rpm). The homogenate was centrifuged at 1000 g for 5 minutes at 4° C. to remove the nuclei and cell debris. The supernatant was then centrifuged at 12000 g for 20 minutes at 4° C. The final residue, consisting of a crude synaptosomal preparation (P2), was resuspended in a superfusion buffer (6 mg of initial tissue weight/ml). The superfusion buffer (SB) was composed as follows: (mM): NaCl 128, KCl 2.4, $CaCl_2$ 3.2, $KH_2PO_4$ 1.2, $MgSO_4$ 0.6, HEPES (pH 7.5) 25, D-glucose 10, L-ascorbic acid 1 and pargyline 0.1.

2.2. Charging Synaptosomes with Tritiated Dopamine

The synaptosome preparation was incubated with [$^3$H] dopamine (100 nM) for 20 min at 37° C. then centrifuged at 12000 g for 5 minutes. The residue was resuspended in SB buffer and charged onto a 13 mm diameter A/E glass fibre filter (Gelman Sciences) in a light vacuum. (The striatal synaptosomes from 2 mice are generally sufficient for 12 filters).

2.3. Superfusion

The superfusion apparatus used was commercially available (Brandel). It consisted of 6-20 identical channels. Each channel was constituted by a retention chamber (vol=100 µl) containing filters carrying the synaptosomes. This chamber was connected, via a Tygon tube (internal diameter=1.14 mm) to a multichannel peristaltic pump (Masterflex) and to an effluent collection device. The superfusion buffer (SB) was pumped continuously through the chamber at a rate of 500 µl/min.

After a 15 minute flushing period, the effluent was collected every minute in scintillation flasks containing 5 ml of scintillant. After collecting for 5 minutes, the drug being studied was administered for 1 minute and the effluent collected over a new 10 minute period. Finally, the quantity of tritiated dopamine released in each sample was measured using a scintillation counter (Wallac 1214 Rackbeta).

2.4. Data Analysis

The basal level for dopamine release was estimated by adjusting the data from the first 5 samples collected prior to administration of the drug with an exponential decay curve (y=a.exp(-bt)). The release peak was then defined as the maximum of the ratio "100× (measured dopamine-base line)/base line" for the next 10 samples after administration of the drug. This calculation method avoided problems linked to differences in the total quantity of radioactivity present on each filter.

3) Molecular and Anatomical Characterization of Knockout Mice for the α6 Subunit (α6−/−).

3.1. Verification of Animals

A study of the expression of mRNA coding for alpha6 subunit of the nicotine acetylcholine receptor (nAChR) confirmed the results obtained in the rat and chicken (Le Novere et al. 1996, Eur J Neurosci 8, 2428-39; Vailati et al., 1999 Mol Pharmacol 56, 11-19). In wild type animals (Wt), α6 is expressed both in the ganglion cells of the retina and the catecholaminergic neurons (substantia nigra (SN), ventral tegmental area (VTA) and locus coeruleus (LC)). In α6−/− animals, however, we have shown the total disappearance of the mRNA of the α6 subunit, confirming the functionality of the deletion that was made.

The inventors have also verified the absence of developmental compensation associated with any over-expression of other nAChR subunits to make up for the disappearance of α6 in mutant animals. In situ hybridization using oligonucleotide probes directed against the subunits α3, α4, α5, α7, β2, and β4, of the nicotinic receptor have shown that such a mechanism did not exist in α6−/− animals, at least on a transcriptional level.

On a general point, α6−/− animals are viable, present in Mendelien proportions in the litters, mature normally and do not exhibit any major physical or neurological defect.

3.2 Absence of Anatomical Anomaly in the Nervous Systems of α6−/−

The inventors investigated the anatomical development of neuronal structures in which α6 is normally expressed.

a) The visual System

In the visual system, the inventors studied the ganglion cell projections of the retina in the dorso-lateral geniculate nucleus, since the anatomical organization of these projections is known to be regulated during development by the activity of nicotinic transmission in the retina. In contrast to that observed with β2−/− animals (Rossi et al., 2001 Proc. Natl. Acad. Sci. USA 98, 6453-6458), α6−/− mutants exhibited no alteration in the visual system at this level. For example, retinogenicular protections were labeled using fluorescent choleric toxin. Coronal sections representing left and right geniculate nuclei of Wt and α6−/− animals were studied following injection with choleric toxin coupled with 2 different fluorophores, one for each eye. The labels did not superimpose, characteristic of normal segregation.

b) The Dopaminergic System

In the dopaminergic system, the inventors have verified the absence of an anatomical anomaly, both as regards cellular bodies (in the mesencephalus) and in their projections in the striatum. They studied the expression profile of a number of dopaminergic markers the majority of which are known to be influenced by nicotine administration. These markers include the dopaminergic tyrosine hydroxylase enzymes (TH) and dopamine transporter (DAT), dopamine receptors D1 and D2 and neuropeptides (cholecystokinine (CCK), preproenkephaline (PPE) and preprotakikinine (PPT)). Once again, no difference was detected in the expression profile of these markers in the brain of α6−/− animals.

4) Pharmacology of Nicotinic Receptors Containing the α6 Subunit 4.1. Profile of Conventional Nicotinic Ligand Bonds:

The distribution of binding sites for a variety of nicotinic ligands in the brain of α6−/− animals was studied. While the [$^{125}$I]α-bungarotoxin bond was not modified in the mutants, the epibatidine, cytisine and nicotine bond has shown a reduction in the number of sites with high affinity for these ligands in the retinal projection region (superior colliculus (SC) and the dorso-lateral geniculate nucleus (dLGN)). In contrast, in all other structures, in particular the SN/VTA and the striatum, no other difference could be detected by comparison with the Wt animals. This result, which was somewhat surprising, can be explained by the abundance of type α4β2 nicotinic receptors in these regions which could have masked small variations in the total number of sites.

4.2. Iodized α-Conotoxin MII Bond ([$^{125}$I]αCtxMII)

The most surprising result of this pharmacological study derives from a study of the αCtxMII bond. Indeed, this toxin was isolated and characterized as being specific for nAChRs containing a α3β2 interface (Cartier et al., 1996 J Biol Chem 271, 7522-8). Autoradiographic analysis of binding of αCtxMII to brain sections of wild type and mutant mice demonstrates the presence of binding sites in three major anatomical systems: the visual system (dorsolateral geniculate nucleus, ventrolateral geniculate nucleus, superior colliculus, olivary pretectal nucleus, and optic tract), the mesolimibic dopaminergic system (substantia nigra, ventral tegemental area, nucleus accumbens, and striatum), and the interpeduncular habenulo system (interpeduncular nucleus and medial habenula). However, the inventors have shown in α6−/− animals complete disappearance of all of the high affinity binding sites for this toxin. Further, since other possible sites, termed low affinity sites, could not be detected by this autoradiographic technique, the displacement of the [$^{3}$H] epibatidin bond by unlabeled αCtxMII on striatum membrane preparations was studied. Here again, the inventors have been able top show the total disappearance of sites with high and low affinity for αCtxMII(20% of the total number of epibatidine sites) in α6−/−. A further result arises from this study: while 20% of the binding sites for epibatidin were sensitive to αCtxMII and this sensitivity disappeared in the mutants, the inventors could not show a reduction in the total number of epibatidine sites in α6−/− animals. It appears that sites sensitive to a αCtxMII were replaced in the mutants by an equivalent quantity of resistant sited. The mechanism for this compensation remains unknown despite several hypothesis being postulated. In light of the inventors' results, it is not very likely that the compensation mechanism is transcriptional in nature. In contrast (Klinik et al., 2001 J Neurosci 21, 1452-63) have suggested the existence of α4α6(β2)$_3$ type sites in dopaminergic neurons. In the absence of the α6 subunit, these sites would not disappear but would be replaced by (α4)$_2$(β2)$_3$ type sites which are insensitive to αCtxMII.

5) The α6 Subunit Intervenes in Nicotinic Modulation of Dopaminergic Transmission.

5.1. Effect of Nicotine on Dopamine Release

Despite these compensation mechanisms, the inventors studied dopamine release induced by nicotine in striatal synaptosome preparations. In a wild type animal, administering nicotine (3 μM) induced an increase in dopamine release (DA) of about 100% over the basal level. In α6−/− and α4−/− animals, this release peak was reduced to 50%. Further, in α4−/−α6−/− double mutants, and in α2−/− animals, the effect of the nicotine was completely absent.

5.2. Effect of αCtxMII on the Release of Dopamine Induced by Nicotine

The inventors also studied the interaction of αCtxMII with the release of DA induced by nicotine in α4−/−, α6−/− and Wt animals.

In Wt animals, αCtxMII(100 nM) reduced the DA release peak induced by nicotine to 50% above the basal level. In contrast, in the α6−/− animals, the release of DA induced by nicotine was completely insensitive to αCtxMII, while it was completely abolished in α4−/−animals.

These results suggest the presence of 2 types of receptors in the dopaminergic termini in the striatum, each contributing 50% of the nicotine effect. They are the α4β2 type receptors that are insensitive to αCtxMII and α6β2 type receptors blocked by this toxin. However, close examination of the dose-response curves in α4 and α6 knockout mice showed a change in the affinity of the response of α4−/− mutant animals (drop of one order of magnitude). In the light of the results obtained with α6−/− animals, this can only be explained by a modification in the composition of the nicotinic receptors involved in the release of dopamine induced by nicotine. This led the inventors to modify their theory on the composition of the nicotinic receptors present on the dopaminergic termini in the striatum. They propose two types of receptors, $(α4)_2(β2)_3$ and $α6α4(β2)_3$ which would each contribute 50% of the nicotine response, and each having the same affinity for nicotine. In α6−/− animals, only the sub-type $(α4)_2(β2)_3$ would subsist inducing a response that was reduced by 50% insensitive to αCtxMII. In contrast, in α4−/− animals, the inventors suggest the formation of a novel sub type $(α6)_2(β2)_3$ that is sensitive to αCtxMII and with a lower affinity for nicotine (which would explain the change in the affinity of the nicotine response observed in α4−/− animals). The compensation mechanism described in α6−/− animals would also be present in α4−/− mutants. In contrast, the 50% reduction in the dopaminergic response on administration of nicotine to α6−/− animals indicates that the compensation observed in these animals is not functional.

5.3. Study of cFos Expression in Response to Nicotine

The inventors studied the expression of "early" genes in response to nicotine in α6−/− animals. These genes are transcription factors that are expressed in cells in response to very diverse stimuli translating a "genetic" activation of the cell in which they are expressed. In the case of drug addiction, an increase in expression of one of these genes, cFos, has been observed in response to administration of morphine, cocaine or nicotine in the cells of the striatum. This effect, which is blocked by infusion of dopaminergic antagonists into the striatum, is assumed to be responsible for long term modifications observed during chronic drug taking (Nestler, 2001 Nat Rev Neurosci 2, 119-28). In α6−/− animals, preliminary results appear to indicate an absence of activation of cFos expression in response to nicotine. These results, however, have to be confirmed on a larger number of animals and extended to other early genes.

The invention also includes the use of a non-human mammal, cell culture, or preparation of cells for any of the following: studying the effects of given substances on nicotinic receptors; studying the effects of addictive drugs on nicotinic receptors; determining the effect of agonists of the nicotinic acetylcholine receptors (nAChR) on dopamine release; screening nAChR agonist or antagonist substances; and screening agonist or antagonist substances of the nicotinic acetylcholine receptors of catecholaminergic or dopaminergic neurons.

The invention claimed is:

1. A mouse whose genome does not comprise an nAChR alpha6 subunit allele that expresses an nAChR alpha6 subunit;
   wherein the genome of the mouse comprises inactivated nAChR alpha6 subunit alleles inactivated by deletions, the inactivated nAChR alpha6 subunit alleles being present in the germline and somatic cells of the mouse, wherein the inactivated nAChR alpha6 subunit alleles no longer express an nAChR alpha6 subunit, and wherein the mouse has a phenotype of insensitivity to α-conotoxin MII (αCtxMII)-dependent inhibition of nicotine-induced dopamine release.

2. The mouse according to claim 1, wherein the inactivated nAChR alpha6 subunit alleles comprise a deletion of one or more exons of the gene coding for the nAChR alpha6 subunit.

3. The mouse according to claim 1, wherein the inactivated nAChR alpha6 subunit alleles comprise a deletion selected from a deletion comprising at least a portion of exon 1, at least a portion of exon 2, at least portions of exons 1 and 2, all of exon 1, all of exon 2, and all of exons 1 and 2.

4. The mouse according to claim 3, wherein the inactivated nAChR alpha6 subunit alleles comprise a deletion comprising all of exons 1 and 2.

5. The mouse according to claim 1, whose genome further does not comprise an nAChR alpha4 subunit allele that expresses an nAChR alpha4 subunit, said genome comprising at least one functional allele coding for the nAChR beta2 subunit, wherein the mouse has a phenotype of insensitivity of dopamine release at striatal synapses to nicotine.

6. The mouse according to claim 1, wherein the brain of the mouse lacks autoradiographically detectable high affinity binding sites for αCtxMII.

7. A mouse whose genome does not comprise an nAChR alpha6 subunit allele that expresses an nAChR alpha6 subunit;

wherein the genome of the mouse comprises inactivated nAChR alpha6 subunit alleles inactivated by deletions, the inactivated nAChR alpha6 subunit alleles being present in the germline and somatic cells of the mouse, wherein the inactivated nAChR alpha6 subunit alleles no longer express an nAChR alpha6 subunit, and wherein the mouse has a phenotype of an increased amount of striatal membrane epibaditine binding sites that are resistant to α-conotoxin MII (αCtxMII).

8. The mouse according to claim 7, wherein the inactivated nAChR alpha6 subunit alleles comprise a deletion of one or more exons of the gene coding for the nAChR alpha6 subunit.

9. The mouse according to claim 7, wherein the inactivated nAChR alpha6 subunit alleles comprise a deletion selected from a deletion comprising at least a portion of exon 1, at least a portion of exon 2, at least portions of exons 1 and 2, all of exon 1, all of exon 2, and all of exons 1 and 2.

10. The mouse according to claim 9, wherein the inactivated nAChR alpha6 subunit alleles comprise a deletion comprising all of exons 1 and 2.

11. The mouse according to claim 7, wherein the amount of striatal membrane epibaditine binding sites that are resistant to α-conotoxin MII is increased by at least 10%.

* * * * *

```
                        SEQUENCE LISTING

<160> NUMBER OF SEQ ID NOS: 7

<210> SEQ ID NO 1
<211> LENGTH: 23
<212> TYPE: DNA
<213> ORGANISM: Artificial
<220> FEATURE:
<223> OTHER INFORMATION: Forward Primer

<400> SEQUENCE: 1
actgctgtga agagatttac aca                                              23

<210> SEQ ID NO 2
<211> LENGTH: 21
<212> TYPE: DNA
<213> ORGANISM: Artificial
<220> FEATURE:
<223> OTHER INFORMATION: Reverse primer

<400> SEQUENCE: 2
aagatggtct tcacccactt g                                                21

<210> SEQ ID NO 3
<211> LENGTH: 4494
<212> TYPE: DNA
<213> ORGANISM: Artificial
<220> FEATURE:
<223> OTHER INFORMATION: Plasmid
<220> FEATURE:
<221> NAME/KEY: misc_feature
<222> LOCATION: (596)..(1115)
<223> OTHER INFORMATION: n equals a, t, g, or c
<220> FEATURE:
<221> NAME/KEY: misc_feature
<222> LOCATION: (1224)..(2286)
<223> OTHER INFORMATION: n equals a, t, g, or c

<400> SEQUENCE: 3
aagctttatg ggccaaggtg gtgagaaaag attcacagag gaggtgaaat ccaaatgatc      60
```

-continued

| | |
|---|---|
| tttgatcaat attttaagtc acatgtcatt tctaagtcaa cagagcagag gcaactggaa | 120 |
| acgttcggga tttctgttac agttaaatag ctttcatgca gtctccagtc ttcatgtctg | 180 |
| acttcattag cacggataac ttagatttgt ctattttag atataattct ctagttaaga | 240 |
| cttgtattag caagcacata gaagactgaa aaatattatt tcttccttcc aggatgaagt | 300 |
| caaccagatt atggagacca atctgtggct gcgtcacgta tgtgtccccc cctttgaatg | 360 |
| gcggcagaat gtatccactt agtgataaag ccacctgcat taacttttc gcaccccaac | 420 |
| ctatgataga taaagaatat ccttttcctt gctttctcct agtccttggg tcagctctgg | 480 |
| ttgcagttat attaatatag gcagcacatg ggcagagcct ggtgtctgac atggaaccct | 540 |
| ctggcctttc tcttttaagc tcccagttct ctttgtatca cttactgata ccaagnnnnn | 600 |
| nnnnnnnnnn nnnnnnnnnn nnnnnnnnnn nnnnnnnnnn nnnnnnnnnn nnnnnnnnnn | 660 |
| nnnnnnnnnn nnnnnnnnnn nnnnnnnnnn nnnnnnnnnn nnnnnnnnnn nnnnnnnnnn | 720 |
| nnnnnnnnnn nnnnnnnnnn nnnnnnnnnn nnnnnnnnnn nnnnnnnnnn nnnnnnnnnn | 780 |
| nnnnnnnnnn nnnnnnnnnn nnnnnnnnnn nnnnnnnnnn nnnnnnnnnn nnnnnnnnnn | 840 |
| nnnnnnnnnn nnnnnnnnnn nnnnnnnnnn nnnnnnnnnn nnnnnnnnnn nnnnnnnnnn | 900 |
| nnnnnnnnnn nnnnnnnnnn nnnnnnnnnn nnnnnnnnnn nnnnnnnnnn nnnnnnnnnn | 960 |
| nnnnnnnnnn nnnnnnnnnn nnnnnnnnnn nnnnnnnnnn nnnnnnnnnn nnnnnnnnnn | 1020 |
| nnnnnnnnnn nnnnnnnnnn nnnnnnnnnn nnnnnnnnnn nnnnnnnnnn nnnnnnnnnn | 1080 |
| nnnnnnnnnn nnnnnnnnnn nnnnnnnnnn nnnnnatctg gaaggactac agattgcgtt | 1140 |
| gggatccaac ggagtatgat ggcatcgaga cacttcgagt tccagcagac aacatctgga | 1200 |
| agcctgacat cgttctgtat aacnnnnnnn nnnnnnnnnn nnnnnnnnnn nnnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn nnnnnnnnnn nnnnnnnnnn | 1380 |
| nnnnnnnnnn nnnnnnnnnn nnnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nnnnnnnnnn nnnnnnnnnn nnnnnnnnnn nnnnnnnnnn nnnnnnnnnn nnnnnnnnnn | 1560 |
| nnnnnnnnnn nnnnnnnnnn nnnnnnnnnn nnnnnnnnnn nnnnnnnnnn nnnnnnnnnn | 1620 |
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnn | 1740 |
| nnnnnnnnnn nnnnnnnnnn nnnnnnnnnn nnnnnnnnnn nnnnnnnnnn nnnnnnnnnn | 1800 |
| nnnnnnnnnn nnnnnnnnnn nnnnnnnnnn nnnnnnnnnn nnnnnnnnnn nnnnnnnnnn | 1860 |
| nnnnnnnnnn nnnnnnnnnn nnnnnnnnnn nnnnnnnnnn nnnnnnnnnn nnnnnnnnnn | 1920 |
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnnnnn nnnnnnnnnn | 2220 |
| nnnnnnnnnn nnnnnnnnnn nnnnnnnnnn nnnnnnnnnn nnnnnnnnnn nnnnnnnnnn | 2280 |
| nnnnnnaatg ctgtcggcga cttccaggtc gaaggcaaga ccaaagctct tctcaagtat | 2340 |
| gacggtgtga taacctggac cccaccagcc atctttaaga gctcctgccc aatggacatc | 2400 |

```
accttcttcc cgtttgacca tcaaaactgc tccctgaagt ttggttcctg gacttatgac   2460
aaggcagaaa tcgaccttct catcattggc tctaaagtag acatgaacga cttttgggaa   2520
aacagtgaat gggaaattgt cgacgcctct ggctataagc atgacatcaa gtacaactgc   2580
tgtgaagaga tttacacgga cataacctac tccttctaca tcaggaggtt gcccatgttt   2640
tacaccatca acctcatcat cccctgcctc ttcatttcct tcctcacggt gctggttttt   2700
taccttccct ccgactgtgg cgagaaagtg actctttgca tctccgttct gctttctctc   2760
actgtctttt tgctggtgat tacagagacc atcccatcca catctctcgt gatcccactg   2820
gtgggtgagt atctactgtt caccatgatc tttgtcacgc tgtccattgt ggtgaccgtg   2880
ttcgtgctga acatacacta caggacccca gcaacgcata ccatgcccaa gtgggtgaag   2940
accatcttcc ttcaggcctt ccctcgatt ctgatgatga ggaaacctct ggacaagaca   3000
aaggaggcag gaggtgttaa ggaccccaaa agccatacca agaggcctgc caaggtcaaa   3060
tttactcatc gaggagaatc caaacttcta aggaatgcc accctgcca aaatcaagt   3120 gacatagcac ctggaaagag aagatcaagc cagcagcctg cacggtgggt ggcagagaat   3180
tcagagcact cgtccgatgt tgaagatgtc atcgagagtt tcaattcat agcagaaaac   3240 atgaagagcc acaatgaaac aaacgaggta aaagtggagc ccttttctcc agccagctgc   3300 accctagca ggcctacagg cactttagag actagtcaga gcgtcagtgg gagttacata   3360
tgtggaacag tcagggaccg tcacctaaga ccagctctat tatcatgaag ccttgtggga   3420
cctgggttca gtttaggga gctatagtga gaggatatat gtagtcctac aacaaatctt   3480
cagcctgcat ttacttacgg tgaggtctag ccacagtgca catgcaggac aagccttcct   3540
caaggaacaa gcctccaatg catcgaacac tgacaaagtg agggtgggaa gggagactgt   3600
agaaatcatt attaataaaa tcccaccggc gggcttgcta cctgctctaa tggtttgtgt   3660
tcccaaatga acacacaca cacacacaca cacacacaca cacacacaca cagtctttgt   3720
gttttaatat gccgtataca gcacaatagc tgggccactg cctaccctcc atgctgttac   3780
tatacctccc gccaacaatc cccaagttat tacttactaa ttctatgtgc tatcttggtt   3840
gcccctagac ccagttgggc agcctctggg ccatgttttc cccggctatt tcaagtggtg   3900
gccatgtctc tctgtcctgc agtcttctca ggcctagcat ctcacctctt cctccacact   3960
ctcccggcat ggcagggtct cacttctcct cctcctcctc ctcctcctcc accacctcct   4020
ttctcctccc tccctcctcc ctcccctctt tcccctcccc ccttccttcc cagcctgaga   4080
actcctaaaa tcccacctct ccctgtcctt tccagctttg gctgttggca gctttattta   4140
ccaataagaa ccaactgcgg gcaggttccc agaaactaca ggcagacagt cccacgaaaa   4200 cagtttacg tggaccataa ttagcattca taatacgtgc agctacagag acacccaagg   4260
aaaagaagaa ctgtggtact gcctgaagcc ccagtggtga agatgcccc ttagcagtca   4320 gcagctccca tcacacttcc tctactagag ggggacccag acatgagtta aagacatctt   4380
gaagatgtgc tcagtatgca cacgtattcc gtgcctgtgt cccacactct aatgcctaga   4440
gcttggctcc tcctacccca agcaagtgct caaggatagg gagatcgcgg ccgc         4494
```

<210> SEQ ID NO 4
<211> LENGTH: 4006
<212> TYPE: DNA
<213> ORGANISM: Artificial
<220> FEATURE:
<223> OTHER INFORMATION: Plasmid
<220> FEATURE:
<221> NAME/KEY: misc_feature
<222> LOCATION: (700)..(1850)
<223> OTHER INFORMATION: n equals a, t, g, or c
<220> FEATURE:
<221> NAME/KEY: misc_feature
<222> LOCATION: (1990)..(2501)
<223> OTHER INFORMATION: n equals a, t, g, or c
<220> FEATURE:
<221> NAME/KEY: misc_feature
<222> LOCATION: (3207)..(3317)
<223> OTHER INFORMATION: n equals a, t, g, or c

<400> SEQUENCE: 4

| | | | | | |
|---|---|---|---|---|---|
| gaattcagag | agcttttatc | atgctgaaca | gccgggacca | gggaaacctg | cactccggtt      60 |
| tatgtctgtg | gctatgtgga | ttcctggctc | tctttaaagg | tgagttatta | cggcttatat     120 |
| cctagaatac | aattggtagt | gtgcatttcc | tcttctttct | catcttgtct | ggatccaaat     180 |
| aattagagga | ctttaattag | ttaggcttaa | cctaacagat | atgatttgga | aagtaaggta     240 |
| gagaaaacat | tgaagtacag | tataatattc | atacttcatc | tctccaacta | aaatatgctt     300 |
| ttccaattag | catacaaaat | catctgcttt | tgtagccatg | tatgctacca | atatgcttca     360 |
| tttacttacg | gtaatttgtt | agctgggact | tattagcctg | cgagtcctac | caatgtgtgt     420 |
| aattgtcctc | acttaggaaa | cctgtcttat | tgtctactaa | gagtgagctt | tcctgtctta     480 |
| aaagttggct | cagacctggc | tggtgcacac | acacacacac | acacacacac | acacacacac     540 |
| acacacacga | acaggcacac | atgcacacat | ctcggatgag | gtttcagggg | gtgctgatgg     600 |
| tgagctccag | agagaggaaa | cagtagcaac | agccaagaga | gctcactatc | ttctgaaaca     660 |
| atgttttcat | cctggttagt | tacacaggag | agaatgacag | nnnnnnnnnn | nnnnnnnnnn     720 |
| nnnnnnnnnn | nnnnnnnnnn | nnnnnnnnnn | nnnnnnnnnn | nnnnnnnnnn | nnnnnnnnnn     780 |
| nnnnnnnnnn | nnnnnnnnnn | nnnnnnnnnn | nnnnnnnnnn | nnnnnnnnnn | nnnnnnnnnn     840 |
| nnnnnnnnnn | nnnnnnnnnn | nnnnnnnnnn | nnnnnnnnnn | nnnnnnnnnn | nnnnnnnnnn     900 |
| nnnnnnnnnn | nnnnnnnnnn | nnnnnnnnnn | nnnnnnnnnn | nnnnnnnnnn | nnnnnnnnnn     960 |
| nnnnnnnnnn | nnnnnnnnnn | nnnnnnnnnn | nnnnnnnnnn | nnnnnnnnnn | nnnnnnnnnn    1020 |
| nnnnnnnnnn | nnnnnnnnnn | nnnnnnnnnn | nnnnnnnnnn | nnnnnnnnnn | nnnnnnnnnn    1080 |
| nnnnnnnnnn | nnnnnnnnnn | nnnnnnnnnn | nnnnnnnnnn | nnnnnnnnnn | nnnnnnnnnn    1140 |
| nnnnnnnnnn | nnnnnnnnnn | nnnnnnnnnn | nnnnnnnnnn | nnnnnnnnnn | nnnnnnnnnn    1200 |
| nnnnnnnnnn | nnnnnnnnnn | nnnnnnnnnn | nnnnnnnnnn | nnnnnnnnnn | nnnnnnnnnn    1260 |
| nnnnnnnnnn | nnnnnnnnnn | nnnnnnnnnn | nnnnnnnnnn | nnnnnnnnnn | nnnnnnnnnn    1320 |
| nnnnnnnnnn | nnnnnnnnnn | nnnnnnnnnn | nnnnnnnnnn | nnnnnnnnnn | nnnnnnnnnn    1380 |
| nnnnnnnnnn | nnnnnnnnnn | nnnnnnnnnn | nnnnnnnnnn | nnnnnnnnnn | nnnnnnnnnn    1440 |
| nnnnnnnnnn | nnnnnnnnnn | nnnnnnnnnn | nnnnnnnnnn | nnnnnnnnnn | nnnnnnnnnn    1500 |
| nnnnnnnnnn | nnnnnnnnnn | nnnnnnnnnn | nnnnnnnnnn | nnnnnnnnnn | nnnnnnnnnn    1560 |
| nnnnnnnnnn | nnnnnnnnnn | nnnnnnnnnn | nnnnnnnnnn | nnnnnnnnnn | nnnnnnnnnn    1620 |
| nnnnnnnnnn | nnnnnnnnnn | nnnnnnnnnn | nnnnnnnnnn | nnnnnnnnnn | nnnnnnnnnn    1680 |
| nnnnnnnnnn | nnnnnnnnnn | nnnnnnnnnn | nnnnnnnnnn | nnnnnnnnnn | nnnnnnnnnn    1740 |
| nnnnnnnnnn | nnnnnnnnnn | nnnnnnnnnn | nnnnnnnnnn | nnnnnnnnnn | nnnnnnnnnn    1800 |
| nnnnnnnnnn | nnnnnnnnnn | nnnnnnnnnn | nnnnnnnnnn | nnnnnnnnnn | gcagtacagg    1860 |
| ctgtgaatct | gaagagcagc | tcttccacag | gctgtttgct | cactacaacc | gcttcatccg    1920 |
| gccggtggag | aatgtctccg | atcccgtcac | ggtgcatctt | gaattggcaa | tcacgcaact    1980 |

```
ggccaatgtg nnnnnnnnnn nnnnnnnnnn nnnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnnnnnnnn nnnnnnnnnn nnnnnnnnnn nnnnnnnnnn   2460
nnnnnnnnnn nnnnnnnnnn nnnnnnnnnn nnnnnnnnnn nactccctgg gctgagcata   2520
tacaaaccat cacaccatgt ctgccagttg attgcagctt ttccagaaac tagtgcattt   2580
gaaaccatga ttcaaaattg ttcacctggg tgtcaactaa tattttcccg ataaagaggt   2640
ctaggctaat ggttccaaca acgtggtgtg gtactgtgtg tctctggcct cctcctccat   2700
tagggctcac tgagctcagt gtccattgaa atggtctgga gttgcatgaa gactatgatt   2760
tttccagagt aggtcctgac tcatgacatt ttctaacacc tccaaggttg tgtattcccc   2820
atgaatacac accatatgga gcctatccaa accatggaag tgtctcaagg gaggcaggcc   2880
tgttaagaat ggtactgata attagtgtca actccctgaa ctcacccagg ttttgaagac   2940
tatgacaggt ttaggccagt tacctctaag acctcacgga agtgaggcag cagagcctat   3000
ccagctttga ccaacagcta gtacatactt acccagcatc tgttagaccc tacagattca   3060
aggcgactca ataccagagg gccctaatca atagagggga atcactggga agctgtgcag   3120
gctccatttt cctaagtctt tttgttgact ttaccaatcc cagggcctgt gttggctcca   3180
catgacccac tggcagggag aagcttnnnn nnnnnnnnnn nnnnnnnnnn nnnnnnnnnn   3240
nnnnnnnnnn nnnnnnnnnn nnnnnnnnnn nnnnnnnnnn nnnnnnnnnn nnnnnnnnnn   3300
nnnnnnnnnn nnnnnnncct gcgtagaaac ctcaaccagg ctgggatcct tcactcacag   3360
ggacctcaga tgtcttggaa aatgaaattt tgaatcccct gctgactgct aagaacctac   3420
tattaatacc caagctattc tgctgtgacc tgtcacctgt cctgactctc cttatgtcac   3480
ttcagggact gcttggacag taactcttca aagaagcctc cttgactcgt atattaaata   3540
gatgtgtgca tacacgcagg aatcactcca cctctcttgt tatatcatga tgtgttttat   3600
gctggcgtac acatttatta ttagctctgt ctttccaacc acaacagcta agagcacatg   3660
aaggcaggag cttcttcac tctgtaactt gagtggaact ctgtaacaca gtggtcactg   3720
ggtaagtagg aatatccctt gtgactgaag ggcccgtgag ctgggaaagg gaatacagag   3780
ggagtgagta cctggtttca actggcaaac ttgcatgtga actaaactgc tgtttcagtt   3840
tggatcccag ggcaaatgca cacagtacat cccaggcttc tttgaggaaa ggccatgggg   3900
atagataaaa acagtgagta cctgtcgcca cctacggaac tctccctct gtcgtccctg   3960 aacctctgcc ctcctccctg ttaccttca tgcatctagg aagctt                   4006
```

<210> SEQ ID NO 5
<211> LENGTH: 5023
<212> TYPE: DNA
<213> ORGANISM: Artificial
<220> FEATURE:
<223> OTHER INFORMATION: Plasmid
<220> FEATURE:
<221> NAME/KEY: misc_feature
<222> LOCATION: (1150)..(4311)
<223> OTHER INFORMATION: n equals a, t, g, or c

<400> SEQUENCE: 5

```
ctgcaggaat tcttaggcaa atggatggaa ctagaaaata tcatcctgag tgaggtaacc        60
caatcacaaa agaacataca tggtatgcac tcactgataa gtggatatta cccccaaagt       120
ttggaatatc caagatacaa ttcacagacc aaatgaagct caagaagaag gaagaacaaa       180
gtatggatac ttcagtcttt cttagaaggg ggaacaaaat actcatggga ggagatacag       240
agacaaagtg tggagcagag actgaaggaa aagccattca gagactgccc cagctgggga       300
tccatcccat atacagtcac caaacccaga cactattgtt gatgccaaca agtgcatgct       360
gacaggagtc tgacatagct gtctcctgag aggctctgcc agtgcctgac aaatatagag       420
gggatgctca cagccaacca ctggactgag cacagggtcc tcaatggagg agttagagaa       480
aggactgaag gaccagaaga ggtttgcagc cccataggag gaacaacaat atgaactagc       540
cagtatcccc agagctccca gggactaagc caccaaccaa agagtacata tgcaggaacc       600
catggctcca gctgcatatg tagcagagga tgtcacttct caatgggagg agaggccctt       660
ggtcctgaga aggctcaatg ccccagtgta ggggaatgcc aagacaggga agtgggagtg       720
tgtgggttgg tgagcagggg ggaggaggaa aggagtaggg ggtctttgga ggggaaacca       780
ggaaaggaga taacatttga aatgtaaatg aagaaaatat ctaatttttt aagaaagaaa       840
aaagacaatt acagacttag ctgtgcctgt agccactgtt ctcctagagt tcagagcctg       900
cctgtctggg accagacacc tctggctgag gtttcttgcc tggcattatg tgcagggtcc       960
ggctccattt tctcacccag ccctgccttc cacagctctg tgcacaggag aggatccaag      1020
gagaagggaa gtggaggtgg tggcgacagt gacccagttc agaaaggact ctgaggcaca      1080
ttcaatctat aaagtattca tggctctaaa agccttccaa ggggatccaa agcatttgct      1140
gagctgcagn nnnnnnnnn nnnnnnnnnn nnnnnnnnnn nnnnnnnnnn nnnnnnnnnn      1200
nnnnnnnnnn nnnnnnnnnn nnnnnnnnnn nnnnnnnnnn nnnnnnnnnn nnnnnnnnnn      1260
nnnnnnnnnn nnnnnnnnnn nnnnnnnnnn nnnnnnnnnn nnnnnnnnnn nnnnnnnnnn      1320
nnnnnnnnnn nnnnnnnnnn nnnnnnnnnn nnnnnnnnnn nnnnnnnnnn nnnnnnnnnn      1380
nnnnnnnnnn nnnnnnnnnn nnnnnnnnnn nnnnnnnnnn nnnnnnnnnn nnnnnnnnnn      1440
nnnnnnnnnn nnnnnnnnnn nnnnnnnnnn nnnnnnnnnn nnnnnnnnnn nnnnnnnnnn      1500
nnnnnnnnnn nnnnnnnnnn nnnnnnnnnn nnnnnnnnnn nnnnnnnnnn nnnnnnnnnn      1560
nnnnnnnnnn nnnnnnnnnn nnnnnnnnnn nnnnnnnnnn nnnnnnnnnn nnnnnnnnnn      1620
nnnnnnnnnn nnnnnnnnnn nnnnnnnnnn nnnnnnnnnn nnnnnnnnnn nnnnnnnnnn      1680
nnnnnnnnnn nnnnnnnnnn nnnnnnnnnn nnnnnnnnnn nnnnnnnnnn nnnnnnnnnn      1740
nnnnnnnnnn nnnnnnnnnn nnnnnnnnnn nnnnnnnnnn nnnnnnnnnn nnnnnnnnnn      1800
nnnnnnnnnn nnnnnnnnnn nnnnnnnnnn nnnnnnnnnn nnnnnnnnnn nnnnnnnnnn      1860
nnnnnnnnnn nnnnnnnnnn nnnnnnnnnn nnnnnnnnnn nnnnnnnnnn nnnnnnnnnn      1920
nnnnnnnnnn nnnnnnnnnn nnnnnnnnnn nnnnnnnnnn nnnnnnnnnn nnnnnnnnnn      1980
nnnnnnnnnn nnnnnnnnnn nnnnnnnnnn nnnnnnnnnn nnnnnnnnnn nnnnnnnnnn      2040
nnnnnnnnnn nnnnnnnnnn nnnnnnnnnn nnnnnnnnnn nnnnnnnnnn nnnnnnnnnn      2100
nnnnnnnnnn nnnnnnnnnn nnnnnnnnnn nnnnnnnnnn nnnnnnnnnn nnnnnnnnnn      2160
nnnnnnnnnn nnnnnnnnnn nnnnnnnnnn nnnnnnnnnn nnnnnnnnnn nnnnnnnnnn      2220
nnnnnnnnnn nnnnnnnnnn nnnnnnnnnn nnnnnnnnnn nnnnnnnnnn nnnnnnnnnn      2280
```

| | |
|---|---|
| nnnnnnnnnn nnnnnnnnnn nnnnnnnnnn nnnnnnnnnn nnnnnnnnnn nnnnnnnnnn | 2340 |
| nnnnnnnnnn nnnnnnnnnn nnnnnnnnnn nnnnnnnnnn nnnnnnnnnn nnnnnnnnnn | 2400 |
| nnnnnnnnnn nnnnnnnnnn nnnnnnnnnn nnnnnnnnnn nnnnnnnnnn nnnnnnnnnn | 2460 |
| nnnnnnnnnn nnnnnnnnnn nnnnnnnnnn nnnnnnnnnn nnnnnnnnnn nnnnnnnnnn | 2520 |
| nnnnnnnnnn nnnnnnnnnn nnnnnnnnnn nnnnnnnnnn nnnnnnnnnn nnnnnnnnnn | 2580 |
| nnnnnnnnnn nnnnnnnnnn nnnnnnnnnn nnnnnnnnnn nnnnnnnnnn nnnnnnnnnn | 2640 |
| nnnnnnnnnn nnnnnnnnnn nnnnnnnnnn nnnnnnnnnn nnnnnnnnnn nnnnnnnnnn | 2700 |
| nnnnnnnnnn nnnnnnnnnn nnnnnnnnnn nnnnnnnnnn nnnnnnnnnn nnnnnnnnnn | 2760 |
| nnnnnnnnnn nnnnnnnnnn nnnnnnnnnn nnnnnnnnnn nnnnnnnnnn nnnnnnnnnn | 2820 |
| nnnnnnnnnn nnnnnnnnnn nnnnnnnnnn nnnnnnnnnn nnnnnnnnnn nnnnnnnnnn | 2880 |
| nnnnnnnnnn nnnnnnnnnn nnnnnnnnnn nnnnnnnnnn nnnnnnnnnn nnnnnnnnnn | 2940 |
| nnnnnnnnnn nnnnnnnnnn nnnnnnnnnn nnnnnnnnnn nnnnnnnnnn nnnnnnnnnn | 3000 |
| nnnnnnnnnn nnnnnnnnnn nnnnnnnnnn nnnnnnnnnn nnnnnnnnnn nnnnnnnnnn | 3060 |
| nnnnnnnnnn nnnnnnnnnn nnnnnnnnnn nnnnnnnnnn nnnnnnnnnn nnnnnnnnnn | 3120 |
| nnnnnnnnnn nnnnnnnnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |
| nnnnnnnnnn nnnnnnnnnn nnnnnnnnnn nnnnnnnnnn nnnnnnnnnn nnnnnnnnnn | 3300 |
| nnnnnnnnnn nnnnnnnnnn nnnnnnnnnn nnnnnnnnnn nnnnnnnnnn nnnnnnnnnn | 3360 |
| nnnnnnnnnn nnnnnnnnnn nnnnnnnnnn nnnnnnnnnn nnnnnnnnnn nnnnnnnnnn | 3420 |
| nnnnnnnnnn nnnnnnnnnn nnnnnnnnnn nnnnnnnnnn nnnnnnnnnn nnnnnnnnnn | 3480 |
| nnnnnnnnnn nnnnnnnnnn nnnnnnnnnn nnnnnnnnnn nnnnnnnnnn nnnnnnnnnn | 3540 |
| nnnnnnnnnn nnnnnnnnnn nnnnnnnnnn nnnnnnnnnn nnnnnnnnnn nnnnnnnnnn | 3600 |
| nnnnnnnnnn nnnnnnnnnn nnnnnnnnnn nnnnnnnnnn nnnnnnnnnn nnnnnnnnnn | 3660 |
| nnnnnnnnnn nnnnnnnnnn nnnnnnnnnn nnnnnnnnnn nnnnnnnnnn nnnnnnnnnn | 3720 |
| nnnnnnnnnn nnnnnnnnnn nnnnnnnnnn nnnnnnnnnn nnnnnnnnnn nnnnnnnnnn | 3780 |
| nnnnnnnnnn nnnnnnnnnn nnnnnnnnnn nnnnnnnnnn nnnnnnnnnn nnnnnnnnnn | 3840 |
| nnnnnnnnnn nnnnnnnnnn nnnnnnnnnn nnnnnnnnnn nnnnnnnnnn nnnnnnnnnn | 3900 |
| nnnnnnnnnn nnnnnnnnnn nnnnnnnnnn nnnnnnnnnn nnnnnnnnnn nnnnnnnnnn | 3960 |
| nnnnnnnnnn nnnnnnnnnn nnnnnnnnnn nnnnnnnnnn nnnnnnnnnn nnnnnnnnnn | 4020 |
| nnnnnnnnnn nnnnnnnnnn nnnnnnnnnn nnnnnnnnnn nnnnnnnnnn nnnnnnnnnn | 4080 |
| nnnnnnnnnn nnnnnnnnnn nnnnnnnnnn nnnnnnnnnn nnnnnnnnnn nnnnnnnnnn | 4140 |
| nnnnnnnnnn nnnnnnnnnn nnnnnnnnnn nnnnnnnnnn nnnnnnnnnn nnnnnnnnnn | 4200 |
| nnnnnnnnnn nnnnnnnnnn nnnnnnnnnn nnnnnnnnnn nnnnnnnnnn nnnnnnnnnn | 4260 |
| nnnnnnnnnn nnnnnnnnnn nnnnnnnnnn nnnnnnnnnn nnnnnnnnnn naactaggaa | 4320 |
| tatttcagac agatgcctaa ctgctaaggc tcagagaaac agcaaattaa gtggatatcc | 4380 |
| tttatggatg actgtgattt ttttttccta taatggaagc caagtaaata agatgctatt | 4440 |
| atcccactaa aagcagcggt tctcaacctc tgggtctcca cccttgagg tcaaatgaca | 4500 |
| cttttaccga gggtcatcta agacattgga aaacacagat atttacatta tgactcacaa | 4560 |
| ccgtagaaaa attacactta tgaagtagca acgaactaat tttatccttg aggaataggg | 4620 |
| ggggtcacca caacatgcag atctgtatta aagggttgca gcattaggaa ggtttagaac | 4680 |

```
cactgcccta agagtaggca agactgcagg tctctcatgg gacttgcctg tttgcctagt    4740
gtctcagcct gcctctcttc ttccctgcac agaggtctag ggtgacagga catgtgacag    4800
ccagccgagt gaagcagcag ggttggcttc ccttgccctt cacatctgtt tcagcctggg    4860
atgcagggag cagttgcatg atgtcccgtg ttttcacttc acagaagatc tgtgtgagct    4920
tccaggagct tcccggggct ttcaatatct gattctggca gctgacagac agctgtgtct    4980
tccacagccc tccgtgtaga aatcggaatt cgatatcaag ctt                      5023

<210> SEQ ID NO 6
<211> LENGTH: 4500
<212> TYPE: DNA
<213> ORGANISM: Artificial
<220> FEATURE:
<223> OTHER INFORMATION: Plasmid
<220> FEATURE:
<221> NAME/KEY: misc_feature
<222> LOCATION: (687)..(3357)
<223> OTHER INFORMATION: n equals a, t, g, or c

<400> SEQUENCE: 6
ctgcagaagc agcattaaga ctgtgctcta aatccaactc ctactttcct tggaagagac      60
acaagaaaaa gaggcaaggt gacagggcac agacaaagca ctgtagctac agatgcagag     120
atctgaatta ggaaactcta agccaaggca cacctggaat catcaatagc tggaaaagac     180
aagaaagatt ttctgtcaga gcctacagga agtctggct tgctaacac ctgcattttg      240 ggccattagc ctcagagctc tgaaatgata atattttgtt gtatttaccc accaaatttg     300
tggtgattta ttatgaggtc cctaggaaat aaataggact tggtatagtt ttttttttt     360 ttttcatttc caatcacaaa gcaagaatta ctgcaatgga attaaatttt atttcacaga     420
attgctggtt ctagtacaat ggtaccgatg ctgaaattgt ttctacatca ggagacttac     480
agtttaggca catttatttg tatgttgaag accccagata attactttga aaaagagaa     540 gtcaagaggc tggaatggag ttccagaatc cccagaatct tgtcttggaa accatttcca     600
ctacaggatg tccttcactg aagttgctga gtggtgccca tgcaggacta atgaatccac     660
tgaaagctgt gtggcttaac tggagannnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
```

| | |
|---|---|
| nnnnnnnnnn nnnnnnnnnn nnnnnnnnnn nnnnnnnnnn nnnnnnnnnn nnnnnnnnnn | 1620 |
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnn | 1740 |
| nnnnnnnnnn nnnnnnnnnn nnnnnnnnnn nnnnnnnnnn nnnnnnnnnn nnnnnnnnnn | 1800 |
| nnnnnnnnnn nnnnnnnnnn nnnnnnnnnn nnnnnnnnnn nnnnnnnnnn nnnnnnnnnn | 1860 |
| nnnnnnnnnn nnnnnnnnnn nnnnnnnnnn nnnnnnnnnn nnnnnnnnnn nnnnnnnnnn | 1920 |
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnnnnn nnnnnnnnnn | 2220 |
| nnnnnnnnnn nnnnnnnnnn nnnnnnnnnn nnnnnnnnnn nnnnnnnnnn nnnnnnnnnn | 2280 |
| nnnnnnnnnn nnnnnnnnnn nnnnnnnnnn nnnnnnnnnn nnnnnnnnnn nnnnnnnnnn | 2340 |
| nnnnnnnnnn nnnnnnnnnn nnnnnnnnnn nnnnnnnnnn nnnnnnnnnn nnnnnnnnnn | 2400 |
| nnnnnnnnnn nnnnnnnnnn nnnnnnnnnn nnnnnnnnnn nnnnnnnnnn nnnnnnnnnn | 2460 |
| nnnnnnnnnn nnnnnnnnnn nnnnnnnnnn nnnnnnnnnn nnnnnnnnnn nnnnnnnnnn | 2520 |
| nnnnnnnnnn nnnnnnnnnn nnnnnnnnnn nnnnnnnnnn nnnnnnnnnn nnnnnnnnnn | 2580 |
| nnnnnnnnnn nnnnnnnnnn nnnnnnnnnn nnnnnnnnnn nnnnnnnnnn nnnnnnnnnn | 2640 |
| nnnnnnnnnn nnnnnnnnnn nnnnnnnnnn nnnnnnnnnn nnnnnnnnnn nnnnnnnnnn | 2700 |
| nnnnnnnnnn nnnnnnnnnn nnnnnnnnnn nnnnnnnnnn nnnnnnnnnn nnnnnnnnnn | 2760 |
| nnnnnnnnnn nnnnnnnnnn nnnnnnnnnn nnnnnnnnnn nnnnnnnnnn nnnnnnnnnn | 2820 |
| nnnnnnnnnn nnnnnnnnnn nnnnnnnnnn nnnnnnnnnn nnnnnnnnnn nnnnnnnnnn | 2880 |
| nnnnnnnnnn nnnnnnnnnn nnnnnnnnnn nnnnnnnnnn nnnnnnnnnn nnnnnnnnnn | 2940 |
| nnnnnnnnnn nnnnnnnnnn nnnnnnnnnn nnnnnnnnnn nnnnnnnnnn nnnnnnnnnn | 3000 |
| nnnnnnnnnn nnnnnnnnnn nnnnnnnnnn nnnnnnnnnn nnnnnnnnnn nnnnnnnnnn | 3060 |
| nnnnnnnnnn nnnnnnnnnn nnnnnnnnnn nnnnnnnnnn nnnnnnnnnn nnnnnnnnnn | 3120 |
| nnnnnnnnnn nnnnnnnnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |
| nnnnnnnnnn nnnnnnnnnn nnnnnnnnnn nnnnnnnnnn nnnnnnnnnn nnnnnnnnnn | 3300 |
| nnnnnnnnnn nnnnnnnnnn nnnnnnnnnn nnnnnnnnnn nnnnnnnnnn nnnnnnngaa | 3360 |
| ttcttaggca aatggatgga actagaaaat atcatcctga gtgaggtaac ccaatcacaa | 3420 |
| aagaacatac atggtatgca ctcactgata agtggatatt accccaaag tttggaatat | 3480 |
| ccaagataca attcacagac caaatgaagc tcaagaagaa ggaagaacaa agtatggata | 3540 |
| cttcagtctt tcttagaagg gggaacaaaa tactcatggg aggagataca gagacaaagt | 3600 |
| gtggagcaga gactgaagga aaagccattc agagactgcc ccagctgggg atccatccca | 3660 |
| tatacagtca ccaaacccag acactattgt tgatgccaac aagtgcatgc tgacaggagt | 3720 |
| ctgcatagc tgtctcctga gaggctctgc cagtgcctga caaatataga ggggatgctc | 3780 |
| acagccaacc actggactga gcacagggtc tcaatggag gagttagaga aaggactgaa | 3840 |
| ggaccagaag aggtttgcag ccccatagga ggaacaacaa tatgaactag ccagtatccc | 3900 |
| cagagctccc agggactaag ccaccaacca aagagtacat atgcaggaac ccatggctcc | 3960 |

-continued

```
agctgcatat gtagcagagg atgtcacttc tcaatgggag gagaggccct tggtcctgag    4020
aaggctcaat gccccagtgt aggggaatgc caagacaggg aagtgggagt gtgtgggttg    4080
gtgagcaggg gggaggagga aaggagtagg gggtctttgg aggggaaacc aggaaaggag    4140
ataacatttg aaatgtaaat gaagaaaata tctaattttt taagaaagaa aaaagacaat    4200
tacagactta gctgtgcctg tagccactgt tctcctagag ttcagagcct gcctgtctgg    4260
gaccagacac ctctggctga ggtttcttgc ctggcattat gtgcagggtc cggctccatt    4320
ttctcaccca gccctgcctt ccacagctct gtgcacagga gaggatccaa ggagaaggga    4380
agtggaggtg gtggcgacag tgacccagtt cagaaaggac tctgaggcac attcaatcta    4440
taaagtattc atggctctaa aagccttcca aggggatcca aagcatttgc tgagctgcag    4500
```

```
<210> SEQ ID NO 7
<211> LENGTH: 17758
<212> TYPE: DNA
<213> ORGANISM: Mus musculus
<220> FEATURE:
<221> NAME/KEY: misc_feature
<222> LOCATION: (687)..(3357)
<223> OTHER INFORMATION: n equals a, t, g, or c
<220> FEATURE:
<221> NAME/KEY: misc_feature
<222> LOCATION: (4501)..(5357)
<223> OTHER INFORMATION: n equals a, t, g, or c
<220> FEATURE:
<221> NAME/KEY: misc_feature
<222> LOCATION: (5363)..(5863)
<223> OTHER INFORMATION: n equals a, t, g, or c
<220> FEATURE:
<221> NAME/KEY: misc_feature
<222> LOCATION: (5870)..(6320)
<223> OTHER INFORMATION: n equals a, t, g, or c
<220> FEATURE:
<221> NAME/KEY: misc_feature
<222> LOCATION: (6327)..(7662)
<223> OTHER INFORMATION: n equals a, t, g, or c
<220> FEATURE:
<221> NAME/KEY: misc_feature
<222> LOCATION: (9045)..(9155)
<223> OTHER INFORMATION: n equals a, t, g, or c
<220> FEATURE:
<221> NAME/KEY: misc_feature
<222> LOCATION: (9162)..(9456)
<223> OTHER INFORMATION: n equals a, t, g, or c
<220> FEATURE:
<221> NAME/KEY: misc_feature
<222> LOCATION: (9463)..(10206)
<223> OTHER INFORMATION: n equals a, t, g, or c
<220> FEATURE:
<221> NAME/KEY: misc_feature
<222> LOCATION: (10347)..(10607)
<223> OTHER INFORMATION: n equals a, t, g, or c
<220> FEATURE:
<221> NAME/KEY: misc_feature
<222> LOCATION: (10613)..(10857)
<223> OTHER INFORMATION: n equals a, t, g, or c
<220> FEATURE:
<221> NAME/KEY: misc_feature
<222> LOCATION: (11563)..(11673)
<223> OTHER INFORMATION: n equals a, t, g, or c
<220> FEATURE:
<221> NAME/KEY: misc_feature
<222> LOCATION: (12952)..(13471)
<223> OTHER INFORMATION: n equals a, t, g, or c
<220> FEATURE:
<221> NAME/KEY: misc_feature
<222> LOCATION: (13580)..(13588)
<223> OTHER INFORMATION: n equals a, t, g, or c
<220> FEATURE:
<221> NAME/KEY: misc_feature
<222> LOCATION: (13595)..(13692)
```

-continued

```
<223> OTHER INFORMATION: n equals a, t, g, or c
<220> FEATURE:
<221> NAME/KEY: misc_feature
<222> LOCATION: (13699)..(14236)
<223> OTHER INFORMATION: n equals a, t, g, or c
<220> FEATURE:
<221> NAME/KEY: misc_feature
<222> LOCATION: (14243)..(14642)
<223> OTHER INFORMATION: n equals a, t, g, or c
<220> FEATURE:
<221> NAME/KEY: misc_feature
<222> LOCATION: (17075)..(17238)
<223> OTHER INFORMATION: n equals a, t, g, or c

<400> SEQUENCE: 7
ctgcagaagc agcattaaga ctgtgctcta aatccaactc ctactttcct tggaagagac      60
acaagaaaaa gaggcaaggt gacagggcac agacaaagca ctgtagctac agatgcagag     120
atctgaatta ggaaactcta agccaaggca cacctggaat catcaatagc tggaaaagac     180
aagaaagatt ttctgtcaga gcctacagga aagtctggct ttgctaacac ctgcattttg     240
ggccattagc ctcagagctc tgaaatgata atattttgtt gtatttaccc accaaatttg     300
tggtgattta ttatgaggtc cctaggaaat aaataggact tggtatagtt ttttttttt     360
ttttcatttc caatcacaaa gcaagaatta ctgcaatgga attaaatttt atttcacaga     420
attgctggtt ctagtacaat ggtaccgatg ctgaaattgt ttctacatca ggagacttac     480
agtttaggca catttatttg tatgttgaag accccagata attactttga aaaagagaa     540
gtcaagaggc tggaatggag ttccagaatc cccagaatct tgtcttggaa accatttcca     600
ctacaggatg tccttcactg aagttgctga gtggtgccca tgcaggacta atgaatccac     660
tgaaagctgt gtggcttaac tggagannnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
```

| | |
|---|---|
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnnnnn nnnnnnnnnn | 2220 |
| nnnnnnnnnn nnnnnnnnnn nnnnnnnnnn nnnnnnnnnn nnnnnnnnnn nnnnnnnnnn | 2280 |
| nnnnnnnnnn nnnnnnnnnn nnnnnnnnnn nnnnnnnnnn nnnnnnnnnn nnnnnnnnnn | 2340 |
| nnnnnnnnnn nnnnnnnnnn nnnnnnnnnn nnnnnnnnnn nnnnnnnnnn nnnnnnnnnn | 2400 |
| nnnnnnnnnn nnnnnnnnnn nnnnnnnnnn nnnnnnnnnn nnnnnnnnnn nnnnnnnnnn | 2460 |
| nnnnnnnnnn nnnnnnnnnn nnnnnnnnnn nnnnnnnnnn nnnnnnnnnn nnnnnnnnnn | 2520 |
| nnnnnnnnnn nnnnnnnnnn nnnnnnnnnn nnnnnnnnnn nnnnnnnnnn nnnnnnnnnn | 2580 |
| nnnnnnnnnn nnnnnnnnnn nnnnnnnnnn nnnnnnnnnn nnnnnnnnnn nnnnnnnnnn | 2640 |
| nnnnnnnnnn nnnnnnnnnn nnnnnnnnnn nnnnnnnnnn nnnnnnnnnn nnnnnnnnnn | 2700 |
| nnnnnnnnnn nnnnnnnnnn nnnnnnnnnn nnnnnnnnnn nnnnnnnnnn nnnnnnnnnn | 2760 |
| nnnnnnnnnn nnnnnnnnnn nnnnnnnnnn nnnnnnnnnn nnnnnnnnnn nnnnnnnnnn | 2820 |
| nnnnnnnnnn nnnnnnnnnn nnnnnnnnnn nnnnnnnnnn nnnnnnnnnn nnnnnnnnnn | 2880 |
| nnnnnnnnnn nnnnnnnnnn nnnnnnnnnn nnnnnnnnnn nnnnnnnnnn nnnnnnnnnn | 2940 |
| nnnnnnnnnn nnnnnnnnnn nnnnnnnnnn nnnnnnnnnn nnnnnnnnnn nnnnnnnnnn | 3000 |
| nnnnnnnnnn nnnnnnnnnn nnnnnnnnnn nnnnnnnnnn nnnnnnnnnn nnnnnnnnnn | 3060 |
| nnnnnnnnnn nnnnnnnnnn nnnnnnnnnn nnnnnnnnnn nnnnnnnnnn nnnnnnnnnn | 3120 |
| nnnnnnnnnn nnnnnnnnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |
| nnnnnnnnnn nnnnnnnnnn nnnnnnnnnn nnnnnnnnnn nnnnnnnnnn nnnnnnnnnn | 3300 |
| nnnnnnnnnn nnnnnnnnnn nnnnnnnnnn nnnnnnnnnn nnnnnnnnnn nnnnnnngaa | 3360 |
| ttcttaggca aatggatgga actagaaaat atcatcctga gtgaggtaac ccaatcacaa | 3420 |
| aagaacatac atggtatgca ctcactgata agtggatatt accccaaag tttggaatat | 3480 |
| ccaagataca attcacagac caaatgaagc tcaagaagaa ggaagaacaa agtatggata | 3540 |
| cttcagtctt tcttagaagg gggaacaaaa tactcatggg aggagataca gagacaaagt | 3600 |
| gtggagcaga gactgaagga aaagccattc agagactgcc ccagctgggg atccatccca | 3660 |
| tatacagtca ccaaacccag acactattgt tgatgccaac aagtgcatgc tgacaggagt | 3720 |
| ctgacatagc tgtctcctga gaggctctgc cagtgcctga caaatataga ggggatgctc | 3780 |
| acagccaacc actggactga gcacagggtc ctcaatggag gagttagaga aaggactgaa | 3840 |
| ggaccagaag aggtttgcag ccccatagga ggaacaacaa tatgaactag ccagtatccc | 3900 |
| cagagctccc agggactaag ccaccaacca aagagtacat atgcaggaac ccatggctcc | 3960 |
| agctgcatat gtagcagagg atgtcacttc tcaatgggag gagaggccct tggtcctgag | 4020 |
| aaggctcaat gccccagtgt agggggaatgc caagacaggg aagtgggagt gtgtgggttg | 4080 |
| gtgagcaggg gggaggagga aaggagtagg gggtctttgg aggggaaacc aggaaaggag | 4140 |
| ataacatttg aaatgtaaat gaagaaaata tctaattttt taagaaagaa aaaagacaat | 4200 |
| tacagactta gctgtgcctg tagccactgt tctcctagag ttcagagcct gcctgtctgg | 4260 |

-continued

```
gaccagacac ctctggctga ggtttcttgc ctggcattat gtgcagggtc cggctccatt    4320
ttctcaccca gccctgcctt ccacagctct gtgcacagga gaggatccaa ggagaaggga    4380
agtggaggtg gtggcgacag tgacccagtt cagaaaggac tctgaggcac attcaatcta    4440
taaagtattc atggctctaa aagccttcca aggggatcca aagcatttgc tgagctgcag    4500
nnnnnnnnnn nnnnnnnnnn nnnnnnnnnn nnnnnnnnnn nnnnnnnnnn nnnnnnnnnn    4560
nnnnnnnnnn nnnnnnnnnn nnnnnnnnnn nnnnnnnnnn nnnnnnnnnn nnnnnnnnnn    4620
nnnnnnnnnn nnnnnnnnnn nnnnnnnnnn nnnnnnnnnn nnnnnnnnnn nnnnnnnnnn    4680
nnnnnnnnnn nnnnnnnnnn nnnnnnnnnn nnnnnnnnnn nnnnnnnnnn nnnnnnnnnn    4740
nnnnnnnnnn nnnnnnnnnn nnnnnnnnnn nnnnnnnnnn nnnnnnnnnn nnnnnnnnnn    4800
nnnnnnnnnn nnnnnnnnnn nnnnnnnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnnnnnn nnnnnnnnnn nnnnnnnnnn nnnnnnnnnn nnnnnnnnnn nnnnnnnnnn    5040
nnnnnnnnnn nnnnnnnnnn nnnnnnnnnn nnnnnnnnnn nnnnnnnnnn nnnnnnnnnn    5100
nnnnnnnnnn nnnnnnnnnn nnnnnnnnnn nnnnnnnnnn nnnnnnnnnn nnnnnnnnnn    5160
nnnnnnnnnn nnnnnnnnnn nnnnnnnnnn nnnnnnnnnn nnnnnnnnnn nnnnnnnnnn    5220
nnnnnnnnnn nnnnnnnnnn nnnnnnnnnn nnnnnnnnnn nnnnnnnnnn nnnnnnnnnn    5280
nnnnnnnnnn nnnnnnnnnn nnnnnnnnnn nnnnnnnnnn nnnnnnnnnn nnnnnnnnnn    5340
nnnnnnnnnn nnnnnnaagc ttnnnnnnnn nnnnnnnnnn nnnnnnnnnn nnnnnnnnnn    5400
nnnnnnnnnn nnnnnnnnnn nnnnnnnnnn nnnnnnnnnn nnnnnnnnnn nnnnnnnnnn    5460
nnnnnnnnnn nnnnnnnnnn nnnnnnnnnn nnnnnnnnnn nnnnnnnnnn nnnnnnnnnn    5520
nnnnnnnnnn nnnnnnnnnn nnnnnnnnnn nnnnnnnnnn nnnnnnnnnn nnnnnnnnnn    5580
nnnnnnnnnn nnnnnnnnnn nnnnnnnnnn nnnnnnnnnn nnnnnnnnnn nnnnnnnnnn    5640
nnnnnnnnnn nnnnnnnnnn nnnnnnnnnn nnnnnnnnnn nnnnnnnnnn nnnnnnnnnn    5700
nnnnnnnnnn nnnnnnnnnn nnnnnnnnnn nnnnnnnnnn nnnnnnnnnn nnnnnnnnnn    5760
nnnnnnnnnn nnnnnnnnnn nnnnnnnnnn nnnnnnnnnn nnnnnnnnnn nnnnnnnnnn    5820
nnnnnnnnnn nnnnnnnnnn nnnnnnnnnn nnnnnnnnnn nnngcatgcn nnnnnnnnnn    5880
nnnnnnnnnn nnnnnnnnnn nnnnnnnnnn nnnnnnnnnn nnnnnnnnnn nnnnnnnnnn    5940
nnnnnnnnnn nnnnnnnnnn nnnnnnnnnn nnnnnnnnnn nnnnnnnnnn nnnnnnnnnn    6000
nnnnnnnnnn nnnnnnnnnn nnnnnnnnnn nnnnnnnnnn nnnnnnnnnn nnnnnnnnnn    6060
nnnnnnnnnn nnnnnnnnnn nnnnnnnnnn nnnnnnnnnn nnnnnnnnnn nnnnnnnnnn    6120
nnnnnnnnnn nnnnnnnnnn nnnnnnnnnn nnnnnnnnnn nnnnnnnnnn nnnnnnnnnn    6180
nnnnnnnnnn nnnnnnnnnn nnnnnnnnnn nnnnnnnnnn nnnnnnnnnn nnnnnnnnnn    6240
nnnnnnnnnn nnnnnnnnnn nnnnnnnnnn nnnnnnnnnn nnnnnnnnnn nnnnnnnnnn    6300
nnnnnnnnnn nnnnnnnnnn ccatggnnnn nnnnnnnnnn nnnnnnnnnn nnnnnnnnnn    6360
nnnnnnnnnn nnnnnnnnnn nnnnnnnnnn nnnnnnnnnn nnnnnnnnnn nnnnnnnnnn    6420
nnnnnnnnnn nnnnnnnnnn nnnnnnnnnn nnnnnnnnnn nnnnnnnnnn nnnnnnnnnn    6480
nnnnnnnnnn nnnnnnnnnn nnnnnnnnnn nnnnnnnnnn nnnnnnnnnn nnnnnnnnnn    6540
nnnnnnnnnn nnnnnnnnnn nnnnnnnnnn nnnnnnnnnn nnnnnnnnnn nnnnnnnnnn    6600
nnnnnnnnnn nnnnnnnnnn nnnnnnnnnn nnnnnnnnnn nnnnnnnnnn nnnnnnnnnn    6660
```

| | |
|---|---|
| nnnnnnnnnn nnnnnnnnnn nnnnnnnnnn nnnnnnnnnn nnnnnnnnnn nnnnnnnnnn | 6720 |
| nnnnnnnnnn nnnnnnnnnn nnnnnnnnnn nnnnnnnnnn nnnnnnnnnn nnnnnnnnnn | 6780 |
| nnnnnnnnnn nnnnnnnnnn nnnnnnnnnn nnnnnnnnnn nnnnnnnnnn nnnnnnnnnn | 6840 |
| nnnnnnnnnn nnnnnnnnnn nnnnnnnnnn nnnnnnnnnn nnnnnnnnnn nnnnnnnnnn | 6900 |
| nnnnnnnnnn nnnnnnnnnn nnnnnnnnnn nnnnnnnnnn nnnnnnnnnn nnnnnnnnnn | 6960 |
| nnnnnnnnnn nnnnnnnnnn nnnnnnnnnn nnnnnnnnnn nnnnnnnnnn nnnnnnnnnn | 7020 |
| nnnnnnnnnn nnnnnnnnnn nnnnnnnnnn nnnnnnnnnn nnnnnnnnnn nnnnnnnnnn | 7080 |
| nnnnnnnnnn nnnnnnnnnn nnnnnnnnnn nnnnnnnnnn nnnnnnnnnn nnnnnnnnnn | 7140 |
| nnnnnnnnnn nnnnnnnnnn nnnnnnnnnn nnnnnnnnnn nnnnnnnnnn nnnnnnnnnn | 7200 |
| nnnnnnnnnn nnnnnnnnnn nnnnnnnnnn nnnnnnnnnn nnnnnnnnnn nnnnnnnnnn | 7260 |
| nnnnnnnnnn nnnnnnnnnn nnnnnnnnnn nnnnnnnnnn nnnnnnnnnn nnnnnnnnnn | 7320 |
| nnnnnnnnnn nnnnnnnnnn nnnnnnnnnn nnnnnnnnnn nnnnnnnnnn nnnnnnnnnn | 7380 |
| nnnnnnnnnn nnnnnnnnnn nnnnnnnnnn nnnnnnnnnn nnnnnnnnnn nnnnnnnnnn | 7440 |
| nnnnnnnnnn nnnnnnnnnn nnnnnnnnnn nnnnnnnnnn nnnnnnnnnn nnnnnnnnnn | 7500 |
| nnnnnnnnnn nnnnnnnnnn nnnnnnnnnn nnnnnnnnnn nnnnnnnnnn nnnnnnnnnn | 7560 |
| nnnnnnnnnn nnnnnnnnnn nnnnnnnnnn nnnnnnnnnn nnnnnnnnnn nnnnnnnnnn | 7620 |
| nnnnnnnnnn nnnnnnnnnn nnnnnnnnnn nnnnnnnnnn nnaactagga atatttcaga | 7680 |
| cagatgccta actgctaagg ctcagagaaa cagcaaatta agtggatatc ctttatggat | 7740 |
| gactgtgatt ttttttcct ataatggaag ccaagtaaat aagatgctat tatcccacta | 7800 |
| aaagcagcgg ttctcaacct ctgggtctcc accccttgag gtcaaatgac acttttaccg | 7860 |
| agggtcatct aagacattgg aaaacacaga tatttacatt atgactcaca accgtagaaa | 7920 |
| aattacactt atgaagtagc aacgaactaa ttttatcctt gaggaatagg gggggtcacc | 7980 |
| acaacatgca gatctgtatt aaagggttgc agcattagga aggtttagaa ccactgccct | 8040 |
| aagagtaggc aagactgcag gtctctcatg ggacttgcct gtttgcctag tgtctcagcc | 8100 |
| tgcctctctt cttccctgca cagaggtcta gggtgacagg acatgtgaca gccagccgag | 8160 |
| tgaagcagca gggttggctt cccttgccct tcacatctgt ttcagcctgg gatgcaggga | 8220 |
| gcagttgcat gatgtcccgt gttttcactt cacagaagat ctgtgtgagc ttccaggagc | 8280 |
| ttcccggggc tttcaatatc tgattctggc agctgcagaga cagctgtgtc ttccacagcc | 8340 |
| ctccgtgtag aaatcggaat tcagagagct tttatcatgc tgaacagccg ggaccaggga | 8400 |
| aacctgcact ccggtttatg tctgtggcta tgtggattcc tggctctctt taaaggtgag | 8460 |
| ttattacggc ttatatccta gaatacaatt ggtagtgtgc atttcctctt ctttctcatc | 8520 |
| ttgtctggat ccaaataatt agaggacttt aattagttag gcttaaccta acagatatga | 8580 |
| tttggaaagt aaggtagaga aaacattgaa gtacagtata atattcatac ttcatctctc | 8640 |
| caactaaaat atgcttttcc aattagcata caaaatcatc tgcttttgta gccatgtatg | 8700 |
| ctaccaatat gcttcattta cttacggtaa tttgttagct gggacttatt agcctgcgag | 8760 |
| tcctaccaat gtgtgtaatt gtcctcactt aggaaacctg tcttattgtc tactaagagt | 8820 |
| gagctttcct gtcttaaaag ttggctcaga cctggctggt gcacacacac acacacacac | 8880 |
| acacacacac acacacacac acacgaacag gcacacatgc acacatctcg gatgaggttt | 8940 |
| caggggtgc tgatggtgag ctccagagag aggaaacagt agcaacagcc aagagagctc | 9000 |

```
actatcttct gaaacaatgt tttcatcctg gttagttaca caggnnnnnn nnnnnnnnnn    9060
nnnnnnnnnn nnnnnnnnnn nnnnnnnnnn nnnnnnnnnn nnnnnnnnnn nnnnnnnnnn    9120
nnnnnnnnnn nnnnnnnnnn nnnnnnnnnn nnnnnatgca tnnnnnnnnn nnnnnnnnnn    9180
nnnnnnnnnn nnnnnnnnnn nnnnnnnnnn nnnnnnnnnn nnnnnnnnnn nnnnnnnnnn    9240
nnnnnnnnnn nnnnnnnnnn nnnnnnnnnn nnnnnnnnnn nnnnnnnnnn nnnnnnnnnn    9300
nnnnnnnnnn nnnnnnnnnn nnnnnnnnnn nnnnnnnnnn nnnnnnnnnn nnnnnnnnnn    9360
nnnnnnnnnn nnnnnnnnnn nnnnnnnnnn nnnnnnnnnn nnnnnnnnnn nnnnnnnnnn    9420
nnnnnnnnnn nnnnnnnnnn nnnnnnnnnn nnnnnncata tgnnnnnnnn nnnnnnnnnn    9480
nnnnnnnnnn nnnnnnnnnn nnnnnnnnnn nnnnnnnnnn nnnnnnnnnn nnnnnnnnnn    9540
nnnnnnnnnn nnnnnnnnnn nnnnnnnnnn nnnnnnnnnn nnnnnnnnnn nnnnnnnnnn    9600
nnnnnnnnnn nnnnnnnnnn nnnnnnnnnn nnnnnnnnnn nnnnnnnnnn nnnnnnnnnn    9660
nnnnnnnnnn nnnnnnnnnn nnnnnnnnnn nnnnnnnnnn nnnnnnnnnn nnnnnnnnnn    9720
nnnnnnnnnn nnnnnnnnnn nnnnnnnnnn nnnnnnnnnn nnnnnnnnnn nnnnnnnnnn    9780
nnnnnnnnnn nnnnnnnnnn nnnnnnnnnn nnnnnnnnnn nnnnnnnnnn nnnnnnnnnn    9840
nnnnnnnnnn nnnnnnnnnn nnnnnnnnnn nnnnnnnnnn nnnnnnnnnn nnnnnnnnnn    9900
nnnnnnnnnn nnnnnnnnnn nnnnnnnnnn nnnnnnnnnn nnnnnnnnnn nnnnnnnnnn    9960
nnnnnnnnnn nnnnnnnnnn nnnnnnnnnn nnnnnnnnnn nnnnnnnnnn nnnnnnnnnn   10020
nnnnnnnnnn nnnnnnnnnn nnnnnnnnnn nnnnnnnnnn nnnnnnnnnn nnnnnnnnnn   10080
nnnnnnnnnn nnnnnnnnnn nnnnnnnnnn nnnnnnnnnn nnnnnnnnnn nnnnnnnnnn   10140
nnnnnnnnnn nnnnnnnnnn nnnnnnnnnn nnnnnnnnnn nnnnnnnnnn nnnnnnnnnn   10200
nnnnnngcag tacaggctgt gaatctgaag agcagctctt ccacaggctg tttgctcact   10260
acaaccgctt catccggccg gtggagaatg tctccgatcc cgtcacggtg catcttgaat   10320
tggcaatcac gcaactggcc aatgtgnnnn nnnnnnnnnn nnnnnnnnnn nnnnnnnnnn   10380
nnnnnnnnnn nnnnnnnnnn nnnnnnnnnn nnnnnnnnnn nnnnnnnnnn nnnnnnnnnn   10440
nnnnnnnnnn nnnnnnnnnn nnnnnnnnnn nnnnnnnnnn nnnnnnnnnn nnnnnnnnnn   10500
nnnnnnnnnn nnnnnnnnnn nnnnnnnnnn nnnnnnnnnn nnnnnnnnnn nnnnnnnnnn   10560
nnnnnnnnnn nnnnnnnnnn nnnnnnnnnn nnnnnnnnnn nnnnnntcta gannnnnnnn   10620
nnnnnnnnnn nnnnnnnnnn nnnnnnnnnn nnnnnnnnnn nnnnnnnnnn nnnnnnnnnn   10680
nnnnnnnnnn nnnnnnnnnn nnnnnnnnnn nnnnnnnnnn nnnnnnnnnn nnnnnnnnnn   10740
nnnnnnnnnn nnnnnnnnnn nnnnnnnnnn nnnnnnnnnn nnnnnnnnnn nnnnnnnnnn   10800
nnnnnnnnnn nnnnnnnnnn nnnnnnnnnn nnnnnnnnnn nnnnnnnnnn nnnnnnnact   10860
ccctgggctg agcatataca aaccatcaca ccatgtctgc cagttgattg cagcttttcc   10920
agaaactagt gcatttgaaa ccatgattca aaattgttca cctgggtgtc aactaatatt   10980
ttcccgataa agaggtctag gctaatggtt ccaacaacgt ggtgtggtac tgtgtgtctc   11040
tggcctcctc ctccattagg gctcactgag ctcagtgtcc attgaaatgg tctggagttg   11100
catgaagact atgatttttc cagagtaggt cctgactcat gacattttct aacacctcca   11160
aggttgtgta ttccccatga atacacacca tatggagcct atccaaacca tggaagtgtc   11220
tcaagggagg caggcctgtt aagaatggta ctgataatta gtgtcaactc cctgaactca   11280
cccaggtttt gaagactatg acaggtttag gccagttacc tctaagacct cacgaaagtg   11340
aggcagcaga gcctatccag cttttgaccaa cagctagtac atacttaccc agcatctgtt   11400
```

```
agaccctaca gattcaaggc gactcaatac cagagggccc taatcaatag aggggaatca   11460
ctgggaagct gtgcaggctc cattttccta agtcttttg ttgactttac caatcccagg    11520
gcctgtgttg gctccacatg acccactggc agggagaagc ttnnnnnnnn nnnnnnnnnn   11580
nnnnnnnnnn nnnnnnnnnn nnnnnnnnnn nnnnnnnnnn nnnnnnnnnn nnnnnnnnnn   11640
nnnnnnnnnn nnnnnnnnnn nnnnnnnnnn nnncctgcgt agaaacctca accaggctgg   11700
gatccttcac tcacagggac ctcagatgtc ttggaaaatg aaattttgaa tccctgctg    11760 actgctaaga acctactatt aatacccaag ctattctgct gtgacctgtc acctgtcctg   11820
actctcctta tgtcacttca gggactgctt ggacagtaac tcttcaaaga agcctccttg   11880
actcgtatat aaatagatg tgtgcataca cgcaggaatc actccacctc tcttgttata    11940
tcatgatgtg ttttatgctg gcgtacacat ttattattag ctctgtcttt ccaaccacaa   12000
cagctaagag cacatgaagg caggagcttt cttcactctg taacttgagt ggaactctgt   12060
aacacagtgg tcactgggta agtaggaata tcccttgtga ctgaagggcc cgtgagctgg   12120
gaaagggaat acagagggag tgagtacctg gtttcaactg gcaaacttgc atgtgaacta   12180
aactgctgtt tcagtttgga tcccagggca aatgcacaca gtacatccca ggcttctttg   12240
aggaaaggcc atgggggatag ataaaaacag tgagtacctg tcgccaccta caggactctc   12300
ccctctgtcg tccctgaacc tctgccctcc tccctgttac ctttcatgca tctaggaagc   12360
tttatgggcc aaggtggtga aaaagattc acagaggagg tgaaatccaa atgatctttg    12420
atcaatattt taagtcacat gtcatttcta agtcaacaga gcagaggcaa ctggaaacgt   12480
tcgggatttc tgttacagtt aaatagcttt catgcagtct ccagtcttca tgtctgactt    12540
cattagcacg gataacttag atttgtctat ttttagatat aattctctag ttaagacttg   12600
tattagcaag cacatagaag actgaaaaat attatttctt ccttccagga tgaagtcaac   12660
cagattatgg agaccaatct gtggctgcgt cacgtatgtg tcccccccctt tgaatggcgg   12720 cagaatgtat ccacttagtg ataaagccac ctgcattaac tttttcgcac cccaacctat   12780
gatagataaa aatatccctt ttccttgctt tctcctagtc cttgggtcag ctctggttgc   12840
agttatatta atataggcag cacatgggca gagcctggtg tctgacatgg aaccctctgg   12900
cctttctctt ttaagctccc agttctcttt gtatcactta ctgataccaa gnnnnnnnnn   12960
nnnnnnnnnn nnnnnnnnnn nnnnnnnnnn nnnnnnnnnn nnnnnnnnnn nnnnnnnnnn   13020
nnnnnnnnnn nnnnnnnnnn nnnnnnnnnn nnnnnnnnnn nnnnnnnnnn nnnnnnnnnn   13080
nnnnnnnnnn nnnnnnnnnn nnnnnnnnnn nnnnnnnnnn nnnnnnnnnn nnnnnnnnnn   13140
nnnnnnnnnn nnnnnnnnnn nnnnnnnnnn nnnnnnnnnn nnnnnnnnnn nnnnnnnnnn   13200
nnnnnnnnnn nnnnnnnnnn nnnnnnnnnn nnnnnnnnnn nnnnnnnnnn nnnnnnnnnn   13260
nnnnnnnnnn nnnnnnnnnn nnnnnnnnnn nnnnnnnnnn nnnnnnnnnn nnnnnnnnnn   13320
nnnnnnnnnn nnnnnnnnnn nnnnnnnnnn nnnnnnnnnn nnnnnnnnnn nnnnnnnnnn   13380
nnnnnnnnnn nnnnnnnnnn nnnnnnnnnn nnnnnnnnnn nnnnnnnnnn nnnnnnnnnn   13440
nnnnnnnnnn nnnnnnnnnn nnnnnnnnnn natctggaag gactacagat tgcgttggga   13500
tccaacggag tatgatggca tcgagacact tcgagttcca gcagacaaca tctggaagcc   13560
tgacatcgtt ctgtataacn nnnnnnnnat gcatnnnnnn nnnnnnnnnn nnnnnnnnnn   13620
nnnnnnnnnn nnnnnnnnnn nnnnnnnnnn nnnnnnnnnn nnnnnnnnnn nnnnnnnnnn   13680
nnnnnnnnnn nntctagann nnnnnnnnnn nnnnnnnnnn nnnnnnnnnn nnnnnnnnnn   13740
```

```
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnnn nnnnnnnnnn    14100
nnnnnnnnnn nnnnnnnnnn nnnnnnnnnn nnnnnnnnnn nnnnnnnnnn nnnnnnnnnn    14160
nnnnnnnnnn nnnnnnnnnn nnnnnnnnnn nnnnnnnnnn nnnnnnnnnn nnnnnnnnnn    14220
nnnnnnnnnn nnnnnnggat ccnnnnnnnn nnnnnnnnnn nnnnnnnnnn nnnnnnnnnn    14280
nnnnnnnnnn nnnnnnnnnn nnnnnnnnnn nnnnnnnnnn nnnnnnnnnn nnnnnnnnnn    14340
nnnnnnnnnn nnnnnnnnnn nnnnnnnnnn nnnnnnnnnn nnnnnnnnnn nnnnnnnnnn    14400
nnnnnnnnnn nnnnnnnnnn nnnnnnnnnn nnnnnnnnnn nnnnnnnnnn nnnnnnnnnn    14460
nnnnnnnnnn nnnnnnnnnn nnnnnnnnnn nnnnnnnnnn nnnnnnnnnn nnnnnnnnnn    14520
nnnnnnnnnn nnnnnnnnnn nnnnnnnnnn nnnnnnnnnn nnnnnnnnnn nnnnnnnnnn    14580
nnnnnnnnnn nnnnnnnnnn nnnnnnnnnn nnnnnnnnnn nnnnnnnnnn nnnnnnnnnn    14640
nnaatgctgt cggcgacttc caggtcgaag gcaagaccaa agctcttctc aagtatgacg    14700
gtgtgataac ctggaccccca ccagccatct ttaagagctc ctgcccaatg acatcacct    14760 tcttcccgtt tgaccatcaa aactgctccc tgaagtttgg ttcctggact tatgacaagg    14820
cagaaatcga ccttctcatc attggctcta agtagacat gaacgacttt tgggaaaaca    14880
gtgaatggga aattgtcgac gcctctggct ataagcatga catcaagtac aactgctgtg    14940
aagagattta cacggacata acctactcct tctacatcag gaggttgccc atgttttaca    15000
ccatcaacct catcatcccc tgcctcttca tttccttcct cacggtgctg gttttttacc    15060
ttccctccga ctgtggcgag aaagtgactc tttgcatctc cgttctgctt tctctcactg    15120 tcttttttgct ggtgattaca gagaccatcc catccacatc tctcgtgatc ccactggtgg    15180
gtgagtatct actgttcacc atgatctttg tcacgctgtc cattgtggtg accgtgttcg    15240
tgctgaacat acactacagg accccagcaa cgcataccat gcccaagtgg gtgaagacca    15300
tcttccttca ggccttcccc tcgattctga tgatgaggaa acctctggac aagacaaagg    15360
aggcaggagg tgttaaggac cccaaaagcc ataccaagag gcctgccaag gtcaaattta    15420
ctcatcgagg agaatccaaa cttctaaagg aatgccacca ctgccaaaaa tcaagtgaca    15480
tagcacctgg aaagaagaa tcaagccagc agcctgcacg gtgggtggca gagaattcag    15540
agcactcgtc cgatgttgaa gatgtcatcg agagtgttca attcatagca gaaaacatga    15600
agagccacaa tgaaacaaac gaggtaaaag tggagccctt ttctccagcc agctgcaccc    15660
ctagcaggcc tacaggcact ttagagacta gtcagagcgt cagtgggagt tacatatgtg    15720
gaacagtcag ggaccgtcac ctaagaccag ctctattatc atgaagcctt gtgggacctg    15780
ggttcaagtt tagggagcta tagtgagagg atatatgtag tcctacaaca aatcttcagc    15840
ctgcatttac ttacggtgag gtctagccac agtgcacatg caggacaagc cttcctcaag    15900
gaacaagcct ccaatgcatc gaacactgac aaagtgaggg tgggaaggga gactgtgaaa    15960
atcattatta ataaaatccc accggcgggc ttgctacctg ctctaatggt ttgtgttccc    16020
aaatgaaaca cacacacaca cacacacaca cacacacaca cacacacagt ctttgtgttt    16080
taatatgccg tatacagcac aatagctggg ccactgccta ccctccatgc tgttactata    16140
```

```
cctcccgcca acaatcccca agttattact tactaattct atgtgctatc ttggttgccc  16200
ctagacccag ttgggcagcc tctgggccat gttttccccg gctatttcaa gtggtggcca  16260
tgtctctctg tcctgcagtc ttctcaggcc tagcatctca cctcttcctc cacactctcc  16320
cggcatggca gggtctcact tctcctcctc ctcctcctcc tcctccacca cctcctttct  16380
cctccctccc tcctccctcc cctctttccc ctcccccctt ccttcccagc ctgagaactc  16440
ctaaaatccc acctctccct gtcctttcca gctttggctg ttggcagctt tatttaccaa  16500
taagaaccaa ctgcgggcag gttcccagaa actacaggca gacagtccca cgaaaacagt  16560
tttacgtgga ccataattag cattcataat acgtgcagct acagagacac ccaaggaaaa  16620
gaagaactgt ggtactgcct gaagcccag tggtgaaaga tgccccttag cagtcagcag  16680
ctcccatcac acttcctcta ctagaggggg acccagacat gagttaaaga catcttgaag  16740
atgtgctcag tatgcacacg tattccgtgc ctgtgtccca cactctaatg cctagagctt  16800
ggctcctcct accccaagca agtgctcaag gatagggaga tcaccacttg actgaggttt  16860
cccgccaggt gtctggagat gcttcatact atagctccta acatctgtaa ctcataggga  16920
aagaatatca gaaccaccac caccccccaa aaaacacact gagagacact gagaatgcct  16980
gtcataacat gtcacaggag agcaatggcc agtgagctca cctcctggct ggcatctttt  17040
agaatgtacg gcaatacgtt acgttgattt atcannnnnn nnnnnnnnnn nnnnnnnnnn  17100
nnnnnnnnnn nnnnnnnnnn nnnnnnnnnn nnnnnnnnnn nnnnnnnnnn nnnnnnnnnn  17160
nnnnnnnnnn nnnnnnnnnn nnnnnnnnnn nnnnnnnnnn nnnnnnnnnn nnnnnnnnnn  17220
nnnnnnnnnn nnnnnnnnct ctcacttgct tcacactcag attcccccca aacagccagg  17280
cacacgtgac aagagcttga ctctcaagca gatatattgt gtagagcgaa gaaaggaccc  17340
ttatcacagg caaagggtca caaaagtctt tgatacagtt catagcccag tgatgtacat  17400
ctgctctccc ttagaccatg agtcctacat aggacatgca ggcagtcagg caggcaaaca  17460
taatagcaat aattggtttt tttgaaagga ttggagaaaa tgctttggag aaaaaaaaaa  17520
gtattcataa aacatagcat gttttcttat agtcttggtt tttaaagcta gccttgatcc  17580
tttgtttgca tttcaggtag aagacgactg gaaatacatg gctatggtgg tggacagagt  17640
cttcctttgg gtatttataa ttgtctgtgt gtttggaact gtggggctat ttctgcagcc  17700
actgcttggg aacacaggaa actcttaatt ggtattgtcc ctccgagctc atcaagct    17758
```